US011230577B2

(12) United States Patent
Barish et al.

(10) Patent No.: US 11,230,577 B2
(45) Date of Patent: Jan. 25, 2022

(54) CHIMERIC ANTIGEN RECEPTORS CONTAINING A CHLOROTOXIN DOMAIN

(71) Applicant: City of Hope, Duarte, CA (US)

(72) Inventors: Michael Barish, Duarte, CA (US); Christine E. Brown, Duarte, CA (US); Stephen J. Forman, Duarte, CA (US); Dongrui Wang, Duarte, CA (US)

(73) Assignee: City of Hope, Duarte, CA (US)

( * ) Notice: Subject to any disclaimer, the term of this patent is extended or adjusted under 35 U.S.C. 154(b) by 292 days.

(21) Appl. No.: 15/767,960

(22) PCT Filed: Oct. 13, 2016

(86) PCT No.: PCT/US2016/056901
§ 371 (c)(1),
(2) Date: Apr. 12, 2018

(87) PCT Pub. No.: WO2017/066481
PCT Pub. Date: Apr. 20, 2017

(65) Prior Publication Data

US 2019/0389917 A1 Dec. 26, 2019

Related U.S. Application Data

(60) Provisional application No. 62/241,021, filed on Oct. 13, 2015.

(51) Int. Cl.

| | |
|---|---|
| ***A61K 49/00*** | (2006.01) |
| ***C07H 19/00*** | (2006.01) |
| ***C07H 21/04*** | (2006.01) |
| ***C07K 14/435*** | (2006.01) |
| ***A61P 35/00*** | (2006.01) |
| ***A61K 35/17*** | (2015.01) |
| ***C07K 14/725*** | (2006.01) |
| ***C07K 14/73*** | (2006.01) |
| ***C07K 14/705*** | (2006.01) |
| ***C12N 5/0783*** | (2010.01) |

(52) U.S. Cl.

CPC ........ *C07K 14/43522* (2013.01); *A61K 35/17* (2013.01); *A61P 35/00* (2018.01); *C07K 14/7051* (2013.01); *C07K 14/70514* (2013.01); *C07K 14/70517* (2013.01); *C07K 14/70521* (2013.01); *C07K 14/70578* (2013.01); *C12N 5/0638* (2013.01); *C07K 2319/03* (2013.01); *C07K 2319/30* (2013.01); *C07K 2319/55* (2013.01); *C12N 2510/00* (2013.01)

(58) Field of Classification Search

CPC ................ A61K 49/00; A61K 2039/51; C07K 14/43522; C07K 2310/55
USPC .......................... 536/22.1, 23.1; 424/9.1, 9.2
See application file for complete search history.

(56) References Cited

FOREIGN PATENT DOCUMENTS

| | | |
|---|---|---|
| CN | 1924006 | 3/2007 |
| CN | 102844044 | 10/2016 |
| JP | 2012-501180 | 1/2012 |
| WO | WO 2010/025177 | 3/2010 |
| WO | WO 2014/153270 | 9/2014 |
| WO | WO 2015/105522 | 7/2015 |

OTHER PUBLICATIONS

Ahmed et al. "HER2-specific T cells target primary glioblastoma stem cells and induce regression of autologous experimental tumors," Clin Cancer Res, Jan. 15, 2010, 16(2):474-485.
Brown et al., "Stem-like tumor-initiating cells isolated from IL13Rα2 expressing gliomas are targeted and killed by IL13-zetakine-redirected T Cells," Clin Cancer Res., Apr. 15, 2012, 18(8):2199-2209.
Brown et al., "Tumor-derived chemokine MCP-1/CCL2 is sufficient for mediating tumor tropism of adoptively transferred T cells," J Immunol., Sep. 1, 2007, 179(5):3332-3341.
Cartellieri et al., "Chimeric Antigen Receptor-Engineered T Cells for Immunotherapy of Cancer," J Biomed Biotechnol, Feb. 15, 2010, 2010, :956304-1.
Chen et al., "Recent advances in diagnosis and treatment of cliomas using chlorotoxin-baased bioconjugates," Am J Med Med Imaging, 4(5):385-405.
Chow et al., "T cells redirected to EphA2 for the immunotherapy of glioblastoma," Mol Ther, Mar. 2013, 21(3):629-637.
Or Cohen-Inbar, "Recruitment of Immune Effector Cells Against Astrocytoma by MHC-Chlorotoxin Chimeric Proteins. Characterization of Melanoma Derived Differentiation Antigens in Malignant Astrocytomas. Ph.D Thesis," Technion, Israeli Institute of Technology, Faculty of Medicine, Israel, May 2014, 139 pages.
Dardevet et al., "Chlorotoxin: a helpful natural scorpion peptide to diagnose glioma and fight tumor invasion," Toxins (Basel)., Mar. 27, 2015, 7(4):1079-1101.
Edelman et al., "The covalent structure of an entire gammaG immunoglobulin molecule," Proc Natl Acad Sci USA., May 1969, 63(1):78-85.
Hong et al., "Successful treatment of melanoma brain metastases with adoptive cell therapy," Clin Cancer Res, Oct. 1, 2010, 16(19):4892-4898.
International Preliminary Report on Patentability in International Application No. PCT/US2016/056901, dated Apr. 17, 2018, 10 pages.
International Search Report and Written Opinion in International Application No. PCT/US2016/056901, dated Feb. 28, 2017, 17 pages.
Sampson et al., "EGFRvIII mCAR-modified T-cell therapy cures mice with established intracerebral glioma and generates host immunity against tumor-antigen loss," Clin Cancer Res, Feb. 15, 2014, 20(4):972-984.

(Continued)

*Primary Examiner* — Rodney P Swartz
(74) *Attorney, Agent, or Firm* — Fish & Richardson P.C.

(57) ABSTRACT

Chimeric transmembrane immunoreceptors (CAR) which include an extracellular domain that includes chlorotoxin or a related toxin, or a variant of chlorotoxin or a related toxin, that binds to human glioma or other human tumor cells, a transmembrane region, a costimulatory domain and an intracellular signaling domain are described.

41 Claims, 25 Drawing Sheets

Specification includes a Sequence Listing.

(56) References Cited

OTHER PUBLICATIONS

Yaghoubi et al., "Noninvasive detection of therapeutic cytolytic T cells with 18F-FHBG PET in a patient with glioma," Nat Clin Pract Oncol., Jan. 2009, 6(1):53-58.
Japanese Office Action in Japanese Application No. 2018-519030, dated Sep. 30, 2020, 10 pages.
Chinese Office Action in Chinese Application No. 201680072823.2, dated May 8, 2021, 8 pages.

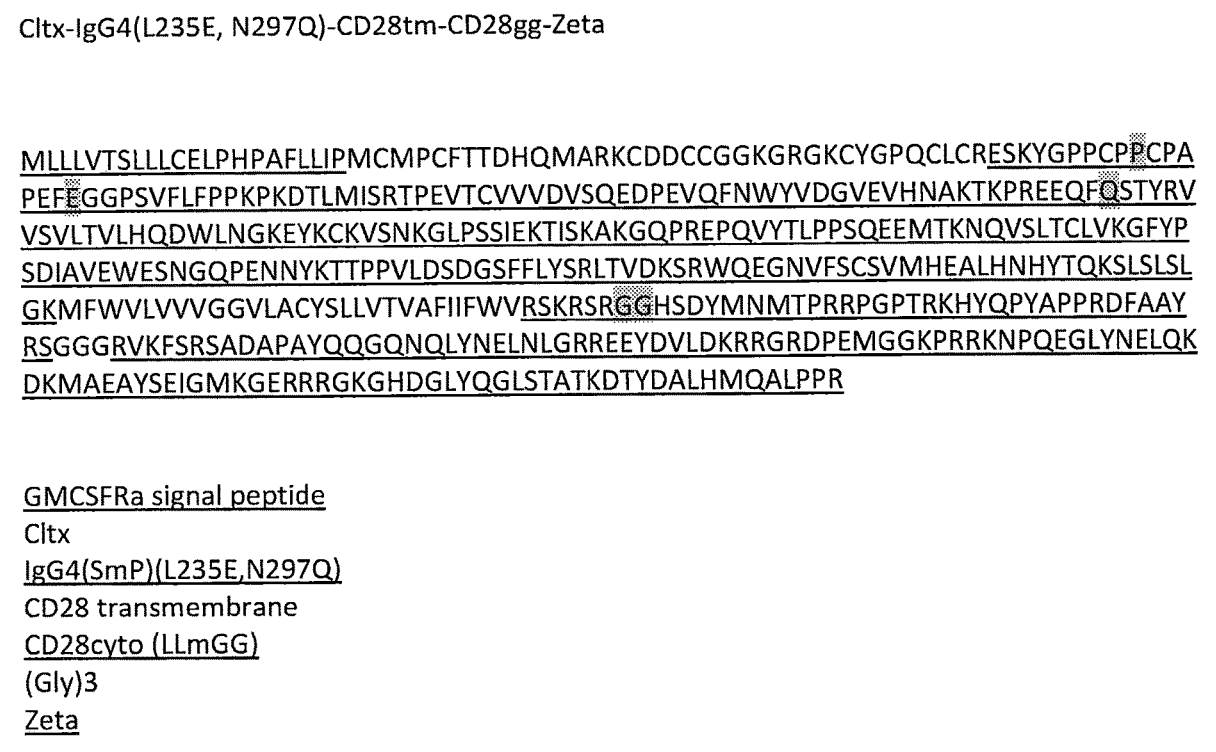

Cltx-IgG4(L235E, N297Q)-CD28tm-CD28gg-Zeta

MLLLVTSLLLCELPHPAFLLIPMCMPCFTTDHQMARKCDDCCGGKGRGKCYGPQCLCRESKYGPPCPPCPA
PEFEGGPSVFLFPPKPKDTLMISRTPEVTCVVVDVSQEDPEVQFNWYVDGVEVHNAKTKPREEQFQSTYRV
VSVLTVLHQDWLNGKEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHEALHNHYTQKSLSLSL
GKMFWVLVVVGGVLACYSLLVTVAFIIFWVRSKRSRGGHSDYMNMTPRRPGPTRKHYQPYAPPRDFAAY
RSGGGRVKFSRSADAPAYQQGQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR

GMCSFRa signal peptide
Cltx
IgG4(SmP)(L235E,N297Q)
CD28 transmembrane
CD28cyto (LLmGG)
(Gly)3
Zeta

FIGURE 9

Cltx-IgG4(HL-CH3)-CD28tm-CD28gg-Zeta

MLLLVTSLLLCELPHPAFLLIPMCMPCFTTDHQMARKCDDCCGGKGRGKCYGPQCLCRESKYGPPCPPCPG
GGSSGGGSGGQPREPQVYTLPPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLGKMFWVLVVVGGVLACYSLLVTVAFIIF
WVRSKRSRGGHSDYMNMTPRRPGPTRKHYQPYAPPRDFAAYRSGGGRVKFSRSADAPAYQQGQNQLY
NELNLGRREEYDVLDKRRGRDPEMGGKPRRKNPQEGLYNELQKDKMAEAYSEIGMKGERRRGKGHDGLY
QGLSTATKDTYDALHMQALPPR

GMCSFRa signal peptide
Cltx
IgG4(SmP)-Hinge
Linker
IgG4-CH3
CD28 transmembrane
CD28cyto (LLmGG)
(Gly)3
Zeta

FIGURE 10

Cltx-CD8h-CD28tm-CD28gg-Zeta

MLLLVTSLLLCELPHPAFLLIPMCMPCFTTDHQMARKCDDCCGGKGRGKCYGPQCLCRTTTPAPRPPTPAP
TIASQPLSLRPEACRPAAGGAVHTRGLDFACDMFWVLVVVGGVLACYSLLVTVAFIIFWVRSKRSRGGHSD
YMNMTPRRPGPTRKHYQPYAPPRDFAAYRSGGGRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALH
MQALPPR

GMCSFRa signal peptide
Cltx
CD8h
CD28 transmembrane
CD28cyto (LLmGG)
(Gly)3
Zeta

FIGURE 11

Cltx-IgG4H-CD28tm-CD28gg-Zeta

MLLLVTSLLLCELPHPAFLLIPMCMPCFTTDHQMARKCDDCCGGKGRGKCYGPQCLCRESKYGPPCPPCP
MFWVLVVVGGVLACYSLLVTVAFIIFWVRSKRSRGGHSDYMNMTPRRPGPTRKHYQPYAPPRDFAAYRS
GGGRVKFSRSADAPAYQQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR

GMCSFRa signal peptide
Cltx
IgG4(SmP)-Hinge
CD28 transmembrane
CD28cyto (LLmGG)
(Gly)3
Zeta

FIGURE 12

Cltx-L-CD28tm-CD28gg-Zeta

<u>MLLLVTSLLLCELPHPAFLLIP</u>MCMPCFTTDHQMARKCDDCCGGKGRGKCYGPQCLCR<u>GGGSSGGGSG</u>M
FWVLVVVGGVLACYSLLVTVAFIIFWV<u>RSKRSRGGHSDYMNMTPRRPGPTRKHYQPYAPPRDFAAYRS</u>GG
G<u>RVKFSRSADAPAYQQGQNQLYNELNLGRREEYDVLDKRRGRDPEMGGKPRRKNPQEGLYNELQKDKM</u>
<u>AEAYSEIGMKGERRRGKGHDGLYQGLSTATKDTYDALHMQALPPR</u>

<u>GMCSFRa signal peptide</u>
Cltx
<u>Linker</u>
CD28 transmembrane
<u>CD28cyto (LLmGG)</u>
(Gly)3
<u>Zeta</u>

FIGURE 13

Cltx-IgG4(L235E, N297Q)-CD28tm-CD28gg-41BB-Zeta

MLLLVTSLLLCELPHPAFLLIPMCMPCFTTDHQMARKCDDCCGGKGRGKCYGPQCLCRESKYGPPCPPCPA
PEFEGGPSVFLFPPKPKDTLMISRTPEVTCVVVDVSQEDPEVQFNWYVDGVEVHNAKTKPREEQFQSTYRV
VSVLTVLHQDWLNGKEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHEALHNHYTQKSLSLSL
GKMFWVLVVVGGVLACYSLLVTVAFIIFWVRSKRSRGGHSDYMNMTPRRPGPTRKHYQPYAPPRDFAAY
RSGGGKRGRKKLLYIFKQPFMRPVQTTQEEDGCSCRFPEEEEGGCELGGGRVKFSRSADAPAYQQGQNQL
YNELNLGRREEYDVLDKRRGRDPEMGGKPRRKNPQEGLYNELQKDKMAEAYSEIGMKGERRRGKGHDGL
YQGLSTATKDTYDALHMQALPPR

GMCSFRa signal peptide
Cltx
IgG4(SmP)(L235E,N297Q)
CD28 transmembrane
CD28cyto (LLmGG)
(Gly)3
41BB
(Gly)3
Zeta

FIGURE 14

Cltx-IgG4(HL-CH3)-CD28tm-CD28gg-41BB-Zeta

MLLLVTSLLLCELPHPAFLLIPMCMPCFTTDHQMARKCDDCCGGKGRGKCYGPQCLCRESKYGPPCPPCPG
GGSSGGGSGGQPREPQVYTLPPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLGKMFWVLVVVGGVLACYSLLVTVAFIIF
WVRSKRSRGGHSDYMNMTPRRPGPTRKHYQPYAPPRDFAAYRSGGGKRGRKKLLYIFKQPFMRPVQTTQ
EEDGCSCRFPEEEEGGCELGGGRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHMQALPPR

GMCSFRa signal peptide
Cltx
IgG4(SmP)-Hinge
Linker
IgG4-CH3
CD28 transmembrane
CD28cyto (LLmGG)
(Gly)3
41BB
(Gly)3
Zeta

FIGURE 15

Cltx-CD8h-CD28tm-CD28gg-41BB-Zeta

MLLLVTSLLLCELPHPAFLLIPMCMPCFTTDHQMARKCDDCCGGKGRGKCYGPQCLCRTTTPAPRPPTPAP
TIASQPLSLRPEACRPAAGGAVHTRGLDFACDMFWVLVVVGGVLACYSLLVTVAFIIFWVRSKRSRGGHSD
YMNMTPRRPGPTRKHYQPYAPPRDFAAYRSGGGKRGRKKLLYIFKQPFMRPVQTTQEEDGCSCRFPEEEE
GGCELGGGRVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR

GMCSFRa signal peptide
Cltx
CD8h
CD28 transmembrane
CD28cyto (LLmGG)
(Gly)3
41BB
(Gly)3
Zeta

FIGURE 16

Cltx-IgG4H-CD28tm-CD28gg-41BB-Zeta

MLLLVTSLLLCELPHPAFLLIPMCMPCFTTDHQMARKCDDCCGGKGRGKCYGPQCLCRESKYGPPCPPCP
MFWVLVVVGGVLACYSLLVTVAFIIFWVRSKRSRGGHSDYMNMTPRRPGPTRKHYQPYAPPRDFAAYRS
GGGKRGRKKLLYIFKQPFMRPVQTTQEEDGCSCRFPEEEEGGCELGGGRVKFSRSADAPAYQQGQNQLYN
ELNLGRREEYDVLDKRRGRDPEMGGKPRRKNPQEGLYNELQKDKMAEAYSEIGMKGERRRGKGHDGLYQ
GLSTATKDTYDALHMQALPPR

GMCSFRa signal peptide
Cltx
IgG4(SmP)-Hinge
CD28 transmembrane
CD28cyto (LLmGG)
(Gly)3
41BB
(Gly)3
Zeta

FIGURE 17

Cltx-L-CD28tm-CD28gg-41BB-Zeta

MLLLVTSLLLCELPHPAFLLIPMCMPCFTTDHQMARKCDDCCGGKGRGKCYGPQCLCRGGGSSGGGSGM
FWVLVVVGGVLACYSLLVTVAFIIFWVRSKRSRGGHSDYMNMTPRRPGPTRKHYQPYAPPRDFAAYRSGG
GKRGRKKLLYIFKQPFMRPVQTTQEEDGCSCRFPEEEEGGCELGGGRVKFSRSADAPAYQQGQNQLYNEL
NLGRREEYDVLDKRRGRDPEMGGKPRRKNPQEGLYNELQKDKMAEAYSEIGMKGERRRGKGHDGLYQG
LSTATKDTYDALHMQALPPR

GMCSFRa signal peptide
Cltx
Linker
CD28 transmembrane
CD28cyto (LLmGG)
(Gly)3
41BB
(Gly)3
Zeta

FIGURE 18

Cltx-IgG4(L235E,N297Q)-CD4tm-41BB-Zeta

MLLLVTSLLLCELPHPAFLLIPMCMPCFTTDHQMARKCDDCCGGKGRGKCYGPQCLCRESKYGPPCPPCPA
PEFEGGPSVFLFPPKPKDTLMISRTPEVTCVVVDVSQEDPEVQFNWYVDGVEVHNAKTKPREEQFQSTYRV
VSVLTVLHQDWLNGKEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHEALHNHYTQKSLSLSL
GKMALIVLGGVAGLLLFIGLGIFFKRGRKKLLYIFKQPFMRPVQTTQEEDGCSCRFPEEEEGGCELGGGRVKF
SRSADAPAYQQGQNQLYNELNLGRREEYDVLDKRRGRDPEMGGKPRRKNPQEGLYNELQKDKMAEAYSE
IGMKGERRRGKGHDGLYQGLSTATKDTYDALHMQALPPR

GMCSFRa signal peptide
Cltx
IgG4(SmP)(L235E, N297Q)
CD4 transmembrane
4-1BB cyto
(Gly)3
Zeta

FIGURE 19

Cltx-IgG4(HL-CH3)-CD4tm-41BB-Zeta

MLLLVTSLLLCELPHPAFLLIPMCMPCFTTDHQMARKCDDCCGGKGRGKCYGPQCLCRESKYGPPCPPCPG
GGSSGGGSGGQPREPQVYTLPPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLGKMALIVLGGVAGLLLFIGLGIFFKRGRK
KLLYIFKQPFMRPVQTTQEEDGCSCRFPEEEEGGCELGGGRVKFSRSADAPAYQQGQNQLYNELNLGRREE
YDVLDKRRGRDPEMGGKPRRKNPQEGLYNELQKDKMAEAYSEIGMKGERRRGKGHDGLYQGLSTATKDT
YDALHMQALPPR

GMCSFRa signal peptide
Cltx
IgG4(SmP)Hinge
Linker
IgG4 CH3
CD4 transmembrane
4-1BB cyto
(Gly)3
Zeta

FIGURE 20

Cltx-CD8h-CD28tm-41BB-Zeta

MLLLVTSLLLCELPHPAFLLIPMCMPCFTTDHQMARKCDDCCGGKGRGKCYGPQCLCRTTTPAPRPPTPAP
TIASQPLSLRPEACRPAAGGAVHTRGLDFACDMFWVLVVVGGVLACYSLLVTVAFIIFWVKRGRKKLLYIFK
QPFMRPVQTTQEEDGCSCRFPEEEEGGCELGGGRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALH
MQALPPR

GMCSFRa signal peptide
CLTX
CD8h
CD28 transmembrane
4-1BB cyto
(Gly)3
Zeta

FIGURE 21

Cltx-IgG4H-CD28tm-41BB-Zeta

MLLLVTSLLLCELPHPAFLLIPMCMPCFTTDHQMARKCDDCCGGKGRGKCYGPQCLCRESKYGPPCPPCP
MFWVLVVVGGVLACYSLLVTVAFIIFWVKRGRKKLLYIFKQPFMRPVQTTQEEDGCSCRFPEEEEGGCELG
GGRVKFSRSADAPAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

GMCSFRa signal peptide
CLTX
IgG4(SmP)Hinge
CD28 transmembrane
4-1BB cyto
(Gly)3
Zeta

FIGURE 22

Cltx-L-CD28tm-41BB-Zeta

MLLLVTSLLLCELPHPAFLLIPMCMPCFTTDHQMARKCDDCCGGKGRGKCYGPQCLCRGGGSSGGGSGM
FWVLVVVGGVLACYSLLVTVAFIIFWVKRGRKKLLYIFKQPFMRPVQTTQEEDGCSCRFPEEEEGGCELGGG
RVKFSRSADAPAYQQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPR

GMCSFRa signal peptide
CLTX
Linker
CD28 transmembrane
4-1BB cyto
(Gly)3
Zeta

FIGURE 23

Cltx-L-CD28tm-41BB-Zeta-T2A-CD19t

MLLLVTSLLLCELPHPAFLLIPMCMPCFTTDHQMARKCDDCCGGKGRGKCYGPQCLCRGGGSSGGGSGM
FWVLVVVGGVLACYSLLVTVAFIIFWVKRGRKKLLYIFKQPFMRPVQTTQEEDGCSCRFPEEEEGGCELGGG
RVKFSRSADAPAYQQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPRLEGGGEGRGSLLTCGDVEENPGPRM
PPPRLLFFLLFLTPMEVRPEEPLVVKVEEGDNAVLQCLKGTSDGPTQQLTWSRESPLKPFLKLSLGLPGLGIH
MRPLAIWLFIFNVSQQMGGFYLCQPGPPSEKAWQPGWTVNVEGSGELFRWNVSDLGGLGCGLKNRSSE
GPSSPSGKLMSPKLYVWAKDRPEIWEGEPPCVPPRDSLNQSLSQDLTMAPGSTLWLSCGVPPDSVSRGPLS
WTHVHPKGPKSLLSLELKDDRPARDMWVMETGLLLPRATAQDAGKYYCHRGNLTMSFHLEITARPVLWH
WLLRTGGWKVSAVTLAYLIFCLCSLVGILHLQRALVLRRKR

GMCSFRa signal peptide
CLTX
Linker
CD28 transmembrane
4-1BB cyto
(Gly)3
Zeta
T2A
CD19t

FIGURE 24

| Toxin | Primary Sequence | Length | Identity | Disulfide Bridge Pattern | Species |
|---|---|---|---|---|---|
| Chlorotoxin | MC$_1$MPC$_2$FTTDHQMARKC$_3$DDC$_4$C$_5$G-GK-GRGKC$_6$YGPQC$_7$LC$_8$-R | 36 AA | 100% | $C_1$-$C_4$,$C_2$-$C_6$,$C_3$-$C_7$,$C_5$-$C_8$ | *Leiurus quinquestriuatus quinquestriatus* |
| I1 | MC$_1$MPC$_2$FTTRPDMAQQC$_3$RAC$_4$C$_5$K-GK-GK--C$_6$FGPQC$_7$LC$_8$-GYD- | 36.AA | 71% | $C_1$-$C_4$,$C_2$-$C_6$,$C_3$-$C_7$,$C_5$-$C_8$ | *Buthus eupeus* |
| I3 | MC$_1$MPC$_2$FTTDHQTARRC$_3$RDC$_4$C$_5$G-GR-GR-KC$_6$FG-QC$_7$LC$_8$-GYD- | 36 AA | 82% | $C_1$-$C_4$,$C_2$-$C_6$,$C_3$-$C_7$,$C_5$-$C_8$ | *Buthus eupeus* |
| I4 | MC$_1$MPC$_2$FTTDHNMAKKC$_3$RDC$_4$C$_5$G-GN---GKC$_6$FGPQC$_7$LC$_8$-NR | 35 AA | 82% | $C_1$-$C_4$,$C_2$-$C_6$,$C_3$-$C_7$,$C_5$-$C_8$ | *Buthus eupeus* |
| I5 | MC$_1$MPC$_2$FTTDPNMANKC$_3$RDC$_4$C$_5$G-GG-KK--C$_6$FGPQC$_7$LC$_8$-NR | 35 AA | 79% | $C_1$-$C_4$,$C_2$-$C_6$,$C_3$-$C_7$,$C_5$-$C_8$ | *Buthus eupeus* |
| I5,A | MC$_1$MPC$_2$FTTDPNMAKKC$_3$RDC$_4$C$_5$G-GN-GK--C$_6$FGPQC$_7$LC$_8$-NR | 35 AA | 79% | $C_1$-$C_4$,$C_2$-$C_6$,$C_3$-$C_7$,$C_5$-$C_8$ | *Buthus eupeus* |
| Bs-8 | RC$_1$KPC$_2$FTTDPQMSKKC$_3$ADC$_4$C$_5$G-GK-GKGKC$_6$YGPQC$_7$LC$_8$---- | 35 AA | 80% | $C_1$-$C_4$,$C_2$-$C_6$,$C_3$-$C_7$,$C_5$-$C_8$ | *Buthus eupeus* |
| Lqh-8/6 | RC$_1$SPC$_2$FTTDQQMTKKC$_3$YDC$_4$C$_5$G-GK-GKGKC$_6$YGPQC-IC$_7$LC$_8$APY | 38 AA | 72% | $C_1$-$C_4$,$C_2$-$C_6$,$C_3$-$C_7$,$C_5$-$C_8$ | *Leiurus quinquestriuatus hebraeus* |
| PBIT1 | RC$_1$KPC$_2$FTTDPQMSKKC$_3$ADX$_4$C$_5$G-GX--KX | 25 AA | 64% | | *Buthus sindicus* |
| Bs-14 | -C$_1$GPC$_2$FTKDPETEKKC$_3$ATC$_4$C$_5$G-GI-GR--C$_6$FGPQC-C$_7$LC$_8$NRGY | 36 AA | 61% | $C_1$-$C_4$,$C_2$-$C_6$,$C_3$-$C_7$,$C_5$-$C_8$ | *Androctonus mauretanicus* |
| Neurotoxin P2 | -C$_1$GPC$_2$FTKDPYTESKC$_3$ATC$_4$C$_5$G-GR-GK--C$_6$VGPQC$_7$LC$_8$NRI- | 35 AA | 70% | $C_1$-$C_4$,$C_2$-$C_6$,$C_3$-$C_7$,$C_5$-$C_8$ | *Mauretanicus*<br>*Androctonus* |
| AaCtx | MC$_1$IPC$_2$FTTNPNMAAKC$_3$NAC$_4$C$_5$G-SRRGS--C$_6$RGPQC$_7$IC$_8$---- | 34 AA | 61% | $C_1$-$C_4$,$C_2$-$C_6$,$C_3$-$C_7$,$C_5$-$C_8$ | *Australis* |
| GaTx1 | -C$_1$GPC$_2$FTTDHQMEQKC$_3$AEC$_4$C$_5$G-GI-GK--C$_6$VGPQC$_7$LC$_8$NR-- | 34 AA | 79% | $C_1$-$C_4$,$C_2$-$C_6$,$C_3$-$C_7$,$C_5$-$C_8$ | *Leiurus quinquestriatus hebraeus* |
| BmKCT | -C$_1$GPC$_2$FTTDANMARKC$_3$REC$_4$C$_5$G-GI-GK--C$_6$FGPQC$_7$LC$_8$NRI- | 35 AA | 76% | $C_1$-$C_4$,$C_2$-$C_6$,$C_3$-$C_7$,$C_5$-$C_8$ | *Buthus martensii* |
| Bm12-b | -C$_1$GPC$_2$FTTDANMARKC$_3$REC$_4$C$_5$G-GN-GK--C$_6$FGPQC$_7$LC$_8$NRE- | 35 AA | 76% | $C_1$-$C_4$,$C_2$-$C_6$,$C_3$-$C_7$,$C_5$-$C_8$ | *Buthus martensii* |
| Lepidopteran | RC$_1$GPC$_2$FTTDQTQAKC$_3$SEC$_4$C$_5$G-RK-GG-V-C$_6$KGPQC$_7$IC$_8$GIQ- | 37 AA | 63% | $C_1$-$C_4$,$C_2$-$C_6$,$C_3$-$C_7$,$C_5$-$C_8$ | *Buthus tamulus* |
| BtITx3 | RC$_1$PPC$_2$FTTNPMEADC$_3$RKC$_4$C$_5$G-GR-GY-V-C$_6$ASYQC$_7$IC$_8$PG-- | 35 AA | 53% | $C_1$-$C_4$,$C_2$-$C_6$,$C_3$-$C_7$,$C_5$-$C_8$ | *Buthus tamulus* |
| GaTx2 | --VC$_1$......EDC$_2$PDHC$_3$STQK-ARAKC$_4$DNDKC$_5$VC$_6$-EPI | 29 AA | 38% | $C_1$-$C_4$,$C_2$-$C_5$,$C_3$-$C_6$ | *Leiurus quinquestriatus hebraeus* |

FIG. 25

```
                                SEQUENCE LISTING

<160> NUMBER OF SEQ ID NOS: 77

<210> SEQ ID NO 1
<211> LENGTH: 36
<212> TYPE: PRT
<213> ORGANISM: Leiurus quinquestriatus

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35


<210> SEQ ID NO 2
<211> LENGTH: 10
<212> TYPE: PRT
<213> ORGANISM: Artificial Sequence
<220> FEATURE:
<223> OTHER INFORMATION: linker

<400> SEQUENCE: 2

Gly Gly Gly Ser Ser Gly Gly Gly Ser Gly
1               5                   10


<210> SEQ ID NO 3
<211> LENGTH: 12
<212> TYPE: PRT
<213> ORGANISM: Artificial Sequence
<220> FEATURE:
<223> OTHER INFORMATION: mutated IgG4 hinge

<400> SEQUENCE: 3

Glu Ser Lys Tyr Gly Pro Pro Cys Pro Pro Cys Pro
1               5                   10


<210> SEQ ID NO 4
<211> LENGTH: 12
<212> TYPE: PRT
<213> ORGANISM: Homo sapiens

<400> SEQUENCE: 4

Glu Ser Lys Tyr Gly Pro Pro Cys Pro Ser Cys Pro
1               5                   10


<210> SEQ ID NO 5
<211> LENGTH: 22
<212> TYPE: PRT
<213> ORGANISM: Artificial Sequence
<220> FEATURE:
<223> OTHER INFORMATION: mutated IgG4 hinge +linker

<400> SEQUENCE: 5
```

-continued

```
Glu Ser Lys Tyr Gly Pro Pro Cys Pro Pro Cys Pro Gly Gly Gly Ser
1               5                   10                  15

Ser Gly Gly Gly Ser Gly
            20


<210> SEQ ID NO 6
<211> LENGTH: 39
<212> TYPE: PRT
<213> ORGANISM: Homo sapiens

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 7
<211> LENGTH: 48
<212> TYPE: PRT
<213> ORGANISM: Homo sapiens

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45


<210> SEQ ID NO 8
<211> LENGTH: 45
<212> TYPE: PRT
<213> ORGANISM: Homo sapiens

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 9
<211> LENGTH: 129
<212> TYPE: PRT
<213> ORGANISM: Artificial Sequence
<220> FEATURE:
<223> OTHER INFORMATION: human chimeric IgG4 HL-Ch3 with mutation

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60
```

-continued

Ser Asn Gly Gln Pro Glu Asn Asn Tyr Lys Thr Thr Pro Pro Val Leu
65 70 75 80

Asp Ser Asp Gly Ser Phe Phe Leu Tyr Ser Arg Leu Thr Val Asp Lys
85 90 95

Ser Arg Trp Gln Glu Gly Asn Val Phe Ser Cys Ser Val Met His Glu
100 105 110

Ala Leu His Asn His Tyr Thr Gln Lys Ser Leu Ser Leu Ser Leu Gly
115 120 125

Lys

<210> SEQ ID NO 10
<211> LENGTH: 229
<212> TYPE: PRT
<213> ORGANISM: Artificial Sequence
<220> FEATURE:
<223> OTHER INFORMATION: mutated IgG4

<400> SEQUENCE: 10

Glu Ser Lys Tyr Gly Pro Pro Cys Pro Ser Cys Pro Ala Pro Glu Phe
1 5 10 15

Glu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Gln Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 11
<211> LENGTH: 229
<212> TYPE: PRT
<213> ORGANISM: Artificial Sequence
<220> FEATURE:
<223> OTHER INFORMATION: mutated IgG4

<400> SEQUENCE: 11

-continued

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Homo sapiens

```
<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20


<210> SEQ ID NO 14
<211> LENGTH: 27
<212> TYPE: PRT
<213> ORGANISM: Homo sapiens

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 15
<211> LENGTH: 28
<212> TYPE: PRT
<213> ORGANISM: Artificial Sequence
<220> FEATURE:
<223> OTHER INFORMATION: mutated human CD28

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25


<210> SEQ ID NO 16
<211> LENGTH: 22
<212> TYPE: PRT
<213> ORGANISM: Homo sapiens

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20


<210> SEQ ID NO 17
<211> LENGTH: 21
<212> TYPE: PRT
<213> ORGANISM: Homo sapiens

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20


<210> SEQ ID NO 18
<211> LENGTH: 23
<212> TYPE: PRT
<213> ORGANISM: Homo sapiens

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
```

-continued

20

<210> SEQ ID NO 19
<211> LENGTH: 24
<212> TYPE: PRT
<213> ORGANISM: Homo sapiens

<400> SEQUENCE: 19

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 20
<211> LENGTH: 27
<212> TYPE: PRT
<213> ORGANISM: Homo sapiens

<400> SEQUENCE: 20

Ile Ile Ser Phe Phe Leu Ala Leu Thr Ser Thr Ala Leu Leu Phe Leu
1 5 10 15

Leu Phe Phe Leu Thr Leu Arg Phe Ser Val Val
20 25

<210> SEQ ID NO 21
<211> LENGTH: 112
<212> TYPE: PRT
<213> ORGANISM: Homo sapiens

<400> SEQUENCE: 21

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 22
<211> LENGTH: 41
<212> TYPE: PRT
<213> ORGANISM: Homo sapiens

<400> SEQUENCE: 22

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 23
<211> LENGTH: 41

-continued

<212> TYPE: PRT
<213> ORGANISM: Artificial Sequence
<220> FEATURE:
<223> OTHER INFORMATION: mutated CD28

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 25
<211> LENGTH: 42
<212> TYPE: PRT
<213> ORGANISM: Homo sapiens

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 26
<211> LENGTH: 471
<212> TYPE: PRT
<213> ORGANISM: Artificial Sequence
<220> FEATURE:
<223> OTHER INFORMATION: chimeric CLTX-IgG4(EQ)-CD28tm-CD28-zeta
      including signal

<400> SEQUENCE: 26

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
    50                  55                  60

Pro Cys Pro Pro Cys Pro Ala Pro Glu Phe Glu Gly Gly Pro Ser Val
65                  70                  75                  80

Phe Leu Phe Pro Pro Lys Pro Lys Asp Thr Leu Met Ile Ser Arg Thr
                85                  90                  95

-continued

```
Pro Glu Val Thr Cys Val Val Val Asp Val Ser Gln Glu Asp Pro Glu
            100                 105                 110

Val Gln Phe Asn Trp Tyr Val Asp Gly Val Glu Val His Asn Ala Lys
        115                 120                 125

Thr Lys Pro Arg Glu Glu Gln Phe Gln Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Lys Met
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Gly Gly His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Gly Gly Gly Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 27
<211> LENGTH: 371
<212> TYPE: PRT
<213> ORGANISM: Artificial Sequence
<220> FEATURE:
<223> OTHER INFORMATION: chimeric CLTX-IgG4(HL-CH3)-CD28tm-CD28-zeta including signal

<400> SEQUENCE: 27

Met Leu Leu Leu Val Thr Ser Leu Leu Leu Cys Glu Leu Pro His Pro
1 5 10 15

Ala Phe Leu Leu Ile Pro Met Cys Met Pro Cys Phe Thr Thr Asp His
20 25 30

Gln Met Ala Arg Lys Cys Asp Asp Cys Cys Gly Gly Lys Gly Arg Gly
35 40 45

Lys Cys Tyr Gly Pro Gln Cys Leu Cys Arg Glu Ser Lys Tyr Gly Pro
50 55 60

Pro Cys Pro Pro Cys Pro Gly Gly Gly Ser Ser Gly Gly Gly Ser Gly
65 70 75 80

Gly Gln Pro Arg Glu Pro Gln Val Tyr Thr Leu Pro Pro Ser Gln Glu
85 90 95

Glu Met Thr Lys Asn Gln Val Ser Leu Thr Cys Leu Val Lys Gly Phe
100 105 110

Tyr Pro Ser Asp Ile Ala Val Glu Trp Glu Ser Asn Gly Gln Pro Glu
115 120 125

Asn Asn Tyr Lys Thr Thr Pro Pro Val Leu Asp Ser Asp Gly Ser Phe
130 135 140

Phe Leu Tyr Ser Arg Leu Thr Val Asp Lys Ser Arg Trp Gln Glu Gly
145 150 155 160

Asn Val Phe Ser Cys Ser Val Met His Glu Ala Leu His Asn His Tyr
165 170 175

Thr Gln Lys Ser Leu Ser Leu Ser Leu Gly Lys Met Phe Trp Val Leu
180 185 190

Val Val Val Gly Gly Val Leu Ala Cys Tyr Ser Leu Leu Val Thr Val
195 200 205

Ala Phe Ile Ile Phe Trp Val Arg Ser Lys Arg Ser Arg Gly Gly His
210 215 220

Ser Asp Tyr Met Asn Met Thr Pro Arg Arg Pro Gly Pro Thr Arg Lys
225 230 235 240

His Tyr Gln Pro Tyr Ala Pro Pro Arg Asp Phe Ala Ala Tyr Arg Ser
245 250 255

Gly Gly Gly Arg Val Lys Phe Ser Arg Ser Ala Asp Ala Pro Ala Tyr
260 265 270

Gln Gln Gly Gln Asn Gln Leu Tyr Asn Glu Leu Asn Leu Gly Arg Arg
275 280 285

Glu Glu Tyr Asp Val Leu Asp Lys Arg Arg Gly Arg Asp Pro Glu Met
290 295 300

Gly Gly Lys Pro Arg Arg Lys Asn Pro Gln Glu Gly Leu Tyr Asn Glu
305 310 315 320

Leu Gln Lys Asp Lys Met Ala Glu Ala Tyr Ser Glu Ile Gly Met Lys
325 330 335

Gly Glu Arg Arg Arg Gly Lys Gly His Asp Gly Leu Tyr Gln Gly Leu
340 345 350

Ser Thr Ala Thr Lys Asp Thr Tyr Asp Ala Leu His Met Gln Ala Leu
355 360 365

Pro Pro Arg
370

<210> SEQ ID NO 28
<211> LENGTH: 287

<212> TYPE: PRT
<213> ORGANISM: Artificial Sequence
<220> FEATURE:
<223> OTHER INFORMATION: chimeric CLTX-CD8h- CD28tm-CD28-zeta including signal

<400> SEQUENCE: 28

```
Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Thr Thr Thr Pro Ala Pro
    50                  55                  60

Arg Pro Pro Thr Pro Ala Pro Thr Ile Ala Ser Gln Pro Leu Ser Leu
65                  70                  75                  80

Arg Pro Glu Ala Cys Arg Pro Ala Ala Gly Gly Ala Val His Thr Arg
                85                  90                  95

Gly Leu Asp Phe Ala Cys Asp Met Phe Trp Val Leu Val Val Val Gly
            100                 105                 110

Gly Val Leu Ala Cys Tyr Ser Leu Leu Val Thr Val Ala Phe Ile Ile
        115                 120                 125

Phe Trp Val Arg Ser Lys Arg Ser Arg Gly Gly His Ser Asp Tyr Met
    130                 135                 140

Asn Met Thr Pro Arg Arg Pro Gly Pro Thr Arg Lys His Tyr Gln Pro
145                 150                 155                 160

Tyr Ala Pro Pro Arg Asp Phe Ala Ala Tyr Arg Ser Gly Gly Gly Arg
                165                 170                 175

Val Lys Phe Ser Arg Ser Ala Asp Ala Pro Ala Tyr Gln Gln Gly Gln
            180                 185                 190

Asn Gln Leu Tyr Asn Glu Leu Asn Leu Gly Arg Arg Glu Glu Tyr Asp
        195                 200                 205

Val Leu Asp Lys Arg Arg Gly Arg Asp Pro Glu Met Gly Gly Lys Pro
    210                 215                 220

Arg Arg Lys Asn Pro Gln Glu Gly Leu Tyr Asn Glu Leu Gln Lys Asp
225                 230                 235                 240

Lys Met Ala Glu Ala Tyr Ser Glu Ile Gly Met Lys Gly Glu Arg Arg
                245                 250                 255

Arg Gly Lys Gly His Asp Gly Leu Tyr Gln Gly Leu Ser Thr Ala Thr
            260                 265                 270

Lys Asp Thr Tyr Asp Ala Leu His Met Gln Ala Leu Pro Pro Arg
        275                 280                 285
```

<210> SEQ ID NO 29
<211> LENGTH: 254
<212> TYPE: PRT
<213> ORGANISM: Artificial Sequence
<220> FEATURE:
<223> OTHER INFORMATION: chimeric CLTX-IgG4(hinge)-CD28tm-CD28-zeta including signal

<400> SEQUENCE: 29

```
Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30
```

```
Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
    50                  55                  60

Pro Cys Pro Pro Cys Pro Met Phe Trp Val Leu Val Val Val Gly Gly
65                  70                  75                  80

Val Leu Ala Cys Tyr Ser Leu Leu Val Thr Val Ala Phe Ile Ile Phe
                85                  90                  95

Trp Val Arg Ser Lys Arg Ser Arg Gly Gly His Ser Asp Tyr Met Asn
            100                 105                 110

Met Thr Pro Arg Arg Pro Gly Pro Thr Arg Lys His Tyr Gln Pro Tyr
        115                 120                 125

Ala Pro Pro Arg Asp Phe Ala Ala Tyr Arg Ser Gly Gly Gly Arg Val
    130                 135                 140

Lys Phe Ser Arg Ser Ala Asp Ala Pro Ala Tyr Gln Gln Gly Gln Asn
145                 150                 155                 160

Gln Leu Tyr Asn Glu Leu Asn Leu Gly Arg Arg Glu Glu Tyr Asp Val
                165                 170                 175

Leu Asp Lys Arg Arg Gly Arg Asp Pro Glu Met Gly Gly Lys Pro Arg
            180                 185                 190

Arg Lys Asn Pro Gln Glu Gly Leu Tyr Asn Glu Leu Gln Lys Asp Lys
        195                 200                 205

Met Ala Glu Ala Tyr Ser Glu Ile Gly Met Lys Gly Glu Arg Arg Arg
    210                 215                 220

Gly Lys Gly His Asp Gly Leu Tyr Gln Gly Leu Ser Thr Ala Thr Lys
225                 230                 235                 240

Asp Thr Tyr Asp Ala Leu His Met Gln Ala Leu Pro Pro Arg
                245                 250
```

<210> SEQ ID NO 30
<211> LENGTH: 252
<212> TYPE: PRT
<213> ORGANISM: Artificial Sequence
<220> FEATURE:
<223> OTHER INFORMATION: chimeric CLTX-L-CD28tm-CD28-zeta including signal

<400> SEQUENCE: 30

```
Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Gly Gly Gly Ser Ser Gly
    50                  55                  60

Gly Gly Ser Gly Met Phe Trp Val Leu Val Val Val Gly Gly Val Leu
65                  70                  75                  80

Ala Cys Tyr Ser Leu Leu Val Thr Val Ala Phe Ile Ile Phe Trp Val
                85                  90                  95

Arg Ser Lys Arg Ser Arg Gly Gly His Ser Asp Tyr Met Asn Met Thr
            100                 105                 110

Pro Arg Arg Pro Gly Pro Thr Arg Lys His Tyr Gln Pro Tyr Ala Pro
        115                 120                 125

Pro Arg Asp Phe Ala Ala Tyr Arg Ser Gly Gly Gly Arg Val Lys Phe
    130                 135                 140
```

Ser Arg Ser Ala Asp Ala Pro Ala Tyr Gln Gln Gly Gln Asn Gln Leu
145 150 155 160

Tyr Asn Glu Leu Asn Leu Gly Arg Arg Glu Glu Tyr Asp Val Leu Asp
165 170 175

Lys Arg Arg Gly Arg Asp Pro Glu Met Gly Gly Lys Pro Arg Arg Lys
180 185 190

Asn Pro Gln Glu Gly Leu Tyr Asn Glu Leu Gln Lys Asp Lys Met Ala
195 200 205

Glu Ala Tyr Ser Glu Ile Gly Met Lys Gly Glu Arg Arg Arg Gly Lys
210 215 220

Gly His Asp Gly Leu Tyr Gln Gly Leu Ser Thr Ala Thr Lys Asp Thr
225 230 235 240

Tyr Asp Ala Leu His Met Gln Ala Leu Pro Pro Arg
245 250

<210> SEQ ID NO 31
<211> LENGTH: 516
<212> TYPE: PRT
<213> ORGANISM: Artificial Sequence
<220> FEATURE:
<223> OTHER INFORMATION: chimeric CLTX-IgG4(EQ)-CD28tm-CD28-4-1BBzeta including signal

<400> SEQUENCE: 31

Met Leu Leu Leu Val Thr Ser Leu Leu Leu Cys Glu Leu Pro His Pro
1 5 10 15

Ala Phe Leu Leu Ile Pro Met Cys Met Pro Cys Phe Thr Thr Asp His
20 25 30

Gln Met Ala Arg Lys Cys Asp Asp Cys Cys Gly Gly Lys Gly Arg Gly
35 40 45

Lys Cys Tyr Gly Pro Gln Cys Leu Cys Arg Glu Ser Lys Tyr Gly Pro
50 55 60

Pro Cys Pro Pro Cys Pro Ala Pro Glu Phe Glu Gly Gly Pro Ser Val
65 70 75 80

Phe Leu Phe Pro Pro Lys Pro Lys Asp Thr Leu Met Ile Ser Arg Thr
85 90 95

Pro Glu Val Thr Cys Val Val Val Asp Val Ser Gln Glu Asp Pro Glu
100 105 110

Val Gln Phe Asn Trp Tyr Val Asp Gly Val Glu Val His Asn Ala Lys
115 120 125

Thr Lys Pro Arg Glu Glu Gln Phe Gln Ser Thr Tyr Arg Val Val Ser
130 135 140

Val Leu Thr Val Leu His Gln Asp Trp Leu Asn Gly Lys Glu Tyr Lys
145 150 155 160

Cys Lys Val Ser Asn Lys Gly Leu Pro Ser Ser Ile Glu Lys Thr Ile
165 170 175

Ser Lys Ala Lys Gly Gln Pro Arg Glu Pro Gln Val Tyr Thr Leu Pro
180 185 190

Pro Ser Gln Glu Glu Met Thr Lys Asn Gln Val Ser Leu Thr Cys Leu
195 200 205

Val Lys Gly Phe Tyr Pro Ser Asp Ile Ala Val Glu Trp Glu Ser Asn
210 215 220

Gly Gln Pro Glu Asn Asn Tyr Lys Thr Thr Pro Pro Val Leu Asp Ser
225 230 235 240

Asp Gly Ser Phe Phe Leu Tyr Ser Arg Leu Thr Val Asp Lys Ser Arg

```
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Lys Met
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Gly Gly His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Gly Gly Gly Lys Arg Gly Arg Lys Lys Leu Leu Tyr
        355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
385                 390                 395                 400

Leu Gly Gly Gly Arg Val Lys Phe Ser Arg Ser Ala Asp Ala Pro Ala
                405                 410                 415

Tyr Gln Gln Gly Gln Asn Gln Leu Tyr Asn Glu Leu Asn Leu Gly Arg
            420                 425                 430

Arg Glu Glu Tyr Asp Val Leu Asp Lys Arg Arg Gly Arg Asp Pro Glu
        435                 440                 445

Met Gly Gly Lys Pro Arg Arg Lys Asn Pro Gln Glu Gly Leu Tyr Asn
    450                 455                 460

Glu Leu Gln Lys Asp Lys Met Ala Glu Ala Tyr Ser Glu Ile Gly Met
465                 470                 475                 480

Lys Gly Glu Arg Arg Arg Gly Lys Gly His Asp Gly Leu Tyr Gln Gly
                485                 490                 495

Leu Ser Thr Ala Thr Lys Asp Thr Tyr Asp Ala Leu His Met Gln Ala
            500                 505                 510

Leu Pro Pro Arg
        515


<210> SEQ ID NO 32
<211> LENGTH: 416
<212> TYPE: PRT
<213> ORGANISM: Artificial Sequence
<220> FEATURE:
<223> OTHER INFORMATION: chimeric CLTX-IgG4(HL-CH3)-CD28tm-CD28-4-
      1BBzeta including sequence

<400> SEQUENCE: 32

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
    50                  55                  60

Pro Cys Pro Pro Cys Pro Gly Gly Gly Ser Ser Gly Gly Gly Ser Gly
65                  70                  75                  80
```

-continued

```
Gly Gln Pro Arg Glu Pro Gln Val Tyr Thr Leu Pro Pro Ser Gln Glu
                85                  90                  95

Glu Met Thr Lys Asn Gln Val Ser Leu Thr Cys Leu Val Lys Gly Phe
            100                 105                 110

Tyr Pro Ser Asp Ile Ala Val Glu Trp Glu Ser Asn Gly Gln Pro Glu
        115                 120                 125

Asn Asn Tyr Lys Thr Thr Pro Pro Val Leu Asp Ser Asp Gly Ser Phe
    130                 135                 140

Phe Leu Tyr Ser Arg Leu Thr Val Asp Lys Ser Arg Trp Gln Glu Gly
145                 150                 155                 160

Asn Val Phe Ser Cys Ser Val Met His Glu Ala Leu His Asn His Tyr
                165                 170                 175

Thr Gln Lys Ser Leu Ser Leu Ser Leu Gly Lys Met Phe Trp Val Leu
            180                 185                 190

Val Val Val Gly Gly Val Leu Ala Cys Tyr Ser Leu Leu Val Thr Val
        195                 200                 205

Ala Phe Ile Ile Phe Trp Val Arg Ser Lys Arg Ser Arg Gly Gly His
    210                 215                 220

Ser Asp Tyr Met Asn Met Thr Pro Arg Arg Pro Gly Pro Thr Arg Lys
225                 230                 235                 240

His Tyr Gln Pro Tyr Ala Pro Pro Arg Asp Phe Ala Ala Tyr Arg Ser
                245                 250                 255

Gly Gly Gly Lys Arg Gly Arg Lys Lys Leu Leu Tyr Ile Phe Lys Gln
            260                 265                 270

Pro Phe Met Arg Pro Val Gln Thr Thr Gln Glu Glu Asp Gly Cys Ser
        275                 280                 285

Cys Arg Phe Pro Glu Glu Glu Glu Gly Gly Cys Glu Leu Gly Gly Gly
    290                 295                 300

Arg Val Lys Phe Ser Arg Ser Ala Asp Ala Pro Ala Tyr Gln Gln Gly
305                 310                 315                 320

Gln Asn Gln Leu Tyr Asn Glu Leu Asn Leu Gly Arg Arg Glu Glu Tyr
                325                 330                 335

Asp Val Leu Asp Lys Arg Arg Gly Arg Asp Pro Glu Met Gly Gly Lys
            340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
    370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415


<210> SEQ ID NO 33
<211> LENGTH: 332
<212> TYPE: PRT
<213> ORGANISM: Artificial Sequence
<220> FEATURE:
<223> OTHER INFORMATION: chimeric CLTX-CD8h-CD28tm-CD28-4-1BB-zeta
      including sequence

<400> SEQUENCE: 33

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30
```

```
Gln Met Ala Arg Lys Cys Asp Asp Cys Cys Gly Gly Lys Gly Arg Gly
        35                  40                  45

Lys Cys Tyr Gly Pro Gln Cys Leu Cys Arg Thr Thr Thr Pro Ala Pro
    50                  55                  60

Arg Pro Pro Thr Pro Ala Pro Thr Ile Ala Ser Gln Pro Leu Ser Leu
65                  70                  75                  80

Arg Pro Glu Ala Cys Arg Pro Ala Ala Gly Gly Ala Val His Thr Arg
                85                  90                  95

Gly Leu Asp Phe Ala Cys Asp Met Phe Trp Val Leu Val Val Val Gly
            100                 105                 110

Gly Val Leu Ala Cys Tyr Ser Leu Leu Val Thr Val Ala Phe Ile Ile
        115                 120                 125

Phe Trp Val Arg Ser Lys Arg Ser Arg Gly Gly His Ser Asp Tyr Met
    130                 135                 140

Asn Met Thr Pro Arg Arg Pro Gly Pro Thr Arg Lys His Tyr Gln Pro
145                 150                 155                 160

Tyr Ala Pro Pro Arg Asp Phe Ala Ala Tyr Arg Ser Gly Gly Gly Lys
                165                 170                 175

Arg Gly Arg Lys Lys Leu Leu Tyr Ile Phe Lys Gln Pro Phe Met Arg
            180                 185                 190

Pro Val Gln Thr Thr Gln Glu Glu Asp Gly Cys Ser Cys Arg Phe Pro
        195                 200                 205

Glu Glu Glu Glu Gly Gly Cys Glu Leu Gly Gly Gly Arg Val Lys Phe
    210                 215                 220

Ser Arg Ser Ala Asp Ala Pro Ala Tyr Gln Gln Gly Gln Asn Gln Leu
225                 230                 235                 240

Tyr Asn Glu Leu Asn Leu Gly Arg Arg Glu Glu Tyr Asp Val Leu Asp
                245                 250                 255

Lys Arg Arg Gly Arg Asp Pro Glu Met Gly Gly Lys Pro Arg Arg Lys
            260                 265                 270

Asn Pro Gln Glu Gly Leu Tyr Asn Glu Leu Gln Lys Asp Lys Met Ala
        275                 280                 285

Glu Ala Tyr Ser Glu Ile Gly Met Lys Gly Glu Arg Arg Arg Gly Lys
    290                 295                 300

Gly His Asp Gly Leu Tyr Gln Gly Leu Ser Thr Ala Thr Lys Asp Thr
305                 310                 315                 320

Tyr Asp Ala Leu His Met Gln Ala Leu Pro Pro Arg
                325                 330


<210> SEQ ID NO 34
<211> LENGTH: 299
<212> TYPE: PRT
<213> ORGANISM: Artificial Sequence
<220> FEATURE:
<223> OTHER INFORMATION: chimeric LTX-IgG4(hinge)-CD28tm-CD28-4-1BBzeta
      including sequence

<400> SEQUENCE: 34

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
```

```
    50                  55                  60

Pro Cys Pro Pro Cys Pro Met Phe Trp Val Leu Val Val Val Gly Gly
65                  70                  75                  80

Val Leu Ala Cys Tyr Ser Leu Leu Val Thr Val Ala Phe Ile Ile Phe
                85                  90                  95

Trp Val Arg Ser Lys Arg Ser Arg Gly Gly His Ser Asp Tyr Met Asn
            100                 105                 110

Met Thr Pro Arg Arg Pro Gly Pro Thr Arg Lys His Tyr Gln Pro Tyr
        115                 120                 125

Ala Pro Pro Arg Asp Phe Ala Ala Tyr Arg Ser Gly Gly Gly Lys Arg
    130                 135                 140

Gly Arg Lys Lys Leu Leu Tyr Ile Phe Lys Gln Pro Phe Met Arg Pro
145                 150                 155                 160

Val Gln Thr Thr Gln Glu Glu Asp Gly Cys Ser Cys Arg Phe Pro Glu
                165                 170                 175

Glu Glu Glu Gly Gly Cys Glu Leu Gly Gly Gly Arg Val Lys Phe Ser
            180                 185                 190

Arg Ser Ala Asp Ala Pro Ala Tyr Gln Gln Gly Gln Asn Gln Leu Tyr
        195                 200                 205

Asn Glu Leu Asn Leu Gly Arg Arg Glu Glu Tyr Asp Val Leu Asp Lys
    210                 215                 220

Arg Arg Gly Arg Asp Pro Glu Met Gly Gly Lys Pro Arg Arg Lys Asn
225                 230                 235                 240

Pro Gln Glu Gly Leu Tyr Asn Glu Leu Gln Lys Asp Lys Met Ala Glu
                245                 250                 255

Ala Tyr Ser Glu Ile Gly Met Lys Gly Glu Arg Arg Arg Gly Lys Gly
            260                 265                 270

His Asp Gly Leu Tyr Gln Gly Leu Ser Thr Ala Thr Lys Asp Thr Tyr
        275                 280                 285

Asp Ala Leu His Met Gln Ala Leu Pro Pro Arg
    290                 295


<210> SEQ ID NO 35
<211> LENGTH: 297
<212> TYPE: PRT
<213> ORGANISM: Artificial Sequence
<220> FEATURE:
<223> OTHER INFORMATION: chimeric CLTX-L-CD28tm-CD28-4-1BB-zeta
      including sequence

<400> SEQUENCE: 35

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Gly Gly Gly Ser Ser Gly
    50                  55                  60

Gly Gly Ser Gly Met Phe Trp Val Leu Val Val Val Gly Gly Val Leu
65                  70                  75                  80

Ala Cys Tyr Ser Leu Leu Val Thr Val Ala Phe Ile Ile Phe Trp Val
                85                  90                  95

Arg Ser Lys Arg Ser Arg Gly Gly His Ser Asp Tyr Met Asn Met Thr
            100                 105                 110
```

-continued

```
Pro Arg Arg Pro Gly Pro Thr Arg Lys His Tyr Gln Pro Tyr Ala Pro
        115                 120                 125

Pro Arg Asp Phe Ala Ala Tyr Arg Ser Gly Gly Gly Lys Arg Gly Arg
    130                 135                 140

Lys Lys Leu Leu Tyr Ile Phe Lys Gln Pro Phe Met Arg Pro Val Gln
145                 150                 155                 160

Thr Thr Gln Glu Glu Asp Gly Cys Ser Cys Arg Phe Pro Glu Glu Glu
                165                 170                 175

Glu Gly Gly Cys Glu Leu Gly Gly Gly Arg Val Lys Phe Ser Arg Ser
            180                 185                 190

Ala Asp Ala Pro Ala Tyr Gln Gln Gly Gln Asn Gln Leu Tyr Asn Glu
        195                 200                 205

Leu Asn Leu Gly Arg Arg Glu Glu Tyr Asp Val Leu Asp Lys Arg Arg
    210                 215                 220

Gly Arg Asp Pro Glu Met Gly Gly Lys Pro Arg Arg Lys Asn Pro Gln
225                 230                 235                 240

Glu Gly Leu Tyr Asn Glu Leu Gln Lys Asp Lys Met Ala Glu Ala Tyr
                245                 250                 255

Ser Glu Ile Gly Met Lys Gly Glu Arg Arg Arg Gly Lys Gly His Asp
            260                 265                 270

Gly Leu Tyr Gln Gly Leu Ser Thr Ala Thr Lys Asp Thr Tyr Asp Ala
        275                 280                 285

Leu His Met Gln Ala Leu Pro Pro Arg
    290                 295


<210> SEQ ID NO 36
<211> LENGTH: 466
<212> TYPE: PRT
<213> ORGANISM: Artificial Sequence
<220> FEATURE:
<223> OTHER INFORMATION: chimeric CLTX-IgG4(EQ)-CD4tm-4-1BB-zeta
      including sequence

<400> SEQUENCE: 36

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
    50                  55                  60

Pro Cys Pro Pro Cys Pro Ala Pro Glu Phe Glu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser Gln Glu Asp Pro Glu
            100                 105                 110

Val Gln Phe Asn Trp Tyr Val Asp Gly Val Glu Val His Asn Ala Lys
        115                 120                 125

Thr Lys Pro Arg Glu Glu Gln Phe Gln Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
                165                 170                 175
```

```
Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Lys Met
        275                 280                 285

Ala Leu Ile Val Leu Gly Gly Val Ala Gly Leu Leu Leu Phe Ile Gly
    290                 295                 300

Leu Gly Ile Phe Phe Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Glu Gly Gly Cys Glu Leu Gly
            340                 345                 350

Gly Gly Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465


<210> SEQ ID NO 37
<211> LENGTH: 366
<212> TYPE: PRT
<213> ORGANISM: Artificial Sequence
<220> FEATURE:
<223> OTHER INFORMATION: chimeric CLTX-IgG4(HL-CH3)-CD4tm-4-1BB-zeta
      including sequence

<400> SEQUENCE: 37

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
```

-continued

```
    50                  55                  60

Pro Cys Pro Pro Cys Pro Gly Gly Gly Ser Ser Gly Gly Gly Ser Gly
65                  70                  75                  80

Gly Gln Pro Arg Glu Pro Gln Val Tyr Thr Leu Pro Pro Ser Gln Glu
                85                  90                  95

Glu Met Thr Lys Asn Gln Val Ser Leu Thr Cys Leu Val Lys Gly Phe
            100                 105                 110

Tyr Pro Ser Asp Ile Ala Val Glu Trp Glu Ser Asn Gly Gln Pro Glu
        115                 120                 125

Asn Asn Tyr Lys Thr Thr Pro Pro Val Leu Asp Ser Asp Gly Ser Phe
    130                 135                 140

Phe Leu Tyr Ser Arg Leu Thr Val Asp Lys Ser Arg Trp Gln Glu Gly
145                 150                 155                 160

Asn Val Phe Ser Cys Ser Val Met His Glu Ala Leu His Asn His Tyr
                165                 170                 175

Thr Gln Lys Ser Leu Ser Leu Ser Leu Gly Lys Met Ala Leu Ile Val
            180                 185                 190

Leu Gly Gly Val Ala Gly Leu Leu Leu Phe Ile Gly Leu Gly Ile Phe
        195                 200                 205

Phe Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Gly Gly Gly Arg Val
                245                 250                 255

Lys Phe Ser Arg Ser Ala Asp Ala Pro Ala Tyr Gln Gln Gly Gln Asn
            260                 265                 270

Gln Leu Tyr Asn Glu Leu Asn Leu Gly Arg Arg Glu Glu Tyr Asp Val
        275                 280                 285

Leu Asp Lys Arg Arg Gly Arg Asp Pro Glu Met Gly Gly Lys Pro Arg
    290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
        355                 360                 365


<210> SEQ ID NO 38
<211> LENGTH: 288
<212> TYPE: PRT
<213> ORGANISM: Artificial Sequence
<220> FEATURE:
<223> OTHER INFORMATION: chimeric CLTX-CD8h- CD28tm-4-1BB-zeta including
      sequence

<400> SEQUENCE: 38

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45
```

```
Lys Cys Tyr Gly Pro Gln Cys Leu Cys Arg Thr Thr Thr Pro Ala Pro
    50                  55                  60

Arg Pro Pro Thr Pro Ala Pro Thr Ile Ala Ser Gln Pro Leu Ser Leu
65                  70                  75                  80

Arg Pro Glu Ala Cys Arg Pro Ala Ala Gly Gly Ala Val His Thr Arg
                85                  90                  95

Gly Leu Asp Phe Ala Cys Asp Met Phe Trp Val Leu Val Val Val Gly
            100                 105                 110

Gly Val Leu Ala Cys Tyr Ser Leu Leu Val Thr Val Ala Phe Ile Ile
        115                 120                 125

Phe Trp Val Lys Arg Gly Arg Lys Lys Leu Leu Tyr Ile Phe Lys Gln
    130                 135                 140

Pro Phe Met Arg Pro Val Gln Thr Thr Gln Glu Glu Asp Gly Cys Ser
145                 150                 155                 160

Cys Arg Phe Pro Glu Glu Glu Glu Gly Gly Cys Glu Leu Gly Gly Gly
                165                 170                 175

Arg Val Lys Phe Ser Arg Ser Ala Asp Ala Pro Ala Tyr Gln Gln Gly
            180                 185                 190

Gln Asn Gln Leu Tyr Asn Glu Leu Asn Leu Gly Arg Arg Glu Glu Tyr
        195                 200                 205

Asp Val Leu Asp Lys Arg Arg Gly Arg Asp Pro Glu Met Gly Gly Lys
    210                 215                 220

Pro Arg Arg Lys Asn Pro Gln Glu Gly Leu Tyr Asn Glu Leu Gln Lys
225                 230                 235                 240

Asp Lys Met Ala Glu Ala Tyr Ser Glu Ile Gly Met Lys Gly Glu Arg
                245                 250                 255

Arg Arg Gly Lys Gly His Asp Gly Leu Tyr Gln Gly Leu Ser Thr Ala
            260                 265                 270

Thr Lys Asp Thr Tyr Asp Ala Leu His Met Gln Ala Leu Pro Pro Arg
        275                 280                 285


<210> SEQ ID NO 39
<211> LENGTH: 255
<212> TYPE: PRT
<213> ORGANISM: Artificial Sequence
<220> FEATURE:
<223> OTHER INFORMATION: chimeric CLTX-IgG4(hinge)-CD28tm-4-1BB-zeta
      including sequence

<400> SEQUENCE: 39

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Glu Ser Lys Tyr Gly Pro
    50                  55                  60

Pro Cys Pro Pro Cys Pro Met Phe Trp Val Leu Val Val Val Gly Gly
65                  70                  75                  80

Val Leu Ala Cys Tyr Ser Leu Leu Val Thr Val Ala Phe Ile Ile Phe
                85                  90                  95

Trp Val Lys Arg Gly Arg Lys Lys Leu Leu Tyr Ile Phe Lys Gln Pro
            100                 105                 110

Phe Met Arg Pro Val Gln Thr Thr Gln Glu Glu Asp Gly Cys Ser Cys
        115                 120                 125
```

```
Arg Phe Pro Glu Glu Glu Glu Gly Gly Cys Glu Leu Gly Gly Gly Arg
    130                 135                 140

Val Lys Phe Ser Arg Ser Ala Asp Ala Pro Ala Tyr Gln Gln Gly Gln
145                 150                 155                 160

Asn Gln Leu Tyr Asn Glu Leu Asn Leu Gly Arg Arg Glu Glu Tyr Asp
                165                 170                 175

Val Leu Asp Lys Arg Arg Gly Arg Asp Pro Glu Met Gly Gly Lys Pro
            180                 185                 190

Arg Arg Lys Asn Pro Gln Glu Gly Leu Tyr Asn Glu Leu Gln Lys Asp
        195                 200                 205

Lys Met Ala Glu Ala Tyr Ser Glu Ile Gly Met Lys Gly Glu Arg Arg
    210                 215                 220

Arg Gly Lys Gly His Asp Gly Leu Tyr Gln Gly Leu Ser Thr Ala Thr
225                 230                 235                 240

Lys Asp Thr Tyr Asp Ala Leu His Met Gln Ala Leu Pro Pro Arg
                245                 250                 255


<210> SEQ ID NO 40
<211> LENGTH: 253
<212> TYPE: PRT
<213> ORGANISM: Artificial Sequence
<220> FEATURE:
<223> OTHER INFORMATION: chimeric CLTX-L-CD28tm-4-1BB-zeta including
      sequence

<400> SEQUENCE: 40

Met Leu Leu Leu Val Thr Ser Leu Leu Leu Cys Glu Leu Pro His Pro
1               5                   10                  15

Ala Phe Leu Leu Ile Pro Met Cys Met Pro Cys Phe Thr Thr Asp His
            20                  25                  30

Gln Met Ala Arg Lys Cys Asp Asp Cys Cys Gly Gly Lys Gly Arg Gly
        35                  40                  45

Lys Cys Tyr Gly Pro Gln Cys Leu Cys Arg Gly Gly Gly Ser Ser Gly
    50                  55                  60

Gly Gly Ser Gly Met Phe Trp Val Leu Val Val Val Gly Gly Val Leu
65                  70                  75                  80

Ala Cys Tyr Ser Leu Leu Val Thr Val Ala Phe Ile Ile Phe Trp Val
                85                  90                  95

Lys Arg Gly Arg Lys Lys Leu Leu Tyr Ile Phe Lys Gln Pro Phe Met
            100                 105                 110

Arg Pro Val Gln Thr Thr Gln Glu Glu Asp Gly Cys Ser Cys Arg Phe
        115                 120                 125

Pro Glu Glu Glu Glu Gly Gly Cys Glu Leu Gly Gly Gly Arg Val Lys
    130                 135                 140

Phe Ser Arg Ser Ala Asp Ala Pro Ala Tyr Gln Gln Gly Gln Asn Gln
145                 150                 155                 160

Leu Tyr Asn Glu Leu Asn Leu Gly Arg Arg Glu Glu Tyr Asp Val Leu
                165                 170                 175

Asp Lys Arg Arg Gly Arg Asp Pro Glu Met Gly Gly Lys Pro Arg Arg
            180                 185                 190

Lys Asn Pro Gln Glu Gly Leu Tyr Asn Glu Leu Gln Lys Asp Lys Met
        195                 200                 205

Ala Glu Ala Tyr Ser Glu Ile Gly Met Lys Gly Glu Arg Arg Arg Gly
    210                 215                 220

Lys Gly His Asp Gly Leu Tyr Gln Gly Leu Ser Thr Ala Thr Lys Asp
```

```
225                 230                 235                 240

Thr Tyr Asp Ala Leu His Met Gln Ala Leu Pro Pro Arg
                245                 250


<210> SEQ ID NO 41
<211> LENGTH: 449
<212> TYPE: PRT
<213> ORGANISM: Artificial Sequence
<220> FEATURE:
<223> OTHER INFORMATION: chimeric CLTX-IgG4(EQ)-CD28tm-CD28-zeta
      excluding signal

<400> SEQUENCE: 41

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
        35                  40                  45

Ala Pro Glu Phe Glu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser Gln Glu Asp Pro Glu Val Gln Phe Asn Trp Tyr
                85                  90                  95

Val Asp Gly Val Glu Val His Asn Ala Lys Thr Lys Pro Arg Glu Glu
            100                 105                 110

Gln Phe Gln Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Gly Leu Pro Ser Ser Ile Glu Lys Thr Ile Ser Lys Ala Lys Gly Gln
145                 150                 155                 160

Pro Arg Glu Pro Gln Val Tyr Thr Leu Pro Pro Ser Gln Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Met Phe Trp Val Leu Val Val
            260                 265                 270

Val Gly Gly Val Leu Ala Cys Tyr Ser Leu Leu Val Thr Val Ala Phe
        275                 280                 285

Ile Ile Phe Trp Val Arg Ser Lys Arg Ser Arg Gly Gly His Ser Asp
    290                 295                 300

Tyr Met Asn Met Thr Pro Arg Arg Pro Gly Pro Thr Arg Lys His Tyr
305                 310                 315                 320

Gln Pro Tyr Ala Pro Pro Arg Asp Phe Ala Ala Tyr Arg Ser Gly Gly
                325                 330                 335
```

-continued

```
Gly Arg Val Lys Phe Ser Arg Ser Ala Asp Ala Pro Ala Tyr Gln Gln
            340                 345                 350

Gly Gln Asn Gln Leu Tyr Asn Glu Leu Asn Leu Gly Arg Arg Glu Glu
        355                 360                 365

Tyr Asp Val Leu Asp Lys Arg Arg Gly Arg Asp Pro Glu Met Gly Gly
    370                 375                 380

Lys Pro Arg Arg Lys Asn Pro Gln Glu Gly Leu Tyr Asn Glu Leu Gln
385                 390                 395                 400

Lys Asp Lys Met Ala Glu Ala Tyr Ser Glu Ile Gly Met Lys Gly Glu
                405                 410                 415

Arg Arg Arg Gly Lys Gly His Asp Gly Leu Tyr Gln Gly Leu Ser Thr
            420                 425                 430

Ala Thr Lys Asp Thr Tyr Asp Ala Leu His Met Gln Ala Leu Pro Pro
        435                 440                 445

Arg


<210> SEQ ID NO 42
<211> LENGTH: 349
<212> TYPE: PRT
<213> ORGANISM: Artificial Sequence
<220> FEATURE:
<223> OTHER INFORMATION: chimeric CLTX-IgG4(HL-CH3)-CD28tm-CD28-zeta
      excluding signal

<400> SEQUENCE: 42

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
        35                  40                  45

Gly Gly Gly Ser Ser Gly Gly Gly Ser Gly Gly Gln Pro Arg Glu Pro
    50                  55                  60

Gln Val Tyr Thr Leu Pro Pro Ser Gln Glu Glu Met Thr Lys Asn Gln
65                  70                  75                  80

Val Ser Leu Thr Cys Leu Val Lys Gly Phe Tyr Pro Ser Asp Ile Ala
                85                  90                  95

Val Glu Trp Glu Ser Asn Gly Gln Pro Glu Asn Asn Tyr Lys Thr Thr
            100                 105                 110

Pro Pro Val Leu Asp Ser Asp Gly Ser Phe Phe Leu Tyr Ser Arg Leu
        115                 120                 125

Thr Val Asp Lys Ser Arg Trp Gln Glu Gly Asn Val Phe Ser Cys Ser
    130                 135                 140

Val Met His Glu Ala Leu His Asn His Tyr Thr Gln Lys Ser Leu Ser
145                 150                 155                 160

Leu Ser Leu Gly Lys Met Phe Trp Val Leu Val Val Val Gly Gly Val
                165                 170                 175

Leu Ala Cys Tyr Ser Leu Leu Val Thr Val Ala Phe Ile Ile Phe Trp
            180                 185                 190

Val Arg Ser Lys Arg Ser Arg Gly Gly His Ser Asp Tyr Met Asn Met
        195                 200                 205

Thr Pro Arg Arg Pro Gly Pro Thr Arg Lys His Tyr Gln Pro Tyr Ala
    210                 215                 220

Pro Pro Arg Asp Phe Ala Ala Tyr Arg Ser Gly Gly Gly Arg Val Lys
225                 230                 235                 240
```

-continued

```
Phe Ser Arg Ser Ala Asp Ala Pro Ala Tyr Gln Gln Gly Gln Asn Gln
                245                 250                 255

Leu Tyr Asn Glu Leu Asn Leu Gly Arg Arg Glu Glu Tyr Asp Val Leu
            260                 265                 270

Asp Lys Arg Arg Gly Arg Asp Pro Glu Met Gly Gly Lys Pro Arg Arg
        275                 280                 285

Lys Asn Pro Gln Glu Gly Leu Tyr Asn Glu Leu Gln Lys Asp Lys Met
    290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg
            340                 345


<210> SEQ ID NO 43
<211> LENGTH: 265
<212> TYPE: PRT
<213> ORGANISM: Artificial Sequence
<220> FEATURE:
<223> OTHER INFORMATION: chimeric CLTX-CD8h- CD28tm-CD28-zeta excluding
      signal

<400> SEQUENCE: 43

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Thr Thr Thr Pro Ala Pro Arg Pro Pro Thr Pro Ala
        35                  40                  45

Pro Thr Ile Ala Ser Gln Pro Leu Ser Leu Arg Pro Glu Ala Cys Arg
    50                  55                  60

Pro Ala Ala Gly Gly Ala Val His Thr Arg Gly Leu Asp Phe Ala Cys
65                  70                  75                  80

Asp Met Phe Trp Val Leu Val Val Val Gly Gly Val Leu Ala Cys Tyr
                85                  90                  95

Ser Leu Leu Val Thr Val Ala Phe Ile Ile Phe Trp Val Arg Ser Lys
            100                 105                 110

Arg Ser Arg Gly Gly His Ser Asp Tyr Met Asn Met Thr Pro Arg Arg
        115                 120                 125

Pro Gly Pro Thr Arg Lys His Tyr Gln Pro Tyr Ala Pro Pro Arg Asp
    130                 135                 140

Phe Ala Ala Tyr Arg Ser Gly Gly Gly Arg Val Lys Phe Ser Arg Ser
145                 150                 155                 160

Ala Asp Ala Pro Ala Tyr Gln Gln Gly Gln Asn Gln Leu Tyr Asn Glu
                165                 170                 175

Leu Asn Leu Gly Arg Arg Glu Glu Tyr Asp Val Leu Asp Lys Arg Arg
            180                 185                 190

Gly Arg Asp Pro Glu Met Gly Gly Lys Pro Arg Arg Lys Asn Pro Gln
        195                 200                 205

Glu Gly Leu Tyr Asn Glu Leu Gln Lys Asp Lys Met Ala Glu Ala Tyr
    210                 215                 220

Ser Glu Ile Gly Met Lys Gly Glu Arg Arg Arg Gly Lys Gly His Asp
225                 230                 235                 240

Gly Leu Tyr Gln Gly Leu Ser Thr Ala Thr Lys Asp Thr Tyr Asp Ala
                245                 250                 255
```

```
Leu His Met Gln Ala Leu Pro Pro Arg
            260                 265


<210> SEQ ID NO 44
<211> LENGTH: 232
<212> TYPE: PRT
<213> ORGANISM: Artificial Sequence
<220> FEATURE:
<223> OTHER INFORMATION: Chimeric CLTX-IgG4(hinge)-CD28tm-CD28-zeta
      excluding signal

<400> SEQUENCE: 44

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
        35                  40                  45

Met Phe Trp Val Leu Val Val Val Gly Gly Val Leu Ala Cys Tyr Ser
    50                  55                  60

Leu Leu Val Thr Val Ala Phe Ile Ile Phe Trp Val Arg Ser Lys Arg
65                  70                  75                  80

Ser Arg Gly Gly His Ser Asp Tyr Met Asn Met Thr Pro Arg Arg Pro
                85                  90                  95

Gly Pro Thr Arg Lys His Tyr Gln Pro Tyr Ala Pro Pro Arg Asp Phe
            100                 105                 110

Ala Ala Tyr Arg Ser Gly Gly Gly Arg Val Lys Phe Ser Arg Ser Ala
        115                 120                 125

Asp Ala Pro Ala Tyr Gln Gln Gly Gln Asn Gln Leu Tyr Asn Glu Leu
    130                 135                 140

Asn Leu Gly Arg Arg Glu Glu Tyr Asp Val Leu Asp Lys Arg Arg Gly
145                 150                 155                 160

Arg Asp Pro Glu Met Gly Gly Lys Pro Arg Arg Lys Asn Pro Gln Glu
                165                 170                 175

Gly Leu Tyr Asn Glu Leu Gln Lys Asp Lys Met Ala Glu Ala Tyr Ser
            180                 185                 190

Glu Ile Gly Met Lys Gly Glu Arg Arg Arg Gly Lys Gly His Asp Gly
        195                 200                 205

Leu Tyr Gln Gly Leu Ser Thr Ala Thr Lys Asp Thr Tyr Asp Ala Leu
    210                 215                 220

His Met Gln Ala Leu Pro Pro Arg
225                 230


<210> SEQ ID NO 45
<211> LENGTH: 230
<212> TYPE: PRT
<213> ORGANISM: Artificial Sequence
<220> FEATURE:
<223> OTHER INFORMATION: chimeric CLTX-L-CD28tm-CD28-zeta excluding
      signal

<400> SEQUENCE: 45

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Gly Gly Gly Ser Ser Gly Gly Gly Ser Gly Met Phe
        35                  40                  45
```

Trp Val Leu Val Val Val Gly Gly Val Leu Ala Cys Tyr Ser Leu Leu
50 55 60

Val Thr Val Ala Phe Ile Ile Phe Trp Val Arg Ser Lys Arg Ser Arg
65 70 75 80

Gly Gly His Ser Asp Tyr Met Asn Met Thr Pro Arg Arg Pro Gly Pro
85 90 95

Thr Arg Lys His Tyr Gln Pro Tyr Ala Pro Pro Arg Asp Phe Ala Ala
100 105 110

Tyr Arg Ser Gly Gly Gly Arg Val Lys Phe Ser Arg Ser Ala Asp Ala
115 120 125

Pro Ala Tyr Gln Gln Gly Gln Asn Gln Leu Tyr Asn Glu Leu Asn Leu
130 135 140

Gly Arg Arg Glu Glu Tyr Asp Val Leu Asp Lys Arg Arg Gly Arg Asp
145 150 155 160

Pro Glu Met Gly Gly Lys Pro Arg Arg Lys Asn Pro Gln Glu Gly Leu
165 170 175

Tyr Asn Glu Leu Gln Lys Asp Lys Met Ala Glu Ala Tyr Ser Glu Ile
180 185 190

Gly Met Lys Gly Glu Arg Arg Arg Gly Lys Gly His Asp Gly Leu Tyr
195 200 205

Gln Gly Leu Ser Thr Ala Thr Lys Asp Thr Tyr Asp Ala Leu His Met
210 215 220

Gln Ala Leu Pro Pro Arg
225 230

<210> SEQ ID NO 46
<211> LENGTH: 494
<212> TYPE: PRT
<213> ORGANISM: Artificial Sequence
<220> FEATURE:
<223> OTHER INFORMATION: chimeric CLTX-IgG4(EQ)-CD28tm-CD28-4-1BBzeta excluding signal

<400> SEQUENCE: 46

Met Cys Met Pro Cys Phe Thr Thr Asp His Gln Met Ala Arg Lys Cys
1 5 10 15

Asp Asp Cys Cys Gly Gly Lys Gly Arg Gly Lys Cys Tyr Gly Pro Gln
20 25 30

Cys Leu Cys Arg Glu Ser Lys Tyr Gly Pro Pro Cys Pro Pro Cys Pro
35 40 45

Ala Pro Glu Phe Glu Gly Gly Pro Ser Val Phe Leu Phe Pro Pro Lys
50 55 60

Pro Lys Asp Thr Leu Met Ile Ser Arg Thr Pro Glu Val Thr Cys Val
65 70 75 80

Val Val Asp Val Ser Gln Glu Asp Pro Glu Val Gln Phe Asn Trp Tyr
85 90 95

Val Asp Gly Val Glu Val His Asn Ala Lys Thr Lys Pro Arg Glu Glu
100 105 110

Gln Phe Gln Ser Thr Tyr Arg Val Val Ser Val Leu Thr Val Leu His
115 120 125

Gln Asp Trp Leu Asn Gly Lys Glu Tyr Lys Cys Lys Val Ser Asn Lys
130 135 140

Gly Leu Pro Ser Ser Ile Glu Lys Thr Ile Ser Lys Ala Lys Gly Gln
145 150 155 160

Pro Arg Glu Pro Gln Val Tyr Thr Leu Pro Pro Ser Gln Glu Glu Met

```
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Met Phe Trp Val Leu Val Val
            260                 265                 270

Val Gly Gly Val Leu Ala Cys Tyr Ser Leu Leu Val Thr Val Ala Phe
        275                 280                 285

Ile Ile Phe Trp Val Arg Ser Lys Arg Ser Arg Gly Gly His Ser Asp
    290                 295                 300

Tyr Met Asn Met Thr Pro Arg Arg Pro Gly Pro Thr Arg Lys His Tyr
305                 310                 315                 320

Gln Pro Tyr Ala Pro Pro Arg Asp Phe Ala Ala Tyr Arg Ser Gly Gly
                325                 330                 335

Gly Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Gly Gly Gly Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 47
<211> LENGTH: 394
<212> TYPE: PRT
<213> ORGANISM: Artificial Sequence
<220> FEATURE:
<223> OTHER INFORMATION: chimeric CLTX-IgG4(HL-CH3)-CD28tm-CD28-4-
      1BBzeta excluding signal

<400> SEQUENCE: 47

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30
```

-continued

```
Cys Leu Cys Arg Glu Ser Lys Tyr Gly Pro Pro Cys Pro Pro Cys Pro
        35                  40                  45

Gly Gly Gly Ser Ser Gly Gly Gly Ser Gly Gly Gln Pro Arg Glu Pro
    50                  55                  60

Gln Val Tyr Thr Leu Pro Pro Ser Gln Glu Glu Met Thr Lys Asn Gln
65                  70                  75                  80

Val Ser Leu Thr Cys Leu Val Lys Gly Phe Tyr Pro Ser Asp Ile Ala
                85                  90                  95

Val Glu Trp Glu Ser Asn Gly Gln Pro Glu Asn Asn Tyr Lys Thr Thr
            100                 105                 110

Pro Pro Val Leu Asp Ser Asp Gly Ser Phe Phe Leu Tyr Ser Arg Leu
        115                 120                 125

Thr Val Asp Lys Ser Arg Trp Gln Glu Gly Asn Val Phe Ser Cys Ser
    130                 135                 140

Val Met His Glu Ala Leu His Asn His Tyr Thr Gln Lys Ser Leu Ser
145                 150                 155                 160

Leu Ser Leu Gly Lys Met Phe Trp Val Leu Val Val Val Gly Gly Val
                165                 170                 175

Leu Ala Cys Tyr Ser Leu Leu Val Thr Val Ala Phe Ile Ile Phe Trp
            180                 185                 190

Val Arg Ser Lys Arg Ser Arg Gly Gly His Ser Asp Tyr Met Asn Met
        195                 200                 205

Thr Pro Arg Arg Pro Gly Pro Thr Arg Lys His Tyr Gln Pro Tyr Ala
    210                 215                 220

Pro Pro Arg Asp Phe Ala Ala Tyr Arg Ser Gly Gly Gly Lys Arg Gly
225                 230                 235                 240

Arg Lys Lys Leu Leu Tyr Ile Phe Lys Gln Pro Phe Met Arg Pro Val
                245                 250                 255

Gln Thr Thr Gln Glu Glu Asp Gly Cys Ser Cys Arg Phe Pro Glu Glu
            260                 265                 270

Glu Glu Gly Gly Cys Glu Leu Gly Gly Gly Arg Val Lys Phe Ser Arg
        275                 280                 285

Ser Ala Asp Ala Pro Ala Tyr Gln Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390
```

```
<210> SEQ ID NO 48
<211> LENGTH: 310
<212> TYPE: PRT
<213> ORGANISM: Artificial Sequence
<220> FEATURE:
<223> OTHER INFORMATION: chimeric CLTX-CD8h-CD28tm-CD28-4-1BB-zeta
      excluding signal

<400> SEQUENCE: 48
```

```
Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Thr Thr Thr Pro Ala Pro Arg Pro Pro Thr Pro Ala
        35                  40                  45

Pro Thr Ile Ala Ser Gln Pro Leu Ser Leu Arg Pro Glu Ala Cys Arg
    50                  55                  60

Pro Ala Ala Gly Gly Ala Val His Thr Arg Gly Leu Asp Phe Ala Cys
65                  70                  75                  80

Asp Met Phe Trp Val Leu Val Val Val Gly Gly Val Leu Ala Cys Tyr
                85                  90                  95

Ser Leu Leu Val Thr Val Ala Phe Ile Ile Phe Trp Val Arg Ser Lys
            100                 105                 110

Arg Ser Arg Gly Gly His Ser Asp Tyr Met Asn Met Thr Pro Arg Arg
        115                 120                 125

Pro Gly Pro Thr Arg Lys His Tyr Gln Pro Tyr Ala Pro Pro Arg Asp
    130                 135                 140

Phe Ala Ala Tyr Arg Ser Gly Gly Gly Lys Arg Gly Arg Lys Lys Leu
145                 150                 155                 160

Leu Tyr Ile Phe Lys Gln Pro Phe Met Arg Pro Val Gln Thr Thr Gln
                165                 170                 175

Glu Glu Asp Gly Cys Ser Cys Arg Phe Pro Glu Glu Glu Glu Gly Gly
            180                 185                 190

Cys Glu Leu Gly Gly Gly Arg Val Lys Phe Ser Arg Ser Ala Asp Ala
        195                 200                 205

Pro Ala Tyr Gln Gln Gly Gln Asn Gln Leu Tyr Asn Glu Leu Asn Leu
    210                 215                 220

Gly Arg Arg Glu Glu Tyr Asp Val Leu Asp Lys Arg Arg Gly Arg Asp
225                 230                 235                 240

Pro Glu Met Gly Gly Lys Pro Arg Arg Lys Asn Pro Gln Glu Gly Leu
                245                 250                 255

Tyr Asn Glu Leu Gln Lys Asp Lys Met Ala Glu Ala Tyr Ser Glu Ile
            260                 265                 270

Gly Met Lys Gly Glu Arg Arg Arg Gly Lys Gly His Asp Gly Leu Tyr
        275                 280                 285

Gln Gly Leu Ser Thr Ala Thr Lys Asp Thr Tyr Asp Ala Leu His Met
    290                 295                 300

Gln Ala Leu Pro Pro Arg
305                 310
```

<210> SEQ ID NO 49
<211> LENGTH: 277
<212> TYPE: PRT
<213> ORGANISM: Artificial Sequence
<220> FEATURE:
<223> OTHER INFORMATION: chimeric LTX-IgG4(hinge)-CD28tm-CD28-4-1BBzeta
excluding signal

<400> SEQUENCE: 49

```
Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
```

```
        35                  40                  45

Met Phe Trp Val Leu Val Val Val Gly Gly Val Leu Ala Cys Tyr Ser
    50                  55                  60

Leu Leu Val Thr Val Ala Phe Ile Ile Phe Trp Val Arg Ser Lys Arg
65                  70                  75                  80

Ser Arg Gly Gly His Ser Asp Tyr Met Asn Met Thr Pro Arg Arg Pro
                85                  90                  95

Gly Pro Thr Arg Lys His Tyr Gln Pro Tyr Ala Pro Pro Arg Asp Phe
            100                 105                 110

Ala Ala Tyr Arg Ser Gly Gly Gly Lys Arg Gly Arg Lys Lys Leu Leu
        115                 120                 125

Tyr Ile Phe Lys Gln Pro Phe Met Arg Pro Val Gln Thr Thr Gln Glu
    130                 135                 140

Glu Asp Gly Cys Ser Cys Arg Phe Pro Glu Glu Glu Glu Gly Gly Cys
145                 150                 155                 160

Glu Leu Gly Gly Gly Arg Val Lys Phe Ser Arg Ser Ala Asp Ala Pro
                165                 170                 175

Ala Tyr Gln Gln Gly Gln Asn Gln Leu Tyr Asn Glu Leu Asn Leu Gly
            180                 185                 190

Arg Arg Glu Glu Tyr Asp Val Leu Asp Lys Arg Arg Gly Arg Asp Pro
        195                 200                 205

Glu Met Gly Gly Lys Pro Arg Arg Lys Asn Pro Gln Glu Gly Leu Tyr
    210                 215                 220

Asn Glu Leu Gln Lys Asp Lys Met Ala Glu Ala Tyr Ser Glu Ile Gly
225                 230                 235                 240

Met Lys Gly Glu Arg Arg Arg Gly Lys Gly His Asp Gly Leu Tyr Gln
                245                 250                 255

Gly Leu Ser Thr Ala Thr Lys Asp Thr Tyr Asp Ala Leu His Met Gln
            260                 265                 270

Ala Leu Pro Pro Arg
        275


<210> SEQ ID NO 50
<211> LENGTH: 275
<212> TYPE: PRT
<213> ORGANISM: Artificial Sequence
<220> FEATURE:
<223> OTHER INFORMATION: chimeric CLTX-L-CD28tm-CD28-4-1BB-zeta
      excluding signal

<400> SEQUENCE: 50

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Gly Gly Gly Ser Ser Gly Gly Gly Ser Gly Met Phe
        35                  40                  45

Trp Val Leu Val Val Val Gly Gly Val Leu Ala Cys Tyr Ser Leu Leu
    50                  55                  60

Val Thr Val Ala Phe Ile Ile Phe Trp Val Arg Ser Lys Arg Ser Arg
65                  70                  75                  80

Gly Gly His Ser Asp Tyr Met Asn Met Thr Pro Arg Arg Pro Gly Pro
                85                  90                  95

Thr Arg Lys His Tyr Gln Pro Tyr Ala Pro Pro Arg Asp Phe Ala Ala
            100                 105                 110
```

-continued

```
Tyr Arg Ser Gly Gly Gly Lys Arg Gly Arg Lys Lys Leu Leu Tyr Ile
        115                 120                 125

Phe Lys Gln Pro Phe Met Arg Pro Val Gln Thr Thr Gln Glu Glu Asp
    130                 135                 140

Gly Cys Ser Cys Arg Phe Pro Glu Glu Glu Glu Gly Gly Cys Glu Leu
145                 150                 155                 160

Gly Gly Gly Arg Val Lys Phe Ser Arg Ser Ala Asp Ala Pro Ala Tyr
                165                 170                 175

Gln Gln Gly Gln Asn Gln Leu Tyr Asn Glu Leu Asn Leu Gly Arg Arg
            180                 185                 190

Glu Glu Tyr Asp Val Leu Asp Lys Arg Arg Gly Arg Asp Pro Glu Met
        195                 200                 205

Gly Gly Lys Pro Arg Arg Lys Asn Pro Gln Glu Gly Leu Tyr Asn Glu
    210                 215                 220

Leu Gln Lys Asp Lys Met Ala Glu Ala Tyr Ser Glu Ile Gly Met Lys
225                 230                 235                 240

Gly Glu Arg Arg Arg Gly Lys Gly His Asp Gly Leu Tyr Gln Gly Leu
                245                 250                 255

Ser Thr Ala Thr Lys Asp Thr Tyr Asp Ala Leu His Met Gln Ala Leu
            260                 265                 270

Pro Pro Arg
        275


<210> SEQ ID NO 51
<211> LENGTH: 444
<212> TYPE: PRT
<213> ORGANISM: Artificial Sequence
<220> FEATURE:
<223> OTHER INFORMATION: chimeric CLTX-IgG4(EQ)-CD4tm-4-1BB-zeta
      excluding signal

<400> SEQUENCE: 51

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
        35                  40                  45

Ala Pro Glu Phe Glu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser Gln Glu Asp Pro Glu Val Gln Phe Asn Trp Tyr
                85                  90                  95

Val Asp Gly Val Glu Val His Asn Ala Lys Thr Lys Pro Arg Glu Glu
            100                 105                 110

Gln Phe Gln Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Gly Leu Pro Ser Ser Ile Glu Lys Thr Ile Ser Lys Ala Lys Gly Gln
145                 150                 155                 160

Pro Arg Glu Pro Gln Val Tyr Thr Leu Pro Pro Ser Gln Glu Glu Met
                165                 170                 175

Thr Lys Asn Gln Val Ser Leu Thr Cys Leu Val Lys Gly Phe Tyr Pro
            180                 185                 190
```

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Met Ala Leu Ile Val Leu Gly
            260                 265                 270

Gly Val Ala Gly Leu Leu Leu Phe Ile Gly Leu Gly Ile Phe Phe Lys
        275                 280                 285

Arg Gly Arg Lys Lys Leu Leu Tyr Ile Phe Lys Gln Pro Phe Met Arg
    290                 295                 300

Pro Val Gln Thr Thr Gln Glu Glu Asp Gly Cys Ser Cys Arg Phe Pro
305                 310                 315                 320

Glu Glu Glu Glu Gly Gly Cys Glu Leu Gly Gly Gly Arg Val Lys Phe
                325                 330                 335

Ser Arg Ser Ala Asp Ala Pro Ala Tyr Gln Gln Gly Gln Asn Gln Leu
            340                 345                 350

Tyr Asn Glu Leu Asn Leu Gly Arg Arg Glu Glu Tyr Asp Val Leu Asp
        355                 360                 365

Lys Arg Arg Gly Arg Asp Pro Glu Met Gly Gly Lys Pro Arg Arg Lys
    370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
            420                 425                 430

Tyr Asp Ala Leu His Met Gln Ala Leu Pro Pro Arg
        435                 440

<210> SEQ ID NO 52
<211> LENGTH: 344
<212> TYPE: PRT
<213> ORGANISM: Artificial Sequence
<220> FEATURE:
<223> OTHER INFORMATION: chimeric CLTX-IgG4(HL-CH3)-CD4tm-4-1BB-zeta
      excluding signal

<400> SEQUENCE: 52

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
        35                  40                  45

Gly Gly Gly Ser Ser Gly Gly Gly Ser Gly Gly Gln Pro Arg Glu Pro
    50                  55                  60

Gln Val Tyr Thr Leu Pro Pro Ser Gln Glu Glu Met Thr Lys Asn Gln
65                  70                  75                  80

Val Ser Leu Thr Cys Leu Val Lys Gly Phe Tyr Pro Ser Asp Ile Ala
                85                  90                  95

Val Glu Trp Glu Ser Asn Gly Gln Pro Glu Asn Asn Tyr Lys Thr Thr

```
            100                 105                 110

Pro Pro Val Leu Asp Ser Asp Gly Ser Phe Phe Leu Tyr Ser Arg Leu
        115                 120                 125

Thr Val Asp Lys Ser Arg Trp Gln Glu Gly Asn Val Phe Ser Cys Ser
    130                 135                 140

Val Met His Glu Ala Leu His Asn His Tyr Thr Gln Lys Ser Leu Ser
145                 150                 155                 160

Leu Ser Leu Gly Lys Met Ala Leu Ile Val Leu Gly Gly Val Ala Gly
                165                 170                 175

Leu Leu Leu Phe Ile Gly Leu Gly Ile Phe Phe Lys Arg Gly Arg Lys
            180                 185                 190

Lys Leu Leu Tyr Ile Phe Lys Gln Pro Phe Met Arg Pro Val Gln Thr
        195                 200                 205

Thr Gln Glu Glu Asp Gly Cys Ser Cys Arg Phe Pro Glu Glu Glu Glu
    210                 215                 220

Gly Gly Cys Glu Leu Gly Gly Gly Arg Val Lys Phe Ser Arg Ser Ala
225                 230                 235                 240

Asp Ala Pro Ala Tyr Gln Gln Gly Gln Asn Gln Leu Tyr Asn Glu Leu
                245                 250                 255

Asn Leu Gly Arg Arg Glu Glu Tyr Asp Val Leu Asp Lys Arg Arg Gly
            260                 265                 270

Arg Asp Pro Glu Met Gly Gly Lys Pro Arg Arg Lys Asn Pro Gln Glu
        275                 280                 285

Gly Leu Tyr Asn Glu Leu Gln Lys Asp Lys Met Ala Glu Ala Tyr Ser
    290                 295                 300

Glu Ile Gly Met Lys Gly Glu Arg Arg Arg Gly Lys Gly His Asp Gly
305                 310                 315                 320

Leu Tyr Gln Gly Leu Ser Thr Ala Thr Lys Asp Thr Tyr Asp Ala Leu
                325                 330                 335

His Met Gln Ala Leu Pro Pro Arg
            340


<210> SEQ ID NO 53
<211> LENGTH: 266
<212> TYPE: PRT
<213> ORGANISM: Artificial Sequence
<220> FEATURE:
<223> OTHER INFORMATION: chimeric CLTX-CD8h- CD28tm-4-1BB-zeta signal

<400> SEQUENCE: 53

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Thr Thr Thr Pro Ala Pro Arg Pro Pro Thr Pro Ala
        35                  40                  45

Pro Thr Ile Ala Ser Gln Pro Leu Ser Leu Arg Pro Glu Ala Cys Arg
    50                  55                  60

Pro Ala Ala Gly Gly Ala Val His Thr Arg Gly Leu Asp Phe Ala Cys
65                  70                  75                  80

Asp Met Phe Trp Val Leu Val Val Val Gly Gly Val Leu Ala Cys Tyr
                85                  90                  95

Ser Leu Leu Val Thr Val Ala Phe Ile Ile Phe Trp Val Lys Arg Gly
            100                 105                 110

Arg Lys Lys Leu Leu Tyr Ile Phe Lys Gln Pro Phe Met Arg Pro Val
```

-continued

```
        115                 120                 125

Gln Thr Thr Gln Glu Glu Asp Gly Cys Ser Cys Arg Phe Pro Glu Glu
    130                 135                 140

Glu Glu Gly Gly Cys Glu Leu Gly Gly Gly Arg Val Lys Phe Ser Arg
145                 150                 155                 160

Ser Ala Asp Ala Pro Ala Tyr Gln Gln Gly Gln Asn Gln Leu Tyr Asn
                165                 170                 175

Glu Leu Asn Leu Gly Arg Arg Glu Glu Tyr Asp Val Leu Asp Lys Arg
            180                 185                 190

Arg Gly Arg Asp Pro Glu Met Gly Gly Lys Pro Arg Arg Lys Asn Pro
        195                 200                 205

Gln Glu Gly Leu Tyr Asn Glu Leu Gln Lys Asp Lys Met Ala Glu Ala
    210                 215                 220

Tyr Ser Glu Ile Gly Met Lys Gly Glu Arg Arg Arg Gly Lys Gly His
225                 230                 235                 240

Asp Gly Leu Tyr Gln Gly Leu Ser Thr Ala Thr Lys Asp Thr Tyr Asp
                245                 250                 255

Ala Leu His Met Gln Ala Leu Pro Pro Arg
            260                 265


<210> SEQ ID NO 54
<211> LENGTH: 233
<212> TYPE: PRT
<213> ORGANISM: Artificial Sequence
<220> FEATURE:
<223> OTHER INFORMATION: chimeric CLTX-IgG4(hinge)-CD28tm-4-1BB-zeta
      excluding signal

<400> SEQUENCE: 54

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Ser Lys Tyr Gly Pro Pro Cys Pro Pro Cys Pro
        35                  40                  45

Met Phe Trp Val Leu Val Val Val Gly Gly Val Leu Ala Cys Tyr Ser
    50                  55                  60

Leu Leu Val Thr Val Ala Phe Ile Ile Phe Trp Val Lys Arg Gly Arg
65                  70                  75                  80

Lys Lys Leu Leu Tyr Ile Phe Lys Gln Pro Phe Met Arg Pro Val Gln
                85                  90                  95

Thr Thr Gln Glu Glu Asp Gly Cys Ser Cys Arg Phe Pro Glu Glu Glu
            100                 105                 110

Glu Gly Gly Cys Glu Leu Gly Gly Gly Arg Val Lys Phe Ser Arg Ser
        115                 120                 125

Ala Asp Ala Pro Ala Tyr Gln Gln Gly Gln Asn Gln Leu Tyr Asn Glu
    130                 135                 140

Leu Asn Leu Gly Arg Arg Glu Glu Tyr Asp Val Leu Asp Lys Arg Arg
145                 150                 155                 160

Gly Arg Asp Pro Glu Met Gly Gly Lys Pro Arg Arg Lys Asn Pro Gln
                165                 170                 175

Glu Gly Leu Tyr Asn Glu Leu Gln Lys Asp Lys Met Ala Glu Ala Tyr
            180                 185                 190

Ser Glu Ile Gly Met Lys Gly Glu Arg Arg Arg Gly Lys Gly His Asp
        195                 200                 205
```

```
Gly Leu Tyr Gln Gly Leu Ser Thr Ala Thr Lys Asp Thr Tyr Asp Ala
    210                 215                 220

Leu His Met Gln Ala Leu Pro Pro Arg
225                 230


<210> SEQ ID NO 55
<211> LENGTH: 231
<212> TYPE: PRT
<213> ORGANISM: Artificial Sequence
<220> FEATURE:
<223> OTHER INFORMATION: chimeric CLTX-L-CD28tm-4-1BB-zeta excluding
      signal

<400> SEQUENCE: 55

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Gly Gly Gly Ser Ser Gly Gly Gly Ser Gly Met Phe
        35                  40                  45

Trp Val Leu Val Val Val Gly Gly Val Leu Ala Cys Tyr Ser Leu Leu
    50                  55                  60

Val Thr Val Ala Phe Ile Ile Phe Trp Val Lys Arg Gly Arg Lys Lys
65                  70                  75                  80

Leu Leu Tyr Ile Phe Lys Gln Pro Phe Met Arg Pro Val Gln Thr Thr
                85                  90                  95

Gln Glu Glu Asp Gly Cys Ser Cys Arg Phe Pro Glu Glu Glu Glu Gly
            100                 105                 110

Gly Cys Glu Leu Gly Gly Gly Arg Val Lys Phe Ser Arg Ser Ala Asp
        115                 120                 125

Ala Pro Ala Tyr Gln Gln Gly Gln Asn Gln Leu Tyr Asn Glu Leu Asn
    130                 135                 140

Leu Gly Arg Arg Glu Glu Tyr Asp Val Leu Asp Lys Arg Arg Gly Arg
145                 150                 155                 160

Asp Pro Glu Met Gly Gly Lys Pro Arg Arg Lys Asn Pro Gln Glu Gly
                165                 170                 175

Leu Tyr Asn Glu Leu Gln Lys Asp Lys Met Ala Glu Ala Tyr Ser Glu
            180                 185                 190

Ile Gly Met Lys Gly Glu Arg Arg Arg Gly Lys Gly His Asp Gly Leu
        195                 200                 205

Tyr Gln Gly Leu Ser Thr Ala Thr Lys Asp Thr Tyr Asp Ala Leu His
    210                 215                 220

Met Gln Ala Leu Pro Pro Arg
225                 230


<210> SEQ ID NO 56
<211> LENGTH: 29
<212> TYPE: PRT
<213> ORGANISM: Leiurus quinquestriatus hebraeus

<400> SEQUENCE: 56

Val Ser Cys Glu Asp Cys Pro Asp His Cys Ser Thr Gln Lys Ala Arg
1               5                   10                  15

Ala Lys Cys Asp Asn Asp Lys Cys Val Cys Glu Pro Ile
            20                  25


<210> SEQ ID NO 57
<211> LENGTH: 34
```

-continued

<212> TYPE: PRT
<213> ORGANISM: Leiurus quinquestriatus hebraeus

<400> SEQUENCE: 57

Cys Gly Pro Cys Phe Thr Thr Asp His Gln Met Glu Gln Lys Cys Ala
1 5 10 15

Glu Cys Cys Gly Gly Ile Gly Lys Cys Tyr Gly Pro Gln Cys Leu Cys
20 25 30

Asn Arg

<210> SEQ ID NO 58
<211> LENGTH: 34
<212> TYPE: PRT
<213> ORGANISM: Androctonus australis

<400> SEQUENCE: 58

Met Cys Ile Pro Cys Phe Thr Thr Asn Pro Asn Met Ala Ala Lys Cys
1 5 10 15

Asn Ala Cys Cys Gly Ser Arg Arg Gly Ser Cys Arg Gly Pro Gln Cys
20 25 30

Ile Cys

<210> SEQ ID NO 59
<211> LENGTH: 35
<212> TYPE: PRT
<213> ORGANISM: Buthus martensii

<400> SEQUENCE: 59

Cys Gly Pro Cys Phe Thr Thr Asp Ala Asn Met Ala Arg Lys Cys Arg
1 5 10 15

Glu Cys Cys Gly Gly Ile Gly Lys Cys Phe Gly Pro Gln Cys Leu Cys
20 25 30

Asn Arg Ile
35

<210> SEQ ID NO 60
<211> LENGTH: 600
<212> TYPE: PRT
<213> ORGANISM: Artificial Sequence
<220> FEATURE:
<223> OTHER INFORMATION: chimeric CTLX-L-CD28tm-41BB-zeta-T2A-CD19

<400> SEQUENCE: 60

Met Leu Leu Leu Val Thr Ser Leu Leu Leu Cys Glu Leu Pro His Pro
1 5 10 15

Ala Phe Leu Leu Ile Pro Met Cys Met Pro Cys Phe Thr Thr Asp His
20 25 30

Gln Met Ala Arg Lys Cys Asp Asp Cys Cys Gly Gly Lys Gly Arg Gly
35 40 45

Lys Cys Tyr Gly Pro Gln Cys Leu Cys Arg Gly Gly Gly Ser Ser Gly
50 55 60

Gly Gly Ser Gly Met Phe Trp Val Leu Val Val Val Gly Gly Val Leu
65 70 75 80

Ala Cys Tyr Ser Leu Leu Val Thr Val Ala Phe Ile Ile Phe Trp Val
85 90 95

Lys Arg Gly Arg Lys Lys Leu Leu Tyr Ile Phe Lys Gln Pro Phe Met
100 105 110

Arg Pro Val Gln Thr Thr Gln Glu Glu Asp Gly Cys Ser Cys Arg Phe
115 120 125

-continued

```
Pro Glu Glu Glu Glu Gly Gly Cys Glu Leu Gly Gly Gly Arg Val Lys
    130                 135                 140

Phe Ser Arg Ser Ala Asp Ala Pro Ala Tyr Gln Gln Gly Gln Asn Gln
145                 150                 155                 160

Leu Tyr Asn Glu Leu Asn Leu Gly Arg Arg Glu Glu Tyr Asp Val Leu
                165                 170                 175

Asp Lys Arg Arg Gly Arg Asp Pro Glu Met Gly Gly Lys Pro Arg Arg
            180                 185                 190

Lys Asn Pro Gln Glu Gly Leu Tyr Asn Glu Leu Gln Lys Asp Lys Met
        195                 200                 205

Ala Glu Ala Tyr Ser Glu Ile Gly Met Lys Gly Glu Arg Arg Arg Gly
    210                 215                 220

Lys Gly His Asp Gly Leu Tyr Gln Gly Leu Ser Thr Ala Thr Lys Asp
225                 230                 235                 240

Thr Tyr Asp Ala Leu His Met Gln Ala Leu Pro Pro Arg Leu Glu Gly
                245                 250                 255

Gly Gly Glu Gly Arg Gly Ser Leu Leu Thr Cys Gly Asp Val Glu Glu
            260                 265                 270

Asn Pro Gly Pro Arg Met Pro Pro Pro Arg Leu Leu Phe Phe Leu Leu
        275                 280                 285

Phe Leu Thr Pro Met Glu Val Arg Pro Glu Glu Pro Leu Val Val Lys
    290                 295                 300

Val Glu Glu Gly Asp Asn Ala Val Leu Gln Cys Leu Lys Gly Thr Ser
305                 310                 315                 320

Asp Gly Pro Thr Gln Gln Leu Thr Trp Ser Arg Glu Ser Pro Leu Lys
                325                 330                 335

Pro Phe Leu Lys Leu Ser Leu Gly Leu Pro Gly Leu Gly Ile His Met
            340                 345                 350

Arg Pro Leu Ala Ile Trp Leu Phe Ile Phe Asn Val Ser Gln Gln Met
        355                 360                 365

Gly Gly Phe Tyr Leu Cys Gln Pro Gly Pro Pro Ser Glu Lys Ala Trp
    370                 375                 380

Gln Pro Gly Trp Thr Val Asn Val Glu Gly Ser Gly Glu Leu Phe Arg
385                 390                 395                 400

Trp Asn Val Ser Asp Leu Gly Gly Leu Gly Cys Gly Leu Lys Asn Arg
                405                 410                 415

Ser Ser Glu Gly Pro Ser Ser Pro Ser Gly Lys Leu Met Ser Pro Lys
            420                 425                 430

Leu Tyr Val Trp Ala Lys Asp Arg Pro Glu Ile Trp Glu Gly Glu Pro
        435                 440                 445

Pro Cys Val Pro Pro Arg Asp Ser Leu Asn Gln Ser Leu Ser Gln Asp
    450                 455                 460

Leu Thr Met Ala Pro Gly Ser Thr Leu Trp Leu Ser Cys Gly Val Pro
465                 470                 475                 480

Pro Asp Ser Val Ser Arg Gly Pro Leu Ser Trp Thr His Val His Pro
                485                 490                 495

Lys Gly Pro Lys Ser Leu Leu Ser Leu Glu Leu Lys Asp Asp Arg Pro
            500                 505                 510

Ala Arg Asp Met Trp Val Met Glu Thr Gly Leu Leu Leu Pro Arg Ala
        515                 520                 525

Thr Ala Gln Asp Ala Gly Lys Tyr Tyr Cys His Arg Gly Asn Leu Thr
    530                 535                 540
```

```
Met Ser Phe His Leu Glu Ile Thr Ala Arg Pro Val Leu Trp His Trp
545                 550                 555                 560

Leu Leu Arg Thr Gly Gly Trp Lys Val Ser Ala Val Thr Leu Ala Tyr
                565                 570                 575

Leu Ile Phe Cys Leu Cys Ser Leu Val Gly Ile Leu His Leu Gln Arg
            580                 585                 590

Ala Leu Val Leu Arg Arg Lys Arg
        595                 600


<210> SEQ ID NO 61
<211> LENGTH: 36
<212> TYPE: PRT
<213> ORGANISM: Artificial Sequence
<220> FEATURE:
<223> OTHER INFORMATION: Buthus eupeus

<400> SEQUENCE: 61

Met Cys Met Pro Cys Phe Thr Thr Arg Pro Asp Met Ala Gln Gln Cys
1               5                   10                  15

Arg Ala Cys Cys Lys Gly Arg Gly Lys Cys Phe Gly Pro Gln Cys Leu
            20                  25                  30

Cys Gly Tyr Asp
        35


<210> SEQ ID NO 62
<211> LENGTH: 36
<212> TYPE: PRT
<213> ORGANISM: Artificial Sequence
<220> FEATURE:
<223> OTHER INFORMATION: Buthus eupeus

<400> SEQUENCE: 62

Met Cys Met Pro Cys Phe Thr Thr Asp His Gln Thr Ala Arg Arg Cys
1               5                   10                  15

Arg Asp Cys Cys Gly Gly Arg Gly Arg Lys Cys Phe Gly Gln Cys Leu
            20                  25                  30

Cys Gly Tyr Asp
        35


<210> SEQ ID NO 63
<211> LENGTH: 35
<212> TYPE: PRT
<213> ORGANISM: Artificial Sequence
<220> FEATURE:
<223> OTHER INFORMATION: Buthus eupeus

<400> SEQUENCE: 63

Met Cys Met Pro Cys Phe Thr Thr Asp His Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
        35


<210> SEQ ID NO 64
<211> LENGTH: 35
<212> TYPE: PRT
<213> ORGANISM: Artificial Sequence
<220> FEATURE:
<223> OTHER INFORMATION: Buthus eupeus

<400> SEQUENCE: 64
```

-continued

```
Met Cys Met Pro Cys Phe Thr Thr Asp Pro Asn Met Ala Asn Lys Cys
1               5                   10                  15

Arg Asp Cys Cys Gly Gly Gly Lys Lys Cys Phe Gly Pro Gln Cys Leu
            20                  25                  30

Cys Asn Arg
        35


<210> SEQ ID NO 65
<211> LENGTH: 35
<212> TYPE: PRT
<213> ORGANISM: Artificial Sequence
<220> FEATURE:
<223> OTHER INFORMATION: Buthus eupeus

<400> SEQUENCE: 65

Met Cys Met Pro Cys Phe Thr Thr Asp Pro Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
        35


<210> SEQ ID NO 66
<211> LENGTH: 35
<212> TYPE: PRT
<213> ORGANISM: Artificial Sequence
<220> FEATURE:
<223> OTHER INFORMATION: Buthus sindicus

<400> SEQUENCE: 66

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
        35


<210> SEQ ID NO 67
<211> LENGTH: 38
<212> TYPE: PRT
<213> ORGANISM: Artificial Sequence
<220> FEATURE:
<223> OTHER INFORMATION: Leiurus quinquestriatus hebraeus

<400> SEQUENCE: 67

Arg Cys Ser Pro Cys Phe Thr Thr Asp Gln Gln Met Thr Lys Lys Cys
1               5                   10                  15

Tyr Asp Cys Cys Gly Gly Lys Gly Lys Gly Lys Cys Tyr Gly Pro Gln
            20                  25                  30

Cys Ile Cys Ala Pro Tyr
        35


<210> SEQ ID NO 68
<211> LENGTH: 25
<212> TYPE: PRT
<213> ORGANISM: Artificial Sequence
<220> FEATURE:
<223> OTHER INFORMATION: Parabuthus schlechteri
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
```

<222> LOCATION: (23)..(23)
<223> OTHER INFORMATION: Xaa can be any naturally occurring amino acid

<400> SEQUENCE: 68

```
Arg Cys Lys Pro Cys Phe Thr Thr Asp Pro Gln Met Ser Lys Lys Cys
1               5                   10                  15

Ala Asp Xaa Cys Gly Gly Xaa Lys Ser
            20                  25
```

<210> SEQ ID NO 69
<211> LENGTH: 36
<212> TYPE: PRT
<213> ORGANISM: Artificial Sequence
<220> FEATURE:
<223> OTHER INFORMATION: Buthus sindicus

<400> SEQUENCE: 69

```
Cys Gly Pro Cys Phe Thr Lys Asp Pro Glu Thr Glu Lys Lys Cys Ala
1               5                   10                  15

Thr Cys Cys Gly Gly Ile Gly Arg Cys Phe Gly Pro Gln Cys Leu Cys
            20                  25                  30

Asn Arg Gly Tyr
        35
```

<210> SEQ ID NO 70
<211> LENGTH: 35
<212> TYPE: PRT
<213> ORGANISM: Artificial Sequence
<220> FEATURE:
<223> OTHER INFORMATION: Androctonus mauretanicus mauretanicus

<400> SEQUENCE: 70

```
Cys Gly Pro Cys Phe Thr Thr Asp Pro Tyr Thr Glu Ser Lys Cys Ala
1               5                   10                  15

Thr Cys Cys Gly Gly Arg Gly Lys Cys Val Gly Pro Gln Cys Leu Cys
            20                  25                  30

Asn Arg Ile
        35
```

<210> SEQ ID NO 71
<211> LENGTH: 34
<212> TYPE: PRT
<213> ORGANISM: Artificial Sequence
<220> FEATURE:
<223> OTHER INFORMATION: Androctonus australis

<400> SEQUENCE: 71

```
Met Cys Ile Pro Cys Phe Thr Thr Asn Pro Asn Met Ala Ala Lys Cys
1               5                   10                  15

Asn Ala Cys Cys Gly Ser Arg Arg Gly Ser Cys Arg Gly Pro Gln Cys
            20                  25                  30

Ile Cys
```

<210> SEQ ID NO 72
<211> LENGTH: 34
<212> TYPE: PRT
<213> ORGANISM: Artificial Sequence
<220> FEATURE:
<223> OTHER INFORMATION: Leiurus quinquestriastus hebraeus

<400> SEQUENCE: 72

```
Cys Gly Pro Cys Phe Thr Thr Asp His Gln Met Glu Gln Lys Cys Ala
1               5                   10                  15
```

```
Glu Cys Cys Gly Gly Ile Gly Lys Cys Tyr Gly Pro Gln Cys Leu Cys
            20                  25                  30

Asn Arg


<210> SEQ ID NO 73
<211> LENGTH: 35
<212> TYPE: PRT
<213> ORGANISM: Artificial Sequence
<220> FEATURE:
<223> OTHER INFORMATION: Buthus martensii

<400> SEQUENCE: 73

Cys Gly Pro Cys Phe Thr Thr Asp Ala Asn Met Ala Arg Lys Cys Arg
1               5                   10                  15

Glu Cys Cys Gly Gly Ile Gly Lys Cys Phe Gly Pro Gln Cys Leu Cys
            20                  25                  30

Asn Arg Ile
        35


<210> SEQ ID NO 74
<211> LENGTH: 35
<212> TYPE: PRT
<213> ORGANISM: Artificial Sequence
<220> FEATURE:
<223> OTHER INFORMATION: Buthus martensii

<400> SEQUENCE: 74

Cys Gly Pro Cys Phe Thr Thr Asp Ala Asn Met Ala Arg Lys Cys Arg
1               5                   10                  15

Glu Cys Cys Gly Gly Asn Gly Lys Cys Phe Gly Pro Gln Cys Leu Cys
            20                  25                  30

Asn Arg Glu
        35


<210> SEQ ID NO 75
<211> LENGTH: 37
<212> TYPE: PRT
<213> ORGANISM: Artificial Sequence
<220> FEATURE:
<223> OTHER INFORMATION: Buthus tamulus

<400> SEQUENCE: 75

Arg Cys Gly Pro Cys Phe Thr Thr Asp Pro Gln Thr Gln Ala Lys Cys
1               5                   10                  15

Ser Glu Cys Cys Gly Arg Lys Gly Gly Val Cys Lys Gly Pro Gln Cys
            20                  25                  30

Ile Cys Gly Ile Gln
        35


<210> SEQ ID NO 76
<211> LENGTH: 35
<212> TYPE: PRT
<213> ORGANISM: Artificial Sequence
<220> FEATURE:
<223> OTHER INFORMATION: Buthus tamulus

<400> SEQUENCE: 76

Arg Cys Pro Pro Cys Phe Thr Thr Asn Pro Asn Met Glu Ala Asp Cys
1               5                   10                  15

Arg Lys Cys Cys Gly Gly Arg Gly Tyr Cys Ala Ser Tyr Gln Cys Ile
            20                  25                  30
```

-continued

```
Cys Pro Gly
        35


<210> SEQ ID NO 77
<211> LENGTH: 29
<212> TYPE: PRT
<213> ORGANISM: Artificial Sequence
<220> FEATURE:
<223> OTHER INFORMATION: Leiurus quinquestriatus hebraeus

<400> SEQUENCE: 77

Val Ser Cys Glu Asp Cys Pro Asp His Cys Ser Thr Gln Lys Ala Arg
1               5                   10                  15

Ala Lys Cys Asp Asn Asp Lys Cys Val Cys Glu Pro Ile
            20                  25
```

CHIMERIC ANTIGEN RECEPTORS CONTAINING A CHLOROTOXIN DOMAIN

CROSS-REFERENCE TO RELATED APPLICATIONS

This application is a National Stage Application under 35 U.S.C. §371 and claims the benefit of International Application No. PCT/US2016/056901, filed Oct. 13, 2016, which claims the benefit of U.S. Provisional Application No. 62/241,021, filed Oct. 13, 2015. The disclosure of the foregoing applications are hereby incorporated by reference in their entirety.

SEQUENCE LISTING

The present application contains a Sequence Listing, which has been submitted electronically in ASCII format and is hereby incorporated by reference in its entirety. Said ASCII copy, created on Oct. 19, 2020, is named Sequence-Listing.txt and is 115,000 bytes in size, the entire contents of which are hereby incorporated by reference.

BACKGROUND

Tumor-specific T cell based immunotherapies, including therapies employing engineered T cells, have been investigated for anti-tumor treatment. Chimeric antigen receptors (CARs) are composed of an extracellular tumor recognition/targeting domain, an extracellular linker/spacer, a transmembrane domain, and intracellular T cell-activating and co-stimulatory signaling domains. The design of the recognition/targeting domain is critical to avoiding deleterious off-target effects. The majority of CAR tumor targeting domains are single chain variable fragments (scFvs) derived from antibody sequences that exploit the specificity of antibody binding to particular antigens. There are also examples of CAR tumor targeting domains derived from normal receptor ligands, such as the IL-13 cytokine CAR that targets cells expressing the IL-13 receptor, IL13Rα2. Despite some notable successes, the identification and validation of novel CAR tumor targeting domains remains a major challenge in the field.

Malignant gliomas (MG), which include anaplastic astrocytoma (AA-WHO grade III) and glioblastoma (GBM-WHO grade IV), have an incidence rate of approximately 20,000 new cases diagnosed annually in the United States. According to the American Brain Tumor Association total prevalence of individuals living with a malignant brain tumor, based on United States 2010 census data, is roughly 140,000 persons. Although MG is a rare disease, it is highly aggressive and heterogeneous with respect to its malignant behavior and nearly uniformly lethal. Current standard-of-care therapies for high-grade MG yield only short term benefits, and these brain tumors are virtually incurable. Indeed, even with modern surgical and radiotherapeutic techniques, which often exacerbate the already severe morbidities imposed by location in the central nervous system (CNS), the 5-year survival rates are quite low. Furthermore, for the majority of patients who relapse with disease, there are few therapeutic options. Thus, there is a significant need for more effective therapies, particularly for those patients that have recurred/progressed following frontline therapies.

Adoptive T cell therapy (ACT) utilizing engineered T cells expressing a CAR may provide a safe and effective way to reduce recurrence rates of MG, since CAR T cells can be engineered to specifically recognize antigenically-distinct tumor populations (Cartellieri et al. 2010 *J Biomed Biotechnol* 2010:956304; Ahmed et al. 2010 *Clin Cancer Res* 16:474; Sampson et al. 2014 *Clin Cancer Res* 20:972; Brown et al. 2013 *Clin Cancer Res* 2012 18:2199; Chow et al. 2013 *Mol Ther* 21:629), and T cells can migrate through the brain parenchyma to target and kill infiltrative malignant cells (Hong et al. 2010 *Clin Cancer Res* 16:4892; Brown et al. 2007 *J Immunol* 179:3332; Hong et al. 2010 *Clin Cancer Res* 16:4892; Yaghoubi 2009 *Nat Clin Pract Oncol* 6:53).

SUMMARY

Described herein are chimeric transmembrane immunoreceptors (chimeric antigen receptors or "CARs") which comprise an extracellular domain, a transmembrane region and an intracellular signaling domain. The extracellular domain includes chlorotoxin (a 36 amino acid peptide toxin found in venom from the scorpion *Leiurus quinquestriatus*), or a related toxin, or a variant of chlorotoxin or a related toxin, and, optionally, a spacer, comprising, for example, a portion of human Fc domain. The transmembrane portion includes, for example, a CD4 transmembrane domain, a CD8 transmembrane domain, a CD28 transmembrane domain, or a CD3 transmembrane domain. The intracellular signaling domain includes the signaling domain from the zeta chain of the human CD3ζ complex (CD3) and one or more costimulatory domains, for example, a 4-1BB costimulatory domain. The extracellular domain enables the CAR, when expressed on the surface of a T cell, to direct T cell activity to those cells expressing a receptor for chlorotoxin. Such cells include glioblastoma cells. The inclusion of a costimulatory domain, such as the 4-1BB (CD137) costimulatory domain in series with CD3ζ in the intracellular region enables the T cell to receive co-stimulatory signals. T cells, for example, patient-specific, autologous T cells can be engineered to express the CARs described herein, and the engineered cells can be expanded and used in ACT. Various T cell subsets, including both alpha beta T cells and gamma delta T cells, can be used. In addition, the CAR can be expressed in other immune cells such as NK cells. Where a patient is treated with an immune cell expressing a CAR described herein the cell can be an autologous T cell or an allogenic T cell. In some cases, the cells used are a cell population that includes both CD4+ and CD8+ central memory T cells ($T_{CM}$), which are CD62L+, CCR7+, CD45RO+, and CD45RA−, or the cells used are a cell population that includes CD4+ and CD8+ $T_{CM}$ cells, stem central memory T cells and naïve T cells (i.e., a population of $T_{CM/SCM/N}$ cells). A population of $T_{CM/SCM/N}$ cells are CD62L+, CCR7+ and include both CD45RA+ and CD45RO+ cells as well as both CD4+ cells and CD8+ cells. The use of such cells can improve long-term persistence of the cells after adoptive transfer compared to the use of other types of patient-specific T cells.

Described herein is a nucleic acid molecule encoding a CAR comprising: chlorotoxin (MCMPCFTTDHQ-MAKRCDDCCGGKGRGKCYGPQCLCR; SEQ ID NO:1) or a variant thereof having 1-5 (e.g., 1 or 2) amino acid modifications (e.g., substitutions) provided that the cysteine residues are not modified; a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ζ transmembrane domain or a variant thereof having 1-5 (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and a CD3ζ signaling domain or a variant thereof having 1-5 (e.g., 1 or 2) amino acid modifications.

In some embodiments the CAR includes a toxin related to chlorotoxin instead of chlorotoxin. Thus, the CAR can include GaTx2, a toxin from *Leiurus quinquestriatus hebraeus* (VSCEDCPDHCSTQKARAKCDNDKCVCEPI; SEQ ID NO:56) or a variant thereof having 1-5 (e.g., 1 or 2) amino acid modifications (e.g., substitutions) provided that the cysteine residues are not modified; a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ζ transmembrane domain or a variant thereof having 1-5 (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ζ signaling domain or a variant thereof having 1-5 (e.g., 1 or 2) amino acid modifications (e.g., substitutions).

In some cases, the CAR can include more than one chlorotoxin sequence (e.g., two or three or more copies of SEQ ID NO: 1 either consecutively or separated by 1-10 amino acids) or more than one toxins related to chlorotoxin. Thus, the CAR can include two or chlorotoxin sequences (e.g., SEQ ID NO: 1 followed by SEQ ID NO: 1 followed by the rest of the molecule) or the CAR can include a chlorotoxin sequence followed by the sequence of a toxin related to chlorotoxin (e.g., SEQ ID NO:57 or another toxin depicted in FIG. 25.

The CAR can include GaTx1, a toxin from *Leiurus quinquestriatus hebraeus* (CGPCFTTDHQMEQKCAECCGGIGKCYGPQCLCNR; SEQ ID NO:57) or a variant thereof having 1-5 (e.g., 1 or 2) amino acid modifications (e.g., substitutions) provided that the cysteine residues are not modified; a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ζ transmembrane domain or a variant thereof having 1-5 (e.g., 1 or 2) amino acid modifications; a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ζ signaling domain or a variant thereof having 1-5 (e.g., 1 or 2) amino acid modifications (e.g., substitutions).

The CAR can include AaCtx, a toxin from *Androctonus australis* (MCIPCFTTNPNMAAKCNACCGSRRGSCRGPQCIC; SEQ ID NO:58) or a variant thereof having 1-5 (e.g., 1 or 2) amino acid modifications (e.g., substitutions) provided that the cysteine residues are not modified; a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ζ transmembrane domain or a variant thereof having 1-5 (e.g., 1 or 2) amino acid modifications; a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ζ signaling domain or a variant thereof having 1-5 (e.g., 1 or 2) amino acid modifications (e.g., substitutions).

The CAR can include BmKCT, a toxin from *Buthus martensii* (CGPCFTTDANMARKCRECCGGIGKCFGPQCLCNRI; SEQ ID NO:59) or a variant thereof having 1-5 (e.g., 1 or 2) amino acid modifications (e.g., substitutions) provided that the cysteine residues are not modified; a transmembrane domain selected from: a transmembrane domain depicted in Table 2 or a variant thereof having 1-5 (e.g., 1 or 2) amino acid modifications a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ζ transmembrane domain or a variant thereof having 1-10 (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ζ signaling domain or a variant thereof having 1-5 (e.g., 1 or 2) amino acid modifications (e.g., substitutions).

In various embodiments, the CAR comprises the amino acid sequence of any of SEQ ID NOs:26-55 wherein the chlorotoxin sequence (SEQ ID NO: 1) is replaced by an amino acid sequence selected from SEQ ID NOs: 56-59 or a variant thereof having 1-5 (e.g., 1 or 2) amino acid modifications (e.g., substitutions).

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions.

In some cases, there is a short sequence of 1-6 amino acids (e.g. GGG) between the co-stimulatory domains and the CD3ζ signaling domain and/or between the two co-stimulatory domains.

Additional embodiment the CAR comprises: a variant of a chlorotoxin having 1-5 amino acid modifications that increase binding specificity or immunogenicity for the chlorotoxin receptor (Cltx-R); the chlorotoxin variant is a variant comprising the amino acid sequence of SEQ ID NO: 1 with 1-5 (e.g., 1 or 2) amino acid modifications; two different costimulatory domains selected from the group consisting of: a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications; two different costimulatory domains selected from the group consisting of: a CD28 costimulatory domain or a variant thereof having 1-2 amino acid modifications, a 4-1BB costimulatory domain or a variant thereof having 1-2 amino acid modifications and an OX40 costimulatory domain or a variant thereof having 1-2 amino acid modifications; chlorotoxin or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3ζ transmembrane domain or a variant thereof having 1-2 amino acid modifications; a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ζ signaling domain of a variant thereof having 1-2 amino acid modifications; a spacer region located between the chlorotoxin or variant thereof and the transmembrane domain (e.g., the spacer region comprises an amino acid sequence selected from the group consisting of SEQ ID NOs: 2-12 (Table 3) or a variant thereof having 1-5 (e.g., 1 or 2) amino acid modifications); the spacer comprises an IgG hinge region; the spacer region comprises 1-150 amino acids; there is no spacer; the 4-1BB signaling domain comprises the amino acid sequence of SEQ ID NO:24 the CD3ζ signaling domain comprises the amino acid sequence of SEQ ID NO:21 and a linker of 3 to 15 amino acids that is located between the costimulatory domain and the CD3ζ signaling domain or variant thereof. In certain embodiments where there are two costimulatory domains, one is a 4-1BB costimulatory domain and the other a costimulatory domain selected from: CD28 and CD28gg. In various embodiments the 1-5 (e.g., 1 or 2) amino acid modification are substitutions.

In some embodiments: nucleic acid molecule expresses a polypeptide comprising an amino acid sequence selected from SEQ ID NOs: 26-55; the chimeric antigen receptor comprises an amino acid sequence selected from SEQ ID NOs: 26-55.

Also disclosed is a population of human T cells transduced by a vector comprising an expression cassette encoding a chimeric antigen receptor, wherein chimeric antigen receptor comprises: either chlorotoxin or a variant thereof having 1-5 amino acid modifications (e.g., 1 or 2) amino acid modifications (e.g., substitutions) or a toxin related to chlorotoxin or a variant thereof having 1-5 amino acid modifications (e.g., 1 or 2) amino acid modifications (e.g., substitutions); a transmembrane domain selected from: a CD4 transmembrane domain or variant thereof having 1-5 amino acid modifications (e.g., 1 or 2) amino acid modifications (e.g., substitutions), a CD8 transmembrane domain or variant thereof having 1-5 amino acid modifications (e.g., 1 or 2) amino acid modifications (e.g., substitutions), a CD28 transmembrane domain or a variant thereof having 1-5 amino acid modifications (e.g., 1 or 2) amino acid modifications (e.g., substitutions), and a CD3ζ transmembrane domain or a variant thereof having 1-5 amino acid modifications (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ζ signaling domain of a variant thereof having 1-5 amino acid modifications (e.g., 1 or 2) amino acid modifications (e.g., substitutions). In various embodiments: the population of human T cells comprise a vector expressing a chimeric antigen receptor comprising an amino acid sequence selected from SEQ ID NOs: 26-55 or a variant thereof having 1-5 amino acid modifications (e.g., 1 or 2) amino acid modifications (e.g., substitutions); the population of human T cells comprises central memory T cells ($T_{CM}$ cells) e.g., at least 20%, 30%, 40%, 50% 60%, 70%, 80% of the cells are $T_{CM}$ cells, or the population of T cells comprises a combination of central memory T cells, naïve T cells and stem central memory cells ($T_{M/SCM/N}$ cells) e.g., at least 20%, 30%, 40%, 50% 60%, 70%, 80% of the cells are $T_{CM/SCM/N}$ cells. In either case, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells).

Also described is a method of treating cancer in a patient comprising administering a population of autologous or allogeneic human T cells (e.g., autologous or allogenic T cells comprising central memory T cells ($T_{CM}$ cells) or a combination of central memory T cells, naïve T cells and stem central memory cells (i.e., the T cells are $T_{CM/SCM/N}$ cells) at least 20%, 30%, 40%, 50% 60%, 70%, 80% of the cells are $T_{CM/SCM/N}$ cells. In either case, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells) transduced by a vector comprising an expression cassette encoding a chimeric antigen receptor, wherein chimeric antigen receptor comprises an amino acid sequence selected from SEQ ID NOs: 26-55 or a variant thereof having 1-5 (e.g., 1 or 2) amino acid modifications (e.g., substitutions). In various embodiments: the cancer is glioblastoma; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 26-55 or a variant thereof having 1-5 (e.g., 1 or 2) amino acid modifications (e.g., substitutions).

Also described is: a nucleic acid molecule encoding an polypeptide comprising an amino acid sequence that is at least 95% identical to an amino acid sequence selected from SEQ ID NOs 26-55; a nucleic acid molecule encoding an polypeptide comprising an amino acid sequence that is identical to an amino acid sequence selected from SEQ ID NOs: 26-55 except for the presence of no more than 5 amino acid substitutions, deletions or insertions; a nucleic acid molecule encoding an polypeptide comprising an amino acid sequence that is identical to an amino acid sequence selected from SEQ ID NOs:26-55 except for the presence of no more than 5 amino acid substitutions; and a nucleic acid molecule encoding an polypeptide comprising an amino acid sequence that is identical to an amino acid sequence selected from SEQ ID NOs:26-55 except for the presence of no more than 2 amino acid substitutions.

T cells expressing a CAR comprising chlorotoxin or a variant thereof can be useful in treatment of cancers such as glioblastoma, as well as other cancers expressing a receptor for chlorotoxin, which include, but are not limited to: primary brain tumors and gliomas (glioblastoma multiforme WHO Grade IV, anaplastic astrocytoma WHO Grade III, low-grade astrocytoma WHO Grade II, pilocytic astrocytoma WHO Grade I, other ungraded gliomas, oligodendroglioma, gliosarcoma, ganglioglioma, meningioma, ependymona), neuroectodermal tumors (medulloblastoma, neuroblastoma, ganglioneuroma, melanoma (metastatic), melanoma (primary), pheochromocytoma, Ewing's sarcoma, primitive neuroectodermal tumors, small cell lung carcinoma, Schwannoma), other brain tumors (epidermoid cysts, brain tumors of unknown pathology, pituitary gland of glioblastoma multiforme pt., metastatic tumors to brain of unknown tissue origin), and other tumors (breast cancer, breast cancer metastases, kidney cancer, liver cancer lung cancer, lymphoma, ovarian cancer, pancreatic cancer, prostate cancer).

This disclosure also includes nucleic acid molecules that encode any of the CARs described herein (e.g., vectors that include a nucleic acid sequence encoding one of the CARs) and isolated T lymphocytes that express any of the CARs described herein.

The CAR described herein can include a spacer region located between the chlorotoxin domain (i.e., the chlorotoxin or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48aa | 48 aa | AKPTTTPAPRPPTPAPTIASQPLSLRPE ACRPAAGGAVHTRGLDFACD (SEQ ID NO: 7) |
| CD8 hinge-45aa | 45 aa | TTTPAPRPPTPAPTIASQPLSLRPEACR PAAGGAVHTRGLDFACD (SEQ ID NO: 8) |
| IgG4(HL-CH3) (includes S228P in hinge) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFLYSRLTVDKSRWQEGNV FSCSVMHEALHNHYTQKSLSLSLGK (SEQ ID NO: 9) |
| IgG4(L235E, N297Q) | 229 aa | ESKYGPPCPSCPAPEFEGGPSVFLFPPK PKDTLMISRTPEVTCVVVDVSQEDPE VQFNWYVDGVEVHQAKTKPREEQFQ STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 10) |
| IgG4(S228P, L235E, N297Q) | 229 aa | ESKYGPPCPPCPAPEFEGGPSVFLFPPK PKDTLMISRTPEVTCVVVDVSQEDPE VQFNWYVDGVEVHQAKTKPREEQFQ STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 11) |

TABLE 1-continued

| Examples of Spacers | | |
|---|---|---|
| Name | Length | Sequence |
| IgG4(CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLS LGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In certain embodiments, the spacer is derived from an IgG1, IgG2, IgG3, or IgG4 that includes one or more amino acid residues substituted with an amino acid residue different from that present in an unmodified spacer. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof. In this numbering scheme, described in greater detail below, the first amino acid in the IgG4(L235E, N297Q) spacer in Table 1 is 219 and the first amino acid in the IgG4(HL-CH3) spacer in Table 1 is 219 as is the first amino acid in the IgG hinge sequence and the IgG4 hinge linker (HL) sequence in Table 1

In some embodiments, the modified spacer is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof.

In certain embodiments, the modified spacer is derived from IgG4 region that includes one or more amino acid residues substituted with an amino acid residue different from that present in an unmodified region. The one or more substituted amino acid residues are selected from, but not limited to, one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified spacer is derived from an IgG4 region that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified spacer is substituted with the above identified amino acids at the indicated position.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 *Proc Natl Acad Sci USA* 63:78-85).

A variety of transmembrane domains can be used in the. Table 2 includes examples of suitable transmembrane domains. Where a spacer domain is present, the transmembrane domain is located carboxy terminal to the spacer domain.

TABLE 2

| Examples of Transmembrane Domains | | | |
|---|---|---|---|
| Name | Accession | Length | Sequence |
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAFIIFWV (SEQ ID NO: 14) |
| CD28 (M) | NM_006139 | 28 aa | MFWVLVVVGGVLACYSLLVTVAFIIFWV (SEQ ID NO: 15) |
| CD4 | M35160 | 22 aa | MALIVLGGVAGLLLFIGLGIFF (SEQ ID NO: 16) |
| CD8tm | NM_001768 | 21 aa | IYIWAPLAGTCGVLLLSLVIT (SEQ ID NO: 17) |
| CD8tm2 | NM_001768 | 23 aa | IYIWAPLAGTCGVLLLSLVITLY (SEQ ID NO: 18) |

TABLE 2-continued

| Examples of Transmembrane Domains | | | |
|---|---|---|---|
| Name | Accession | Length | Sequence |
| CD8tm3 | NM_001768 | 24 aa | IYIWAPLAGTCGVLLLSLVITLYC (SEQ ID NO: 19) |
| 41BB | NM_001561 | 27 aa | IISFFLALTSTALLFLLFF LTLRFSVV (SEQ ID NO: 20) |

Many of the CAR described herein include one or more (e.g., two) costimulatory domains. The costimulatory domain(s) are located between the transmembrane domain and the CD3ζ signaling domain. Table 3 includes examples of suitable costimulatory domains together with the sequence of the CD3ζ signaling domain.

TABLE 3

| CD3ζ Domain and Examples of Costimulatory Domains | | | |
|---|---|---|---|
| Name | Accession | Length | Sequence |
| CD3ζ | J04132.1 | 113 aa | RVKFSRSADAPAYQQGQNQLYNE LNLGRREEYDVLDKRRGRDPEMG GKPRRKNPQEGLYNELQKDKMAE |

TABLE 3-continued

| CD3ζ Domain and Examples of Costimulatory Domains | | | |
|---|---|---|---|
| Name | Accession | Length | Sequence |
| | | | AYSEIGMKGERRRGKGHDGLYQG LSTATKDTYDALHMQALPPR (SEQ ID NO: 21) |
| CD28 | NM_006139 | 42 aa | RSKRSRLLHSDYMNMTPRRPGPT RKHYQPYAPPRDFAAYRS (SEQ ID NO: 22) |
| CD28gg* | NM_006139 | 42 aa | RSKRSRGGHSDYMNMTPRRPGPT RKHYQPYAPPRDFAAYRS (SEQ ID NO: 23) |
| 41BB | NM_001561 | 42 aa | KRGRKKLLYIFKQPFMRPVQTTQ EEDGCSCRFPEEEEGGCEL (SEQ ID NO: 24) |
| OX40 | | 42 aa | ALYLLRRDQRLPPDAHKPPGGGS FRTPIQEEQADAHSTLAKI (SEQ ID NO: 25) |

Among the CAR comprising chlorotoxin described herein are those summarized in Table 4 in which the spacer domain, transmembrane domain and costimulatory domain(s) for each CAR are indicated.

TABLE 4

| Examples of CAR Comprising Chlorotoxin | | | | | |
|---|---|---|---|---|---|
| Name | SEQ ID NO* | FIGURE | Spacer | IM | Costimulatory Domain(s) |
| CLTX-IgG4(EQ)-CD28tm-CD28-zeta | 26/41 | 7 | IgG4(EQ) | CD28 | CD28 |
| CLTX-IgG4(HL-CH3)-CD28tm-CD28-zeta | 27/42 | 8 | IgG4(HL-CH3) | CD28 | CD28 |
| CLTX-CD8h- CD28tm-CD28-zeta | 28/43 | 9 | CD8h | CD28 | CD28 |
| CLTX-IgG4(hinge)-CD28tm-CD28-zeta | 29/44 | 10 | IgG4(hinge) | CD28 | CD28 |
| CLTX-L-CD28tm-CD28-zeta | 30/45 | 11 | L | CD28 | CD28 |
| CLTX-IgG4(EQ)-CD28tm-CD28-4-1BB-zeta | 31/46 | 12 | IgG4(EQ) | CD28 | CD28-4-1BB |
| CLTX-IgG4(HL-CH3)-CD28tm-CD28-4-1BB-zeta | 32/47 | 13 | IgG4(HL-CH3) | CD28 | CD28-4-1BB |
| CLTX-CD8h-CD28tm-CD28-4-1BB-zeta | 33/48 | 14 | CD8h | CD28 | CD28-4-1BB |
| CLTX-IgG4(hinge)-CD28tm-CD28-4-1BB-zeta | 34/49 | 15 | IgG4(hinge) | CD28 | CD28-4-1BB |
| CLTX-L-CD28tm-CD28-4-1BB-zeta | 35/50 | 16 | L | CD28 | CD28-4-1BB |
| CLTX-IgG4(EQ)-CD4tm-4-1BB-zeta | 36/51 | 17 | IgG4(EQ) | CD4 | 4-1BB |
| CLTX-IgG4(HL-CH3)-CD4tm-4-1BB-zeta | 37/52 | 18 | IgG4(HL-CH3) | CD4 | 4-1BB |
| CLTX-CD8h- CD28tm-4-1BB-zeta | 38/53 | 19 | CD8h | CD28 | 4-1BB |
| CLTX-IgG4(hinge)-CD28tm-4-1BB-zeta | 39/54 | 20 | IgG4(hinge) | CD28 | 4-1BB |
| CLTX-L-CD28tm-4-1BB-zeta | 40/55 | 21 | L | CD28 | 4-1BB |

*SEQ ID NOs for sequence including signal sequence/SEQ ID NOs for sequence excluding signal sequence.

DESCRIPTION OF DRAWINGS

FIG. 9 depicts the amino acid sequence of CLTX-IgG4 (L235E N297Q)-CD28tm-CD28gg-zeta (SEQ ID NO:26).

FIG. 10 depicts the amino acid sequence of CLTX-IgG4 (HL-CH3)-CD28tm-CD28gg-zeta (SEQ ID NO:27).

FIG. 11 depicts the amino acid sequence of CLTX-CD8h-CD28tm-CD28gg-zeta (SEQ ID NO:28).

FIG. 12 depicts the amino acid sequence of CLTX-IgG4 (hinge)-CD28tm-CD28gg-zeta (SEQ ID NO:29).

FIG. 13 depicts the amino acid sequence of CLTX-L-CD28tm-CD28gg-zeta (SEQ ID NO:30).

FIG. 14 depicts the amino acid sequence of CLTX-IgG4 (L235E N297Q)-CD28tm-CD28gg-4-1BB-zeta (SEQ ID NO:31).

FIG. 15 depicts the amino acid sequence of CLTX-IgG4 (HL-CH3)-CD28tm-CD28gg-4-1BB-zeta (SEQ ID NO:32).

FIG. 16 depicts the amino acid sequence of CLTX-CD8h-CD28tm-CD28gg-4-1BB-zeta (SEQ ID NO:33).

FIG. 17 depicts the amino acid sequence of CLTX-IgG4 (hinge)-CD28tm-CD28gg-4-1BB-zeta (SEQ ID NO:34).

FIG. 18 depicts the amino acid sequence of CLTX-L-CD28tm-CD28gg-4-1BB-zeta (SEQ ID NO:35).

FIG. 19 depicts the amino acid sequence of CLTX-IgG4 (L235E N297Q)-CD4tm-CD28tm-4-1BB-zeta (SEQ ID NO:36).

FIG. 20 depicts the amino acid sequence of CLTX-IgG4 (HL-CH3)-CD4tm-4-1BB-zeta (SEQ ID NO:37).

FIG. 21 depicts the amino acid sequence of CLTX-CD8h-CD28tm-4-1BB-zeta (SEQ ID NO:38).

FIG. 22 depicts the amino acid sequence of CLTX-IgG4 (hinge)-CD28tm-4-1BB-zeta (SEQ ID NO:39).

FIG. 23 depicts the amino acid sequence of CLTX-L-CD28tm-4-1BB-zeta (SEQ ID NO:40).

FIG. 24 depicts the CAR of FIG. 21 with a T2A (ribosomal skip sequence and a truncated CD19, SEQ ID NO:60). The truncated CD19 is co-expressed with CAR, permitting a simple way in which to identify and quantify transfected cells.

FIG. 25 depicts various chlorotoxin-related toxins (SEQ ID Nos:1, 61-70, 58, 57, 59, 71-73, and 56) and an alignment of their amino acid sequences (Dardevet et al. 2015 *Toxins* (Basel) 7:1079).

DETAILED DESCRIPTION

Figure 1:
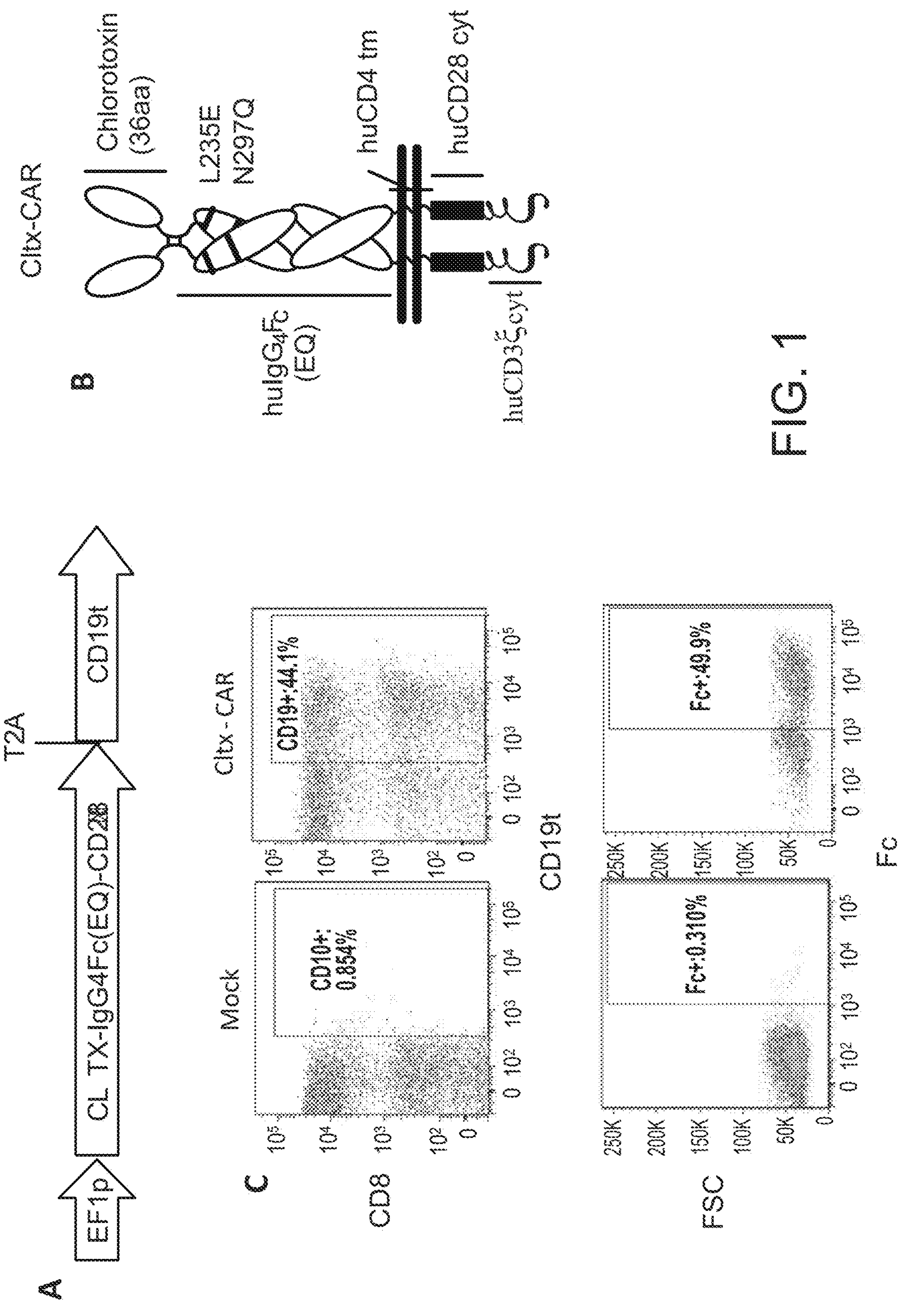
FIG. 1A-C: Generation of CLTX-CAR expressing T cells. (A) Schematic of the lentiviral construct encoding the chlorotoxin (CLTX)-redirected chimeric antigen receptor (CAR) cassette, where transcription of the CLTX-CAR, as well as the T2A ribosomal skip and truncated CD19 (CD19t) sequences are driven by the EF1 promoter (EF1p). (B) Diagram of the CLTX-CAR, which contains the extracellular 36-amino acid chlorotoxin peptide and IgG4Fc (EQ) spacer domains, the CD28 transmembrane domain, and the intracellular CD28 and CD3ζ cytoplasmic signaling domain sequences. (C) Flow cytometric analysis of healthy donor T cells (HD187.2 $T_{CM/SCM/N}$) engineered to express the CLTX-CAR. Shown is anti-CD19 anti-Fc and anti-CD8 staining, representing co-expression of the CLTX-CAR and CD19t transgenes in both $CD8^+$ and $CD4^+$ ($CD8^-$) T cell subsets. Percentages of immunoreactive cells for transduced cells (CLTX-CAR) and untransduced cells (Mock) 18 days after CD3/CD28 bead stimulation are shown to demonstrate the capability to transduce human T cells with CLTX-CAR.

Described below is the structure, construction and characterization of various chimeric antigen receptors comprising chlorotoxin (CLTX). A chimeric antigen receptor (CAR) is a recombinant biomolecule that contains, at a minimum, an extracellular recognition domain, a transmembrane region, and an intracellular signaling domain. The term "antigen," therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more costimulatory signaling domains. CARs can both bind to antigen and induce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

One CAR comprising chlorotoxin described herein is referred to as CLTX-IgG4(EQ)-CD28gg-Zeta. This CAR includes a variety of important features including: chlorotoxin; an IgG4 Fc region that is mutated at two sites within the CH2 region (L235E; N297Q) in a manner that reduces binding by Fc receptors (FcRs); domain, a CD28 co-stimulatory domain, and CD3ζ activation domain.

In some cases the CAR described herein can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD19t provides a marker for immunological targeting of the transduced cells in vivo using clinically available antibodies and/or immunotoxin reagents to selectively delete the therapeutic cells, and thereby functioning as a suicide switch.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets or $T_{CM}$ or $T_{CM/SCM/N}$ can be transduced with a vector for CAR expression. Central memory T cells are one useful T cell subset. Central memory T cell can be isolated from peripheral blood mononuclear cells (PBMC) by enriching for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a SIN lentiviral vector that directs the expression of the CAR as well as a truncated human CD19 (CD19t), a non-immunogenic surface marker for both in vivo detection and potential ex vivo selection. The activated/genetically modified central memory T cells can be expanded in vitro with IL-2/IL-15 and then cryopreserved.

Example 1: Construction and Structure of CLTX-IgG4Fc(EQ)-CD28-zeta CAR

The structure of a useful CAR comprising chlorotoxin, CLTX-IgG4Fc(EQ)-CD28-zeta, is described below. The codon optimized CAR sequence includes: chlorotoxin, an IgG4 Fc spacer containing mutations (S228P, L235E) that greatly reduce Fc receptor-mediated recognition, a CD28 transmembrane domain, a costimulatory CD28 cytoplasmic signaling domain, and a CD3ζ cytoplasmic signaling domain. A T2A ribosome skip sequence separates this CAR sequence from CD19t, an inert, non-immunogenic cell surface detection/selection marker. This T2A linkage results in the coordinate expression of both the CAR and CD19t from a single transcript. FIG. 1A is a schematic drawing of the open reading frame of CLRX-IgG4Fc(EQ)-CD28-zeta-T2ACD19t. In this drawing, the CLTX-IgG4Fc(EQ)-CD28-zeta CAR, as well as the T2A ribosome skip and truncated CD19 sequences are all indicated. The expression of the CAR and CD19t cassette is driven by the human EF1 promoter (EF1p). FIG. 1B schematically depicts the expressed, mature CAR.

The CLTX-IgG4Fc(EQ)-CD28-zeta sequence was generated by fusion of the human GM-CSF receptor alpha leader peptide chlorotoxin, S228P/L235E/N297Q-modified IgG4 Fc hinge (where the double mutation L235E/N297Q interferes with FcR recognition), CD28 transmembrane, CD28 cytoplasmic signaling domain, and CD3ζ cytoplasmic signaling domain sequences. This sequence was synthesized de novo after codon optimization. The T2A sequence was obtained from digestion of a T2A-containing plasmid. The CD19t sequence was obtained from that spanning the leader peptide sequence to the transmembrane components (i.e., basepairs 1-972) of a CD19-containing plasmid. All three fragments, 1) CLTX-IgG4Fc(EQ)-CD28-zeta, 2) T2A, and 3) CD19t, were cloned into the multiple cloning site of the epHIV7 lentiviral vector. When transfected into appropriate cells, the vector integrates into the host cells genome. The amino acid sequence of CLTX-IgG4Fc(EQ)-CD28-zeta is presented in FIG. 9 with the various domains indicated.

Example 2: Construction and Structure of epHIV7 Used for Expression of CLTX-IgG4Fc(EQ)-CD28-zeta The pHIV7 plasmid is the parent plasmid from which the clinical vector CLTX-IgG4Fc(EQ)-CD28-zeta-T2A-CD19t epHIV7 was derived in the T cell Therapeutics Research Laboratory (TCTRL) at City of Hope (COH). The epHIV7 vector used for expression of the CAR was produced from pHIV7 vector. Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository. The woodchuck post-transcriptional regulatory element (WPRE) sequence was previously described.

Construction of pHIV7 was carried out as follows. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi (ψ), is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector), are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EF1α-HTLV promoter (EF1p), and the new plasmid was named epHIV7. The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the CLTX-IgG4Fc(EQ)-CD28-zeta-T2ACD19t epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes.

Example 3: Production of Vectors for Transduction of Patient T Cells

Vectors for transduction of patient T cells can be prepared as follows. For each plasmid (i.e., 1) the plasmid expressing the CAR and, optionally, a marker such as truncated CD19; 2) pCgp; 3) pCMV-G; and 4) pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells are expanded from the 293T working cell (WCB), which has been tested to confirm sterility and the absence of viral contamination. A vial of 293T cells from the 293T WCB is thawed. Cells are grown and expanded until sufficient numbers of cells exists to plate an appropriate number of 10 layer cell factories (CFs) for vector production and cell train maintenance. A single train of cells can be used for production.

The lentiviral vector is produced in sub-batches of up to 10 CFs. Two sub-batches can be produced in the same week leading to the production of approximately 20 L of lentiviral supernatant/week. The material produced from all sub-batches is pooled during the downstream processing phase, in order to produce one lot of product. 293T cells are plated in CFs in 293T medium (DMEM with 10% FBS). Factories are placed in a 37° C. incubator and horizontally leveled in order to get an even distribution of the cells on all the layers of the CF. Two days later, cells are transfected with the four lentiviral plasmids described above using the $CaPO_4$ method, which involves a mixture of Tris:EDTA, 2M $CaCl_2$, 2×HBS, and the four DNA plasmids. Day 3 after transfection, the supernatant containing secreted lentiviral vectors is collected, purified and concentrated. After the supernatant is removed from the CFs, End-of-Production Cells are collected from each CF. Cells are trypsinized from each factory and collected by centrifugation. Cells are resuspended in freezing medium and cryopreserved. These cells are later used for replication-competent lentivirus (RCL) testing.

To purify and formulate vectors crude, supernatant is clarified by membrane filtration to remove the cell debris. The host cell DNA and residual plasmid DNA are degraded by endonuclease digestion (Benzonase®). The viral supernatant is clarified of cellular debris using a 0.45 m filter. The clarified supernatant is collected into a pre-weighed container into which the Benzonase® is added (final concentration 50 U/mL).

The endonuclease digestion for residual plasmid DNA and host genomic DNA is performed at 37° C. for 6 h. The initial tangential flow ultrafiltration (TFF) concentration of the endonuclease-treated supernatant is used to remove residual low molecular weight components from the crude supernatant, while concentrating the virus ~20 fold. The clarified endonuclease-treated viral supernatant is circulated through a hollow fiber cartridge with a NMWCO of 500 kD at a flow rate designed to maintain the shear rate at ~4,000 $sec^{-1}$ or less, while maximizing the flux rate. Diafiltration of the nuclease-treated supernatant is initiated during the concentration process to sustain the cartridge performance. An 80% permeate replacement rate is established, using 4% lactose in PBS as the diafiltration buffer. The viral supernatant is brought to the target volume, representing a 20-fold concentration of the crude supernatant, and the diafiltration is continued for 4 additional exchange volumes, with the permeate replacement rate at 100%.

Further concentration of the viral product is accomplished by using a high speed centrifugation technique. Each sub-batch of the lentivirus is pelleted using a Sorvall RC-26 plus centrifuge at 6000 RPM (6,088 RCF) at 6° C. for 16-20 h. The viral pellet from each sub-batch is then reconstituted in a 50 mL volume with 4% lactose in PBS. The reconstituted pellet in this buffer represents the final formulation for the virus preparation. The entire vector concentration process results in a 200-fold volume reduction, approximately. Following the completion of all of the sub-batches, the material is then placed at −80° C., while samples from each sub-batch are tested for sterility. Following confirmation of sample sterility, the sub-batches are rapidly thawed at 37° C. with frequent agitation. The material is then pooled and manually aliquoted in the Class II Type A/B3 biosafety cabinet. A fill configuration of 1 mL of the concentrated lentivirus in sterile USP class 6, externally threaded O-ring cryovials is used.

To ensure the purity of the lentiviral vector preparation, it is tested for residual host DNA contaminants, and the transfer of residual host and plasmid DNA. Among other tests, vector identity is evaluated by RT-PCR to ensure that the correct vector is present.

Example 4: Preparation of T Cells Suitable for Use in ACT

If $T_{CM}$ are to be used to express the CAR, suitable patient cells can be prepared as follows. First, T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anti-cancer therapy.

Suitable $T_{CM}$ can be generated as follow. Apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the CliniMACS™ separation device. Following depletion, negative fraction cells are enriched for CD62L+$T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with lentiviral vector expressing the desired CAR at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3\times10^5$ and $2\times10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CS5, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

Example 5: Expression of Cltx-IgG4(EQ)-CD28gg-Zeta

FIG. 1C depicts the results of Flow cytometric analysis of healthy donor T cells (HD187.2 $T_{CM/SCM/N}$) engineered to express the CLTX-CAR. Shown is anti-CD19 anti-Fc and anti-CD8 staining, representing co-expression of the CLTX-CAR and CD19t transgenes in both $CD8^+$ and $CD4^+$ (CD8) T cell subsets. Percentages of immunoreactive cells for transduced cells (CLTX-CAR) and untransduced cells (Mock) 18 days after CD3/CD28 bead stimulation are shown to demonstrate the capability to transduce human T cells with CLTX-CAR.

Example 6: Chlorotoxin and Cltx-IgG4(EQ)-CD28gg-Zeta T Cells Specifically Recognize Glioma Cell Line U251

Chlorotoxin conjugated to the fluorescent label, Cy5.5 (CLTX-Cy5.5) was used to assess chlorotoxin binding to various cell types. The results of this study are presented in FIGS. 2A-E (A, human peripheral blood mononuclear cells (PBMC) derived from a healthy donor; B, a human EBV-transformed lymphoblastic cell line, LCL; C, the large T antigen transformed human embryonic kidney line 293T; D, human astrocytes differentiated from healthy donor-derived induced pluripotent stem cells (iPSCs); and E, the human glioblastoma cell line U251T). Cell lines were cultured in media (untreated) or media containing 1 μM CLTX-Cy5.5 for 1 hr at 37° C. and then evaluated by flow cytometry.

Figure 2:
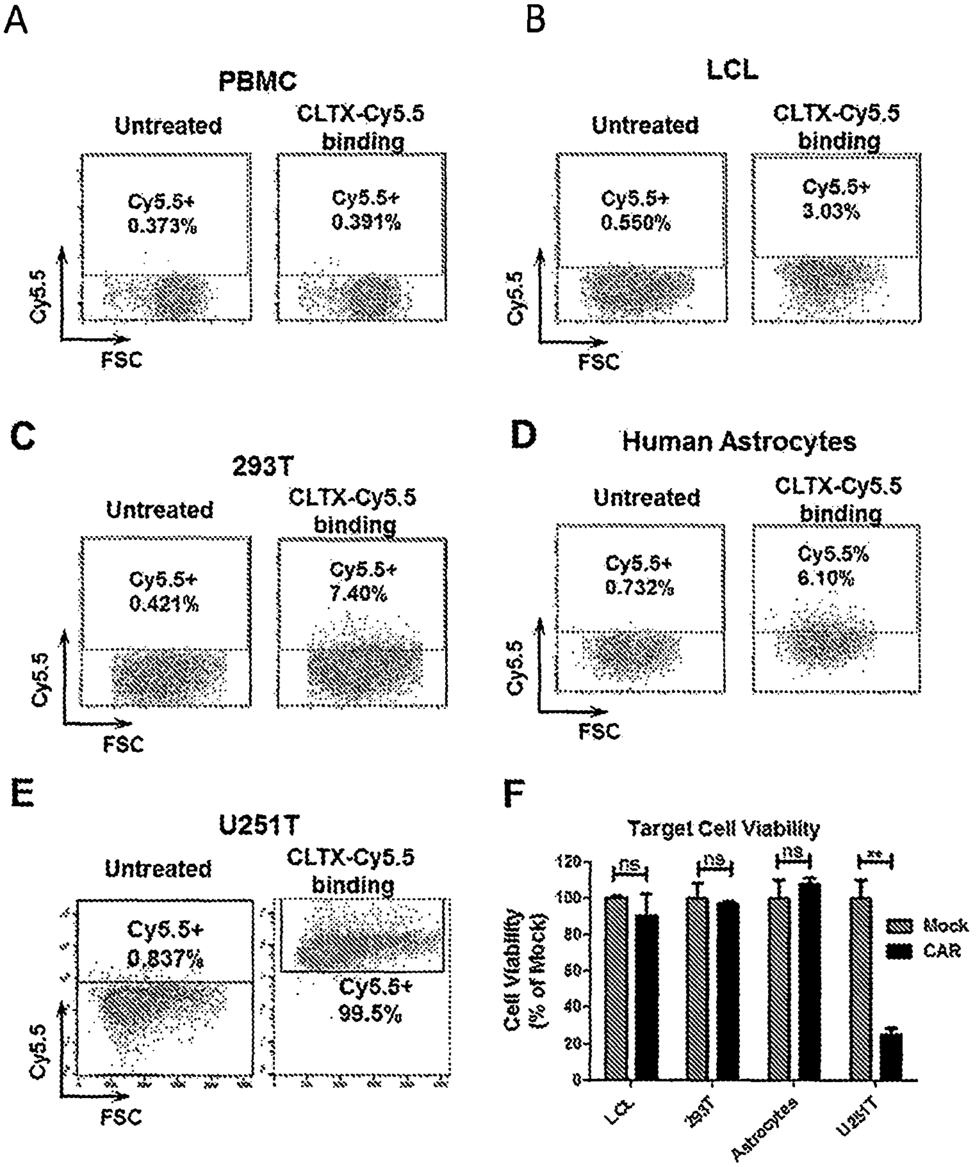
FIG. 2A-F: CLTX-CAR T cells specifically recognize glioblastoma cell line U251T. (A-E) CLTX binds to GBM cells and displays minimal binding to non-GBM cells. Shown is evaluation of chlorotoxin-conjugated Cy5.5 (CLTX-Cy5.5) binding to A, human peripheral blood mononuclear cells (PBMC) derived from a healthy donor; B, a human EBV-transformed lymphoblastic cell line, LCL; C, the large T antigen transformed human embryonic kidney line 293T; D, human astrocytes differentiated from healthy donor-derived induced pluripotent stem cells (iPSCs); and E, the human glioblastoma cell line U251T. Cell lines were cultured in media (untreated) or media containing 1 μM CLTX-Cy5.5 for 1 hr at 37° C. and then evaluated by flow cytometry. (F) Specific killing of glioma tumor line U251T by CLTX-CAR T cells, but not LCL, 293T or primary human astrocytes. Plotted are the numbers of viable target cells (LCL, 293T, astrocytes and U251T) co-cultured with CLTX-CAR T cells for 72 h, at an effector:target ratio=1:1 (15,000 T cells, 15,000 target cells), after normalizing to those co-cultured with Mock T cells for the same length of time. **: $p<0.01$; ns: non-specific, Student's t test performed between groups as indicated in the figure.

As shown in FIG. 2F, the CLTX-CAR T cells specifically kill glioma tumor line U251T, but not LCL, 293T or primary human astrocytes. Plotted are the numbers of viable target cells (LCL, 293T, astrocytes and U251T) co-cultured with CLTX-CAR T cells for 72 h, at an effector:target ratio=1:1 (15,000 T cells, 15,000 target cells), after normalizing to those co-cultured with Mock T cells for the same length of time.

Figure 3:
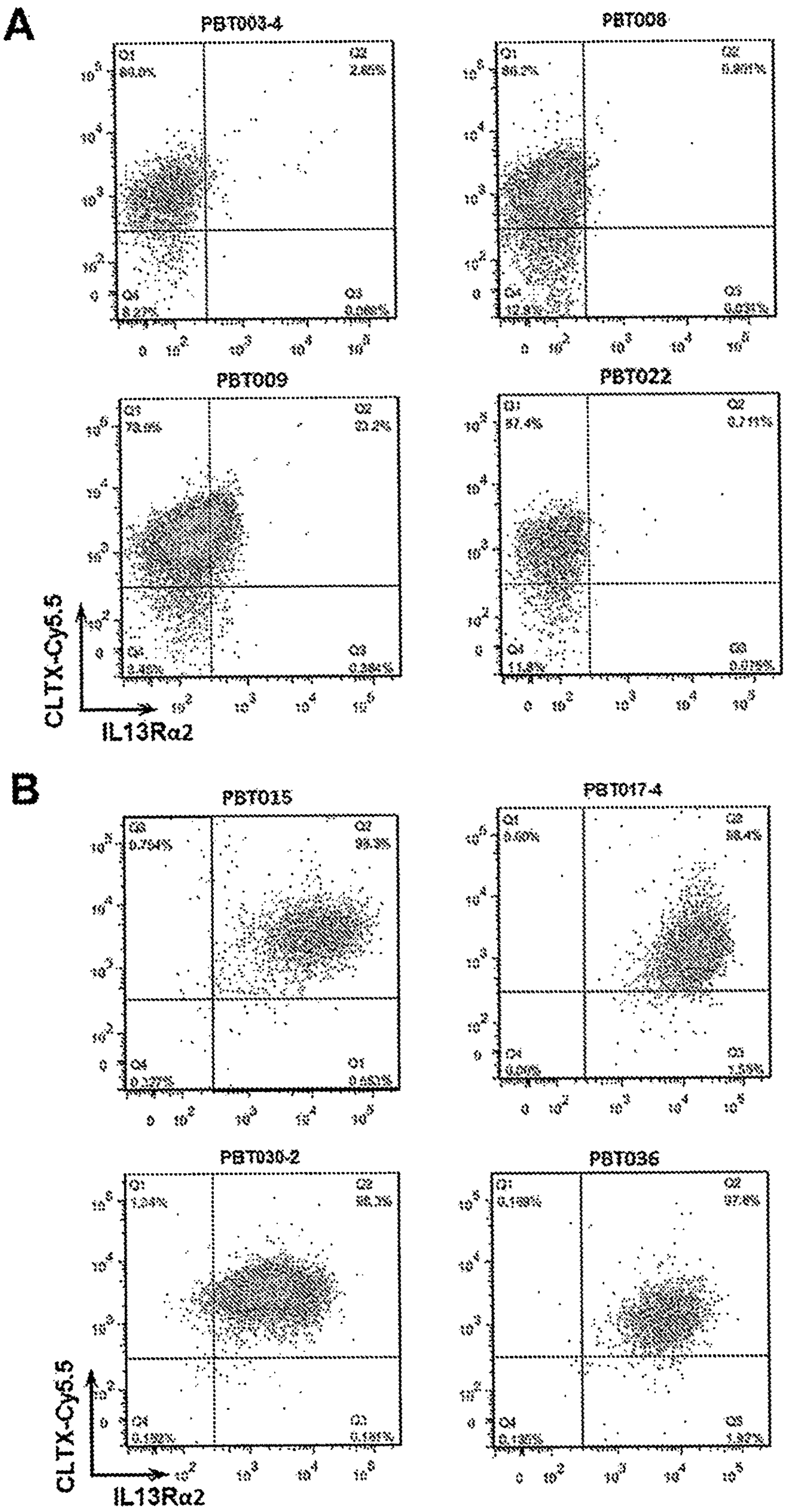
FIG. 3A-B: CLTX binding to multiple low-passage human primary brain tumor (PBT) lines is independent of IL13Rα2 expression. Flow cytometric analysis of (A) four IL13Rα2-low and (B) four IL13Rα2-high cell lines cultured in media containing 1 μM CLTX-Cy5.5 for 1 h, and then stained with PE-conjugated IL13Rα2 antibody.

Example 7: Chlorotoxin Binds to Low-Passage PBT Human Glioblastoma Lines Independent of IL13Rα2 Expression To examine whether chlorotoxin binding is independent of IL13Rα2 expression, flow cytometric analysis of IL13RA2-low cell lines and IL13RA2-high cell lines were cultured in the media containing 1 uM of CLTX-Cy5.5 for 1 h, and then stained with PE-conjugated IL13Rα2 antibody was carried out. As can be seen in FIG. 3A-B, chlorotoxin binds to low-passage PBT human glioblastoma lines independent of IL13Rα2 expression.

Figure 4:
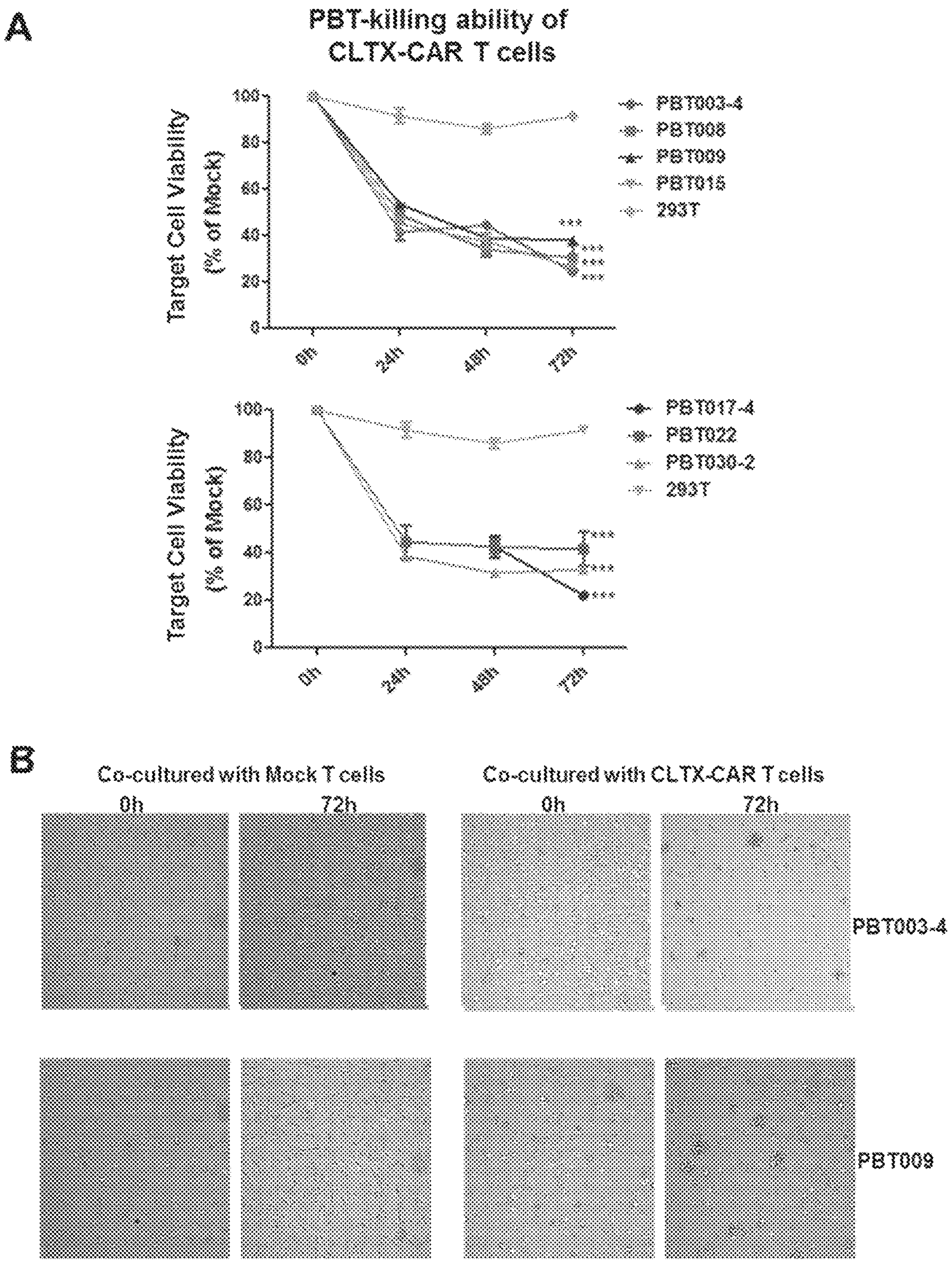
FIG. 4A-B: CLTX-CAR T cell recognition and killing of low-passage PBT human glioblastoma lines is independent of IL13Rα2 expression. (A) CLTX-CAR T cells displays statistically significant killing of a panel of primary GBM lines versus the embryonic kidney line 293T. Plotted are the numbers of viable target cells cocultured with CLTX-CAR T cells for 24, 48 and 72 h, at an effector:target ratio=1:1 (15,000 T cells, 15,000 target cells), after normalizing to those cocultured with Mock T cells for the same length of time. ***: $p<0.001$, Student's t test performed between the PBT cell viability and 293T cell viability. (B) Elimination of PBT003-4 and PBT009 tumor cells by CLTX-CAR T cells, as compared to the Mock control, observed with live cell imaging. Representative images of PBT003-4 and PBT009 cells cocultured with mock or CLTX-CAR T cells, at an effector:target ratio=1:4 (4,000 T cells, 16,000 target cells), taken by brightfield microscopy immediately after the co-culture (0 h) and after 3 days of co-culture (72 h).

Example 8: CLTX-IgG4(EQ)-CD28gg-Zeta T Cells Recognize and Kill Low-Passage PBT Human Glioblastoma Lines Independent of IL13Rα2 Expression and TCGA Molecular Subtype As shown in FIG. 4A, CLTX-CAR T cells displays statistically significant killing of a panel of primary GBM lines versus the embryonic kidney line 293T. Plotted are the numbers of viable target cells cocultured with CLTX-CAR T cells for 24, 48 and 72 h, at an effector:target ratio=1:1 (15,000 T cells, 15,000 target cells), after normalizing to those cocultured with Mock T cells for the same length of time.

FIG. 4B shows the elimination of PBT003-4 and PBT009 tumor cells by CLTX the CLTX-CAR T cells can -CAR T cells, as compared to the Mock control, observed with live cell imaging. Representative images of PBT003-4 and PBT009 cells cocultured with mock or CLTX-CAR T cells, at an effector:target ratio=1:4 (4,000 T cells, 16,000 target cells), taken by brightfield microscopy immediately after the co-culture (0 h) and after 3 days of co-culture (72 h).

Figure 5:
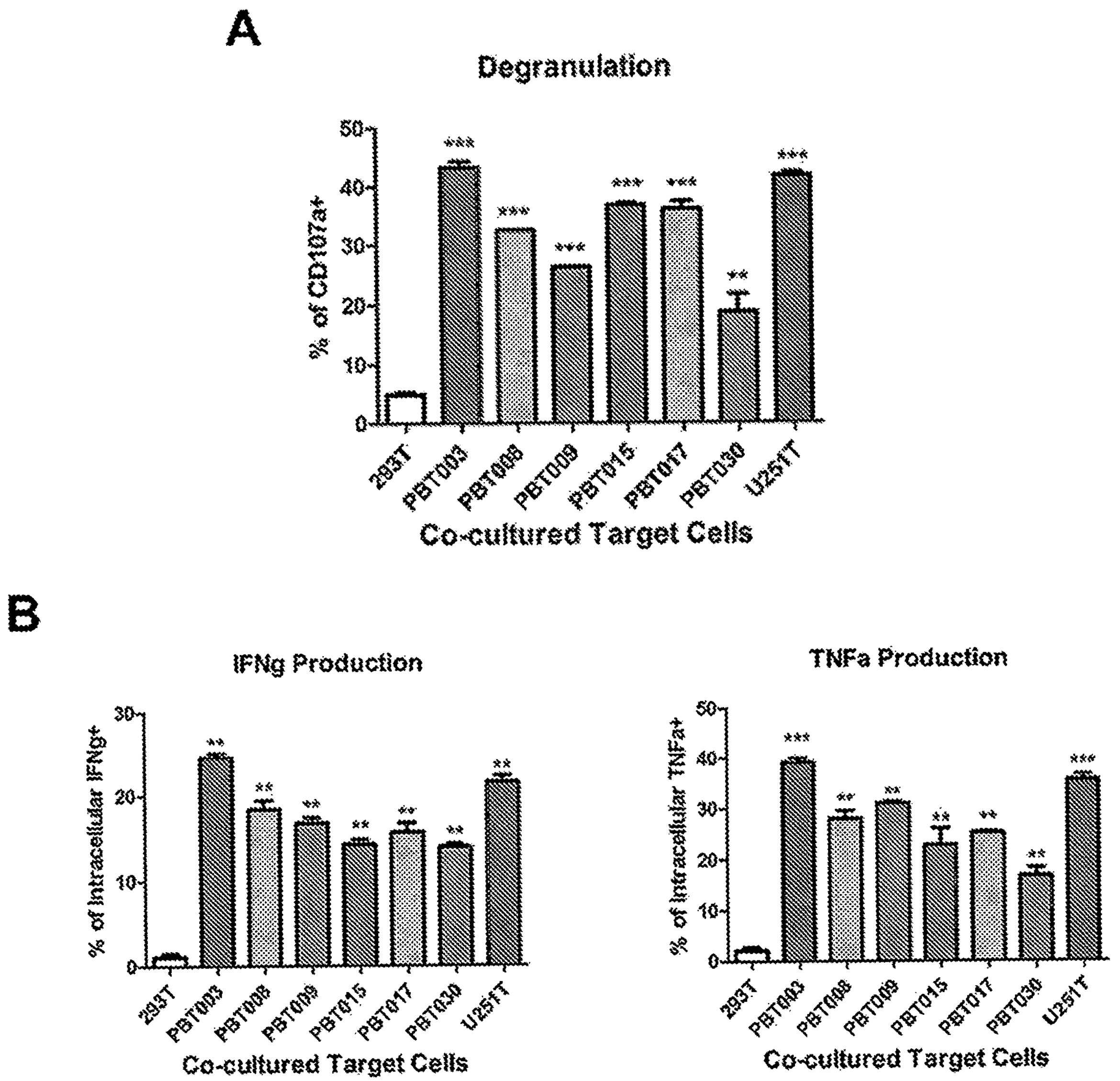
FIG. 5A-B: CLTX-CAR T cell activation after stimulating with GBM cells. T cells were stimulated by target cells for 5 h at an effector:target ratio=1:1 (25,000 T cells, 25,000 target cells) in the presence of protein transport inhibitor. The percentage of CAR-T cells undergoing degranulation was determined using flow cytoimetry by CD107a immunoreactivity (A), and cytokine production detected by intracellular staining (B). : $p<0.01$; *: $p<0.001$, one-way ANOVA with Sidak-Bonferroni correction comparing the degranulation/cytokine secretion in each of the PBT-stimulated T cells with 293T cell-stimulated T cells.

Example 9: CLTX-IgG4(EQ)-CD28gg-Zeta T Cells are Activated by Stimulation with GBM Cells T cells (mock or expressing CLTX CAR) were stimulated by target cells for 5 h at an effector:target ratio=1:1 (25,000 T cells, 25,000 target cells) in the presence of protein transport inhibitor. The percentage of CAR-T cells undergoing degranulation was determined using flow cytoimetry by CD107a immunoreactivity (FIG. 5A), and cytokine production detected by intracellular staining (FIG. 5B).

Figure 6:
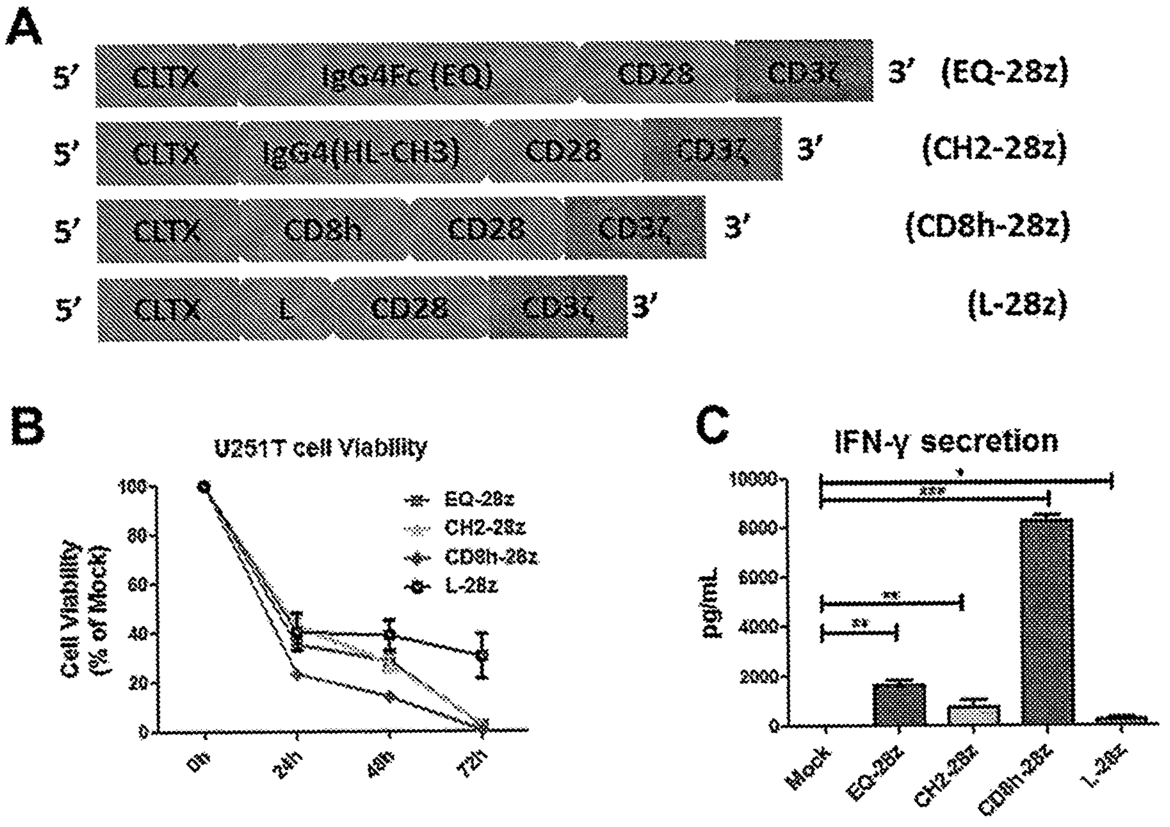
FIG. 6A-C: Anti-tumor effect of CLTX-CAR T cells with different linker designs. (A) Schematic diagram of CLTX-CAR constructs differing in linkers, including IgG4Fc (EQ), IgG4(HL-CH3), CD8 h and short linker (L) (transmembrane domain not depicted). (B) CLTX-CAR T cells with different linkers are able to kill U251T GBM cells. Plotted are the numbers of viable U251T cells cocultured with T cells harboring different CLTX-redirected constructs for 24, 48 and 72 h, at an effector:target ratio=1:1 (15,000 T cells, 15,000 target cells), after normalizing to those cocultured with Mock T cells for the same length of time. (C) CLTX-CAR T cells with different linkers display differential cytokine production levels following antigen challenge. T cells engineered with different CLTX-redirected constructs were stimulated with U251T cells at an effector:target ratio=1:1 (20,000 T cells, 20,000 target cells). IFN-γ secretion was detected by ELISA assay of the supernatant. *: $p<0.05$; : $p<0.01$; *: $p<0.001$, one-way ANOVA analysis with Sidak-Bonferroni correction comparing the indicated CAR-T cells and mock T cells.

Example 10: CLTX-CAR T Cells with Different Spacer Designs are Effective Against Tumor Cells FIG. 6A is a schematic diagram of CLTX-CAR constructs having different spacers (linkers), including IgG4Fc (EQ), IgG4(HL-CH3), CD8 h and short linker (L). All have the CD28 transmembrane domain (not depicted). As shown in FIG. 6B, CLTX-CAR T cells with different linkers are able to kill U251T GBM cells. Plotted are the numbers of viable U251T cells cocultured with T cells harboring different CLTX-redirected constructs for 24, 48 and 72 h, at an effector:target ratio=1:1 (15,000 T cells, 15,000 target cells), after normalizing to those cocultured with Mock T cells for the same length of time. As shown in FIG. 6C, CLTX-CAR T cells with different linkers display differential cytokine production levels following antigen challenge. T cells engineered with different CLTX-redirected constructs were stimulated with U251T cells at an effector:target ratio=1:1 (20,000 T cells, 20,000 target cells). IFN-γ secretion was detected by ELISA assay of the supernatant.

Figure 7:
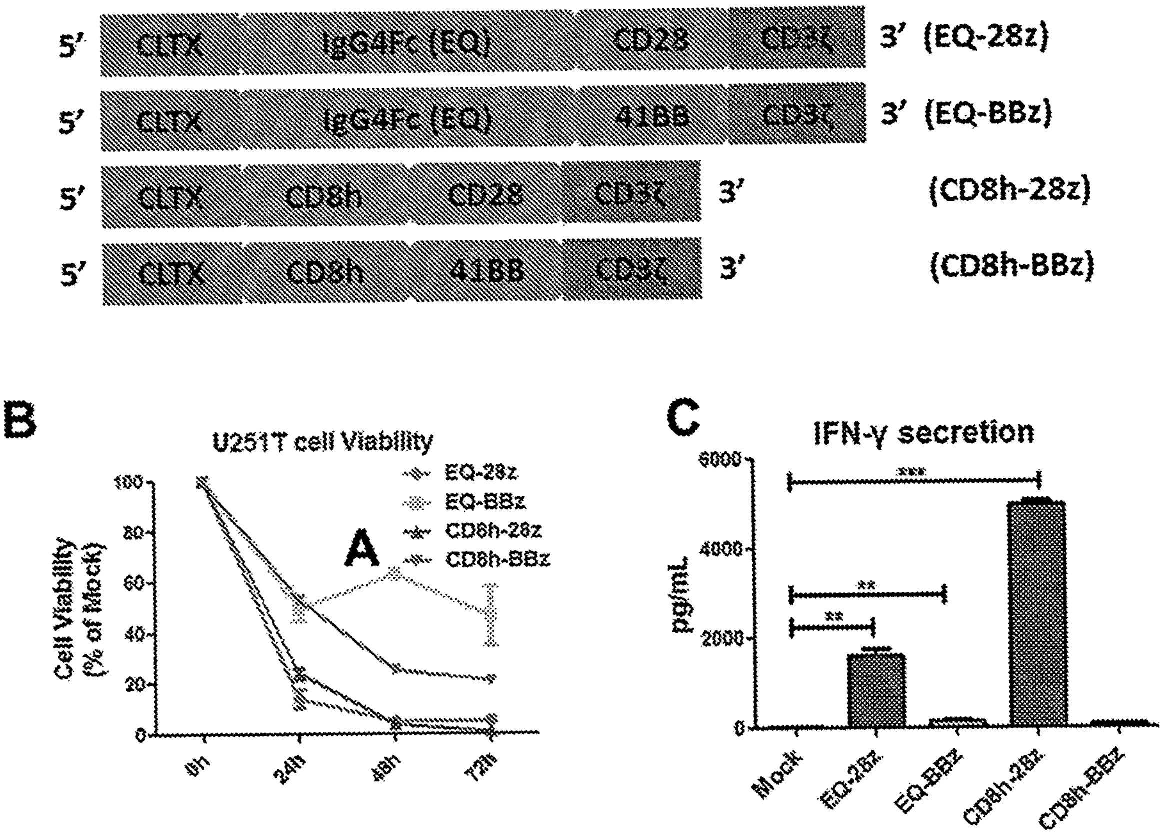
FIG. 7A-C: Anti-tumor effect of CLTX-CAR T cells with different intracellular signaling domains. (A) Schematic diagram of CLTX-CAR constructs differing in intracellular co-stimulatory domains CD28 and 41BB. (B) CLTX-CAR T cells with different co-stimulatory domains are able to kill U251T GBM cells. Plotted are the numbers of viable U251T cells cocultured with T cells harboring different CLTX-redirected constructs for 24, 48 and 72 h, at an effector:target ratio=1:1 (15,000 T cells, 15,000 target cells), after normalizing to those cocultured with Mock T cells for the same length of time. (C) CLTX-CAR T cells with different co-stimulatory domains produce various levels of cytokines following tumor challenge. T cells engineered with different CLTX-redirected constructs were stimulated with U251T cells at an effector:target ratio=1:1 (20,000 T cells, 20,000 target cells). IFN-γ secretion was detected by ELISA assay of the supernatant. : $p<0.01$; *: $p<0.001$, one-way ANOVA analysis with Sidak-Bonferroni correction comparing the indicated CAR-T cells and mock T cells.

Example 11: Anti-Tumor Effect of CLTX-CAR T Cells with Different Intracellular Signaling Domains FIG. 7A is a schematic diagram of CLTX-CAR constructs having different intracellular co-stimulatory domains CD28 and 41BB. As shown in FIG. 7B, CLTX-CAR T cells with different co-stimulatory domains are able to kill U251T GBM cells. Plotted are the numbers of viable U251T cells cocultured with T cells harboring different CLTX-redirected constructs for 24, 48 and 72 h, at an effector:target ratio=1:1 (15,000 T cells, 15,000 target cells), after normalizing to those cocultured with Mock T cells for the same length of time. As shown in FIG. 7C, CLTX-CAR T cells with different co-stimulatory domains produce various levels of cytokines following tumor challenge. T cells engineered with different CLTX-redirected constructs were stimulated with U251T cells at an effector:target ratio=1:1 (20,000 T cells, 20,000 target cells). IFN-γ secretion was detected by ELISA assay of the supernatant.

Figure 8:
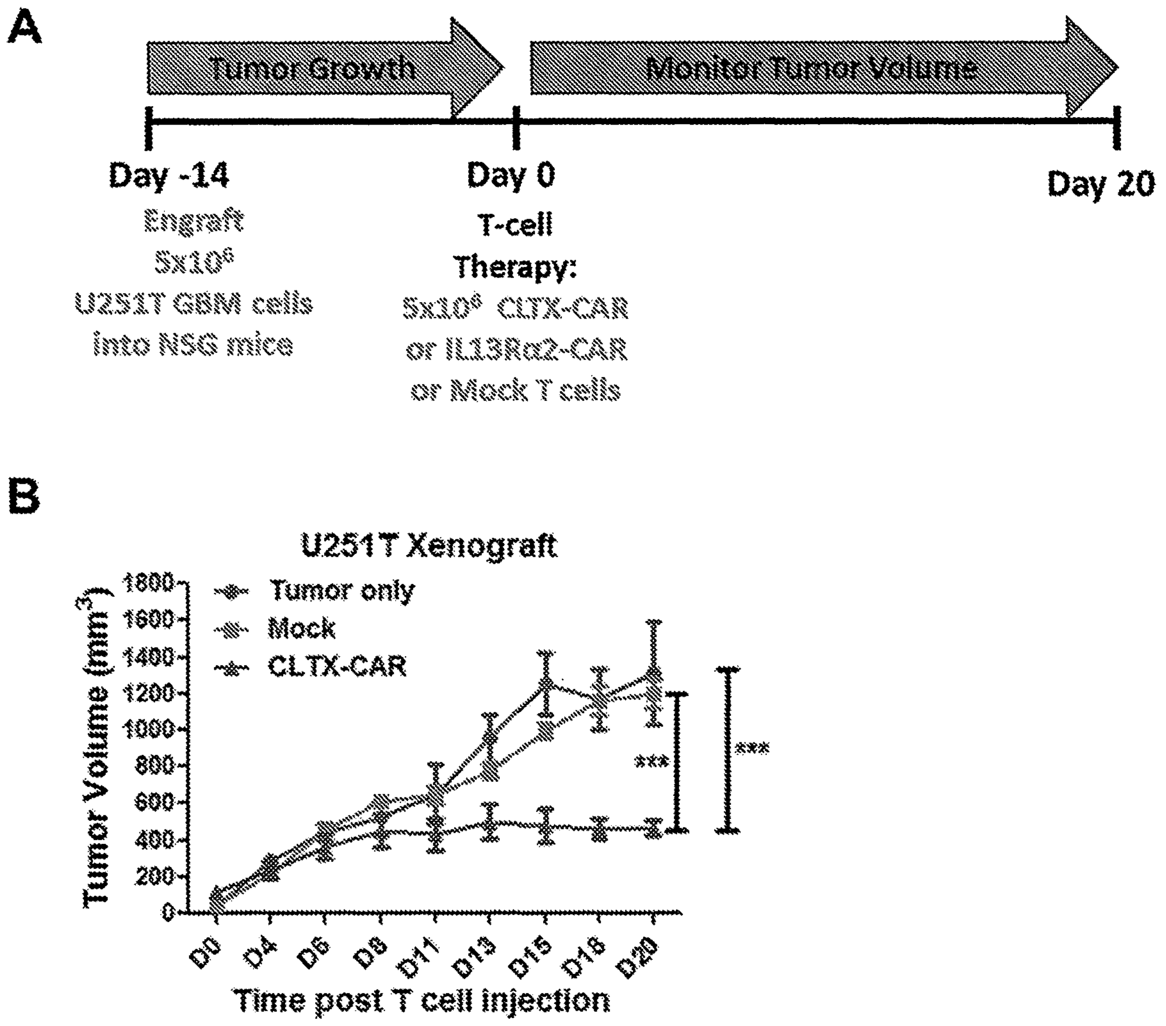
FIG. 8A-B: CLTX-CAR T cells reduce growth of established U251T GBM tumors in vivo. (A) Schema showing the U251T xenograft growth and T cell treatment in NSG mice. Mice with subcutaneously engrafted U251T cells (day −14 to day 0) were treated with PBS (tumor only), Mock T cells, or CLTX-CAR T cells. (B) Tumor progression is inhibited by CLTX-CAR T cell treatment. Growth of tumor, determined through caliper measurement, over 20 days from the time of T cell injection (day 0 to day 20). ***: $p<0.001$, one-way ANOVA analysis with Sidak-Bonferroni correction performed for data at day 20 after T cell injection, comparing tumor volumes in CLTX-CAR treated mice with the tumor only or Mock-treated groups.

Example 12: CLTX-CAR T Cells Reduce Growth of Established U251T GBM Tumors In Vivo FIG. 8A is a schematic depiction of a study of U251T xenograft growth and T cell treatment in NSG mice. Mice with subcutaneously engrafted U251T cells (day−14 to day 0) were treated with PBS (tumor only), Mock T cells, or CLTX-CAR T cells. FIG. 8B, tumor progression is inhibited by CLTX-CAR T cell treatment. Growth of tumor, determined through caliper measurement, over 20 days from the time of T cell injection (day 0 to day 20).

Example 13: Additional CLTX CAR

FIGS. 9-24 present the amino acid sequences of various additional CLTX-CAR that can be constructed and expressed as described above for the CLTX-IgG4(EQ)-CD28gg-Zeta CAR. In FIGS. 8-24 the various regions (listed below the sequence in each figure from amino to carboxy terminus are indicated by alternating underlined portions and not underlined portions. Thus, in FIG. 9 the GMCSFRa signal peptide is underlined, the chlorotoxin sequence is not underlined, the spacer (IgG4(SmP)(L235E, N297Q)) is underlined, the CD28 transmembrane sequence is not underlined, the CD28cyto (LLmGG) co-stimulatory domain is underlined, the (Gly)3 sequence separating the co-stimulatory domain from the CD3 zeta sequence is not underlined, and the CD3 zeta sequence is underlined. In FIGS. 9-23 the T2A and CD19t sequences co-expressed with the CAR are not shown. FIG. 24 depicts the CAR of FIG. 23 with a T2A (ribosomal skip sequence and a truncated CD19 included. The truncated CD19 is co-expressed with CAR, permitting a simple way in which to identify and quantify transfected cells.

Example 14: Additional Toxin Sequences

FIG. 25 depicts a sequence alignment of chlorotoxin with various chlorotoxin related toxins (Dardevet et al. 2015 Toxins (Basel) 7:1079). These toxins can, in some cases be substituted for chlorotoxin in the CAR described herein.

What is claimed is:

1. A nucleic acid molecule encoding a chimeric antigen receptor, wherein the chimeric antigen receptor comprises:

(i) chlorotoxin;

(ii) a transmembrane domain selected from the group consisting of:

a CD4 transmembrane domain, a CD8 transmembrane domain, a CD28 transmembrane domain, and a CD3ζ transmembrane domain;

(iii) a costimulatory domain; and (iv) CD3ζ signaling domain.

2. The nucleic acid molecule of claim 1 further comprising a spacer region located between the chlorotoxin and the transmembrane domain.

3. The nucleic acid molecule of claim 2, wherein the spacer region comprises 5-300 amino acids.

4. The nucleic acid molecule of claim 2, wherein the spacer region comprises an amino acid sequence selected from the group consisting of SEQ ID NOs: 2-12.

5. The nucleic acid molecule of claim 2, wherein the spacer comprises an IgG hinge region.

6. A nucleic acid molecule encoding a chimeric antigen receptor comprising an amino acid sequence selected from the group consisting of: an amino acid sequence that is identical to SEQ ID NO: 26 or differs from SEQ ID NO: 26 by no more than 5 single amino acid substitutions; an amino acid sequence that is identical to SEQ ID NO: 27 or differs from SEQ ID NO: 27 by no more than 5 single amino acid substitutions; an amino acid sequence that is identical to SEQ ID NO: 28 or differs from SEQ ID NO: 28 by no more than 5 single amino acid substitutions; an amino acid sequence that is identical to SEQ ID NO: 29 or differs from SEQ ID NO: 29 no more than 5 single amino acid substitutions; an amino acid sequence that is identical to SEQ ID NO: 30 or differs from SEQ ID NO: 30 by no more than 5 single amino acid substitutions; an amino acid sequence that is identical to SEQ ID NO: 31 or differs from SEQ ID NO: 31 by no more than 5 single amino acid substitutions; an amino acid sequence that is identical to SEQ ID NO: 32 or differs from SEQ ID NO: 32 by no more than 5 single amino acid substitutions; an amino acid sequence that is identical to SEQ ID NO: 33 or differs from SEQ ID NO: 33 by no more than 5 single amino acid substitutions; an amino acid sequence that is identical to SEQ ID NO: 34 or differs from SEQ ID NO: 34 by no more than 5 single amino acid substitutions; an amino acid sequence that is identical to SEQ ID NO: 35 or differs from SEQ ID NO: 35 by no more than 5 single amino acid substitutions; an amino acid sequence that is identical to SEQ ID NO: 36 or differs from SEQ ID NO: 36 by no more than 5 single amino acid substitutions; an amino acid sequence that is identical to SEQ ID NO: 37 or differs from SEQ ID NO: 37 by no more than 5 single amino acid substitutions; an amino acid sequence that is identical to SEQ ID NO: 38 or differs from SEQ ID NO: 38 by no more than 5 single amino acid substitutions; an amino acid sequence that is identical to SEQ ID NO: 39 or differs from SEQ ID NO: 39 by no more than 5 single amino acid substitutions; and an amino acid sequence that is identical to SEQ ID NO: 40 or differs from SEQ ID NO: 40 by no more than 5 single amino acid substitutions.

7. The nucleic acid molecule of claim 6, wherein the chimeric antigen receptor comprises an amino acid sequence that is identical to SEQ ID NO: 27 or differs from SEQ ID NO: 27 by no more than 5 single amino acid substitutions.

8. The nucleic acid molecule of claim 6, wherein the chimeric antigen receptor comprises an amino acid sequence that is identical to SEQ ID NO: 28 or differs from SEQ ID NO: 28 by no more than 5 single amino acid substitutions.

9. The nucleic acid molecule of claim 6, wherein the chimeric antigen receptor comprises an amino acid sequence that is identical to SEQ ID NO: 29 or differs from SEQ ID NO: 29 by no more than 5 single amino acid substitutions.

10. The nucleic acid molecule of claim 6, wherein the chimeric antigen receptor comprises an amino acid sequence that is identical to SEQ ID NO: 30 or differs from SEQ ID NO: 30 by no more than 5 single amino acid substitutions.

11. The nucleic acid molecule of claim 6, wherein the chimeric antigen receptor comprises an amino acid sequence that is identical to SEQ ID NO: 31 or differs from SEQ ID NO: 31 by no more than 5 single amino acid substitutions.

12. The nucleic acid molecule of claim 6, wherein the chimeric antigen receptor comprises an amino acid sequence that is identical to SEQ ID NO: 32 or differs from SEQ ID NO: 32 by no more than 5 single amino acid substitutions.

13. The nucleic acid molecule of claim 6, wherein the chimeric antigen receptor comprises an amino acid sequence that is identical to SEQ ID NO: 33 or differs from SEQ ID NO: 33 by no more than 5 single amino acid substitutions.

14. The nucleic acid molecule of claim 6, wherein the chimeric antigen receptor comprises an amino acid sequence that is identical to SEQ ID NO: 34 or differs from SEQ ID NO: 34 by no more than 5 single amino acid substitutions.

15. The nucleic acid molecule of claim 6, wherein the chimeric antigen receptor comprises an amino acid sequence that is identical to SEQ ID NO: 35 or differs from SEQ ID NO: 35 by no more than 5 single amino acid substitutions.

16. The nucleic acid molecule of claim 6, wherein the chimeric antigen receptor comprises an amino acid sequence that is identical to SEQ ID NO: 36 or differs from SEQ ID NO: 36 by no more than 5 single amino acid substitutions.

17. The nucleic acid molecule of claim 6, wherein the chimeric antigen receptor comprises an amino acid sequence that is identical to SEQ ID NO: 37 or differs from SEQ ID NO: 37 by no more than 5 single amino acid substitutions.

18. The nucleic acid molecule of claim 6, wherein the chimeric antigen receptor comprises an amino acid sequence that is identical to SEQ ID NO: 38 or differs from SEQ ID NO: 38 by no more than 5 single amino acid substitutions.

19. The nucleic acid molecule of claim 6, wherein the chimeric antigen receptor comprises an amino acid sequence that is identical to SEQ ID NO: 39 or differs from SEQ ID NO: 39 by no more than 5 single amino acid substitutions.

20. The nucleic acid molecule of claim 6, wherein the chimeric antigen receptor comprises an amino acid sequence that is identical to SEQ ID NO: 40 or differs from SEQ ID NO: 40 by no more than 5 single amino acid substitutions.

21. The nucleic acid molecule of claim 6, wherein the chimeric antigen receptor comprises an amino acid sequence that is identical to SEQ ID NO: 26 or differs from SEQ ID NO:26 by no more than 5 single amino acid substitutions.

22. The nucleic acid molecule of claim 6, wherein the single amino acid substitutions are conservative substitutions.

23. The nucleic acid molecule of claim 1, wherein the chimeric antigen receptor comprises an amino acid sequence selected from SEQ ID NOs: 26-55.

24. The nucleic acid molecule of claim 1, wherein the chimeric antigen receptor consists of an amino acid sequence selected from SEQ ID NOs: 26-55.

25. A vector comprising the nucleic acid molecule of claim 6.

26. A vector comprising an expression cassette comprising the nucleic acid molecule of claim 6.

27. A population of T cells or NK cells comprising the nucleic acid molecule claim 6.

28. A population of T cells or NK cells comprising the vector of claim 25.

29. A nucleic acid molecule encoding a chimeric antigen receptor, wherein the chimeric antigen receptor comprises: chlorotoxin comprising SEQ ID NO: 1; a spacer comprising a sequence selected from the group consisting of: SEQ ID NOs: 2-12; a transmembrane domain comprising a sequence selected from the group consisting of SEQ ID NOs: 13-20; a costimulatory domain comprising a sequence selected from the group consisting of SEQ ID NOs: 21-25, and a CD3ζ signaling domain comprising SEQ ID NO: 21.

30. The nucleic acid molecule of claim 29, comprising a spacer comprising a sequence selected from the group consisting of: SEQ ID NOs: 2, 3, 5, 8, and 9-12; a transmembrane domain comprising a sequence selected from the group consisting of SEQ ID NOs: 15 and 16; a costimulatory domain comprising a sequence selected from the group consisting of SEQ ID NOs: 22-24, and a CD3ζ signaling domain comprising SEQ ID NO: 21.

31. The nucleic acid molecule of claim 29, comprising a first costimulatory domain comprising SEQ ID NO: 22 or 23, and further comprising a second costimulatory domain comprising SEQ ID NO: 24.

32. The nucleic acid molecule of any of claims 29-31, further comprising the sequence GGG between the costimulatory domain and the CD3ζ signaling domain.

33. The nucleic acid molecule of claim 31, further comprising the sequence GGG between the first and second costimulatory domains.

34. A vector comprising the nucleic acid molecule of any of claims 29-31 and 33.

35. A vector comprising the nucleic acid molecule of claim 32.

36. A vector comprising an expression cassette comprising the nucleic acid molecule of any of claims 29-31 and 33.

37. A vector comprising an expression cassette comprising the nucleic acid molecule of claim 32.

38. A population of T cells or NK cells comprising the nucleic acid molecule of any of claims 29-31 and 33.

39. A population of T cells or NK cells comprising the nucleic acid molecule of claim 32.

40. A population of T cells or NK cells comprising the vector of claim 34.

41. A population of T cells or NK cells comprising the vector of claim 35.

* * * * *